US007928249B2

(12) United States Patent
Marks et al.

(10) Patent No.: US 7,928,249 B2
(45) Date of Patent: Apr. 19, 2011

(54) CONJUGATED MONOMERS AND POLYMERS AND PREPARATION AND USE THEREOF

(75) Inventors: Tobin J. Marks, Evanston, IL (US); Antonio Facchetti, Chicago, IL (US); Hakan Usta, Evanston, IL (US)

(73) Assignee: Northwestern University, Evanston, IL (US)

( * ) Notice: Subject to any disclaimer, the term of this patent is extended or adjusted under 35 U.S.C. 154(b) by 79 days.

(21) Appl. No.: 12/221,123

(22) Filed: Jul. 31, 2008

(65) Prior Publication Data

US 2009/0036643 A1 Feb. 5, 2009

Related U.S. Application Data

(60) Provisional application No. 60/963,087, filed on Aug. 2, 2007.

(51) Int. Cl.
*C07D 409/00* (2006.01)
(52) U.S. Cl. .......................... 549/59; 528/377; 528/380
(58) Field of Classification Search .................. 525/417; 528/380; 524/609; 549/5
See application file for complete search history.

(56) References Cited

OTHER PUBLICATIONS

Jacob Josemon et al: "Ladder-Type Pentaphenylenes and Their Polymers: Efficient Blue-Light Emitters and Electron-Accepting Materials via a Common Intermediate" Journal of the American Chemical Society, American Chemical Society, Washington DC.; US, US. vol. 126, No. 22, Jan. 1, 2004, pp. 6987-6995, XP002483843, ISSN: 0002-7863, p. 6989-p. 6990, figures 1, 2, parage 6987, paragraph 1.

M. Zhang et al.: "Conjugated alternating copolymers containing both donor and acceptor moieties in the main chain" ChemComm, Mar. 23, 2007, pp. 1704-1706, paragraph 4, p. 1705, paragraph 1.
S. Merlet, M. Birau, Z. Yuan Wang: "Synthesis and Characterization of Highly Fluoroscent Indenofluorenes" Organic Letters, vol. 4, No. 13, Jun. 6, 2002, pp. 2157-2159, XP002501157, p. 2157, paragraph 2, p. 2158.
H. Usta, A. Facchett, T. J. Marks: "Synthesis and Characterization of Electron-Deficient and Highly Soluble (Bis)Indenofluorene Building Blocks for n-Type Semiconducting Polymers" Organic Letters, vol. 10, No. 7, Mar. 4, 2008, pp. 1385-1388, XP002512258, the whole document.
H. Usta, A. Facchetti, T. J. Marks: "Air-Stable, Solution-Processable n-Channe and Ambipolar Semiconductors for Thin-Film Transistor Based on the Idenofluorenebis(dicyanovinylene) Core" Journal of the American Chemcial Society, vol. 130, Jun. 11, 2008, pp. 8580-8581, XP002501159, the whole document.
W. Frank, R. Gompper: "Electron-rich and electron-poor pentalene derivaties" Tetrahedron Letters, vol. 28, No. 27, 1987, pp. 3083-3086, XP002501154, p. 3086, paragraph 1.
A. Padwa, U. Chiacchio, D. J. Fiarfax, J. M. Kassir, A. Litrico, M. A. Semones, S. L. Xu: "A Comparative Study of the Decomposition of o-Alkynyl Diazo Ketones. Synthesis of Polysubstituted beta-Napthols via Arylketene Intermediates" Journal of Organic Chemistry, vol. 58, 1993, pp. 6429-6437, XP00250115, p. 6433.

*Primary Examiner* — James Seidleck
*Assistant Examiner* — Shane Fang
(74) *Attorney, Agent, or Firm* — K&L Gates LLP

(57) ABSTRACT

Disclosed are new conjugated compounds (e.g., monomers and polymers) that include ladder-type moieties which can be used for preparing semiconducting materials. Such conjugated compounds can exhibit high n-type carrier mobility and/or good current modulation characteristics. Compounds of the present teachings also can exhibit ambipolar semiconducting activity. In addition, the compounds of the present teachings can possess certain processing advantages such as solution-processability and/or good stability in ambient conditions.

71 Claims, 20 Drawing Sheets

CONJUGATED MONOMERS AND POLYMERS AND PREPARATION AND USE THEREOF

CROSS REFERENCE TO RELATED APPLICATION

This application claims priority to and the benefit of U.S. Provisional Patent Application Ser. No. 60/963,087, filed on Aug. 2, 2007, the disclosure of which is incorporated by reference in its entirety.

STATEMENT REGARDING FEDERALLY SPONSORED RESEARCH OR DEVELOPMENT

This invention, in part, was made with federal government support under Grant Nos. N00014-02-1-0909 and N00014-05-1-0541 awarded by the Office of Naval Research (ONR), both to Northwestern University. The United States Government has certain rights in this invention.

BACKGROUND

Conjugated polymers have been a major focus of scientific and technological research during the past few decades due to their potential use as semiconductors and electroactive materials in organic electronics, particularly in thin film transistors, photovoltaic cells, and light-emitting devices. See, e.g., Sirringhaus, H. et al., *Science*, 280: 1741-1744 (1998). Among these, organic thin film transistors (OTFTs) are considered viable alternatives to more traditional, mainstream transistors based on inorganic materials because they combine the advantages of large area coverage, low costs, and structural flexibility. See, e.g., Horowitz, G., *Adv. Mater.*, 10: 365-377 (1998). Transistors are the key components used for amplification and switching in all modern electronics. Two important device performance metrics of organic transistors are the charge carrier mobility ($\mu$) and current on/off ratio ($I_{on}/I_{off}$).

Although charge carrier mobilities are approaching 1 $cm^2V^{-1}s^{-1}$ for n-type and 10 $cm^2V^{-1}s^{-1}$ for p-type molecular semiconductors, the mobility values for polymeric semiconductors still remain one to two orders of magnitude below these values. See, e.g., Dimitrakopoulos, C. D. et al., *Adv. Mater.*, 14: 99-117 (2002). Design, synthesis, and characterization of new $\pi$-conjugated polymeric semiconductors for OTFTs are of great interest due to the intrinsic technological attributes of polymers, such as compatibility with simple direct-write printing techniques, ease of film formation, compatibility with low-cost manufacturing processes and compatibility with flexible plastic circuits. See, e.g., Zhu, Y. et al., *Macromolecules*, 38: 7983-7991 (2005). Although mobilities as high as 0.1 $cm^2 V^{-1}s^{-1}$ have been obtained for p-type polymers (see, e.g., Sirringhaus, H. et al., *Nature*, 401: 685-687 (1999)), soluble n-type polymers are rare, with the highest reported mobility using practical conditions approaching only $10^{-6} cm^2 V^{-1}s^{-1}$. Although a mobility of 0.1 $cm^2 V^{-1} s^{-1}$ has been reported for an n-type polymer, this was achieved only after post-solution-casting modifications, a procedure that is not practical for general applications. See, e.g., Babel, A. et al.; *J. Am. Chem. Soc.*, 125: 13656-13657 (2003).

SUMMARY

In light of the foregoing, the present teachings provide organic semiconductor materials and associated compositions, composites, and/or devices that can address various deficiencies and shortcomings of the state-of-the-art, including those outlined above.

More specifically, the present teachings provide new conjugated compounds (e.g., monomers and polymers) that include ladder-type moieties to promote desired semiconducting activity. Such conjugated compounds can exhibit high n-type carrier mobility and/or good current modulation characteristics. Compounds of the present teachings can also exhibit ambipolar semiconducting activity. In addition, the compounds of the present teachings can possess certain processing advantages such as solution-processability and/or good stability in ambient conditions.

The compounds of the present teachings generally include a planar $\pi$-conjugated core. Examples include indacene, indenofluorene, and tetraphenylene, as well as their analogs in which one or more carbon atoms are replaced with a heteroatom such as O, S, Si, Se, N or P. Without wishing to be bound by any particular theory, the highly $\pi$-conjugated and planar nature of these cores are believed to allow $\pi$-electron delocalization and to provide good intermolecular $\pi$-stacking.

To further enhance the physical and/or electrochemical properties of these cores, one or more electron-withdrawing groups such as carbonyl groups and/or malononitrile groups can be introduced into the $\pi$-conjugated core. Such electron-deficient functionalities can contribute to low-lying LUMO levels, and promote semiconducting activity. Furthermore, to aid solubility without causing disruption of the $\pi$-conjugation, alkyl chains (and similar groups such as alkenyl groups, alkynyl groups, haloalkyl groups, arylalkyl groups, heteroarylalkyl groups and so forth) can be introduced to modify the $\pi$-conjugated core or functional groups on the $\pi$-conjugated core.

In one aspect, the present teachings relate to compounds of formula I,

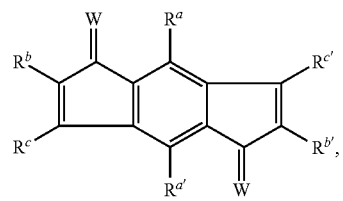

where $R^a$, $R^{a'}$, $R^b$, $R^{b'}$, $R^c$, $R^{c'}$, and W are as defined herein. The present teachings also relate to compounds of formula III, formula IV, and formula V:

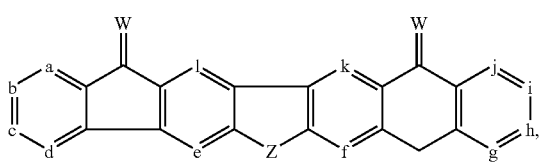

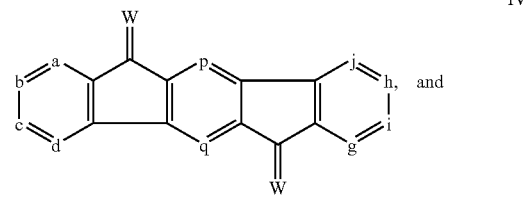

and

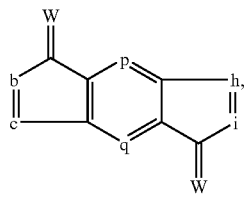

V where a, b, c, d, e, f, g, h, i, j, k, l, p, q, W, and Z are as defined herein. The compounds of formula I, formula III, formula IV, and formula V also can be used as building blocks to provide certain polymeric compounds having one or more desirable properties described herein.

Accordingly, in another aspect, the present teachings also relate to a polymerized product of one or more compounds of formula I, formula III, formula IV, and formula V. In some embodiments, the present teachings relate to polymers that include repeating units of formula II' or formula II":

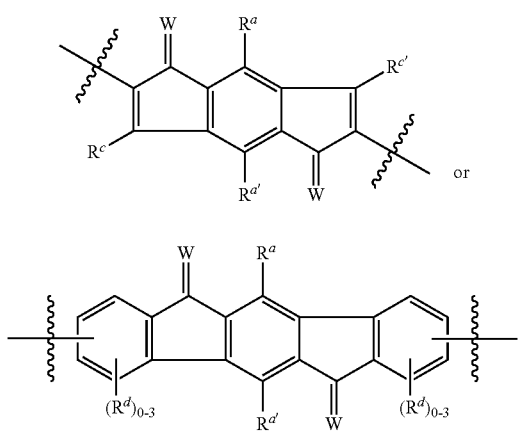

II' or

II"

where $R^a$, $R^{a'}$, $R^c$, $R^{c'}$, $R^d$, and W are as defined herein. In some embodiments, the present teachings relate to polymers that include a repeating unit of formula VI:

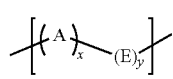

VI wherein:

A, at each occurrence, independently has formula III', formula IV', or formula V':

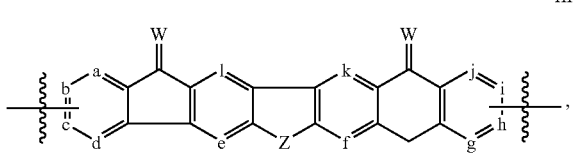

III'

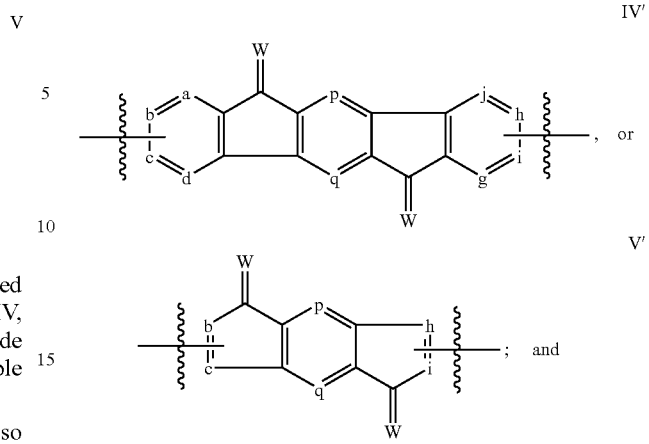

IV'

, or

V'

; and

E, at each occurrence, independently is a divalent $C_{6-14}$ aryl group or a divalent 5-14 membered heteroaryl group, each of which optionally can be substituted as described herein, and a, b, c, d, e, f, g, h, i, j, k, l, p, q, x, y, W, and Z are as defined herein.

In addition, the present teachings provide methods of preparing such compounds, as well as semiconductor materials and various compositions, composites, and devices that incorporate the compounds disclosed herein.

The foregoing as well as other features and advantages of the present teachings will be more fully understood from the following figures, description, and claims.

BRIEF DESCRIPTION OF DRAWINGS

It should be understood that the drawings described below are for illustration purposes only. The drawings are not intended to limit the scope of the present teachings in any way.

DETAILED DESCRIPTION

Figure 1A:
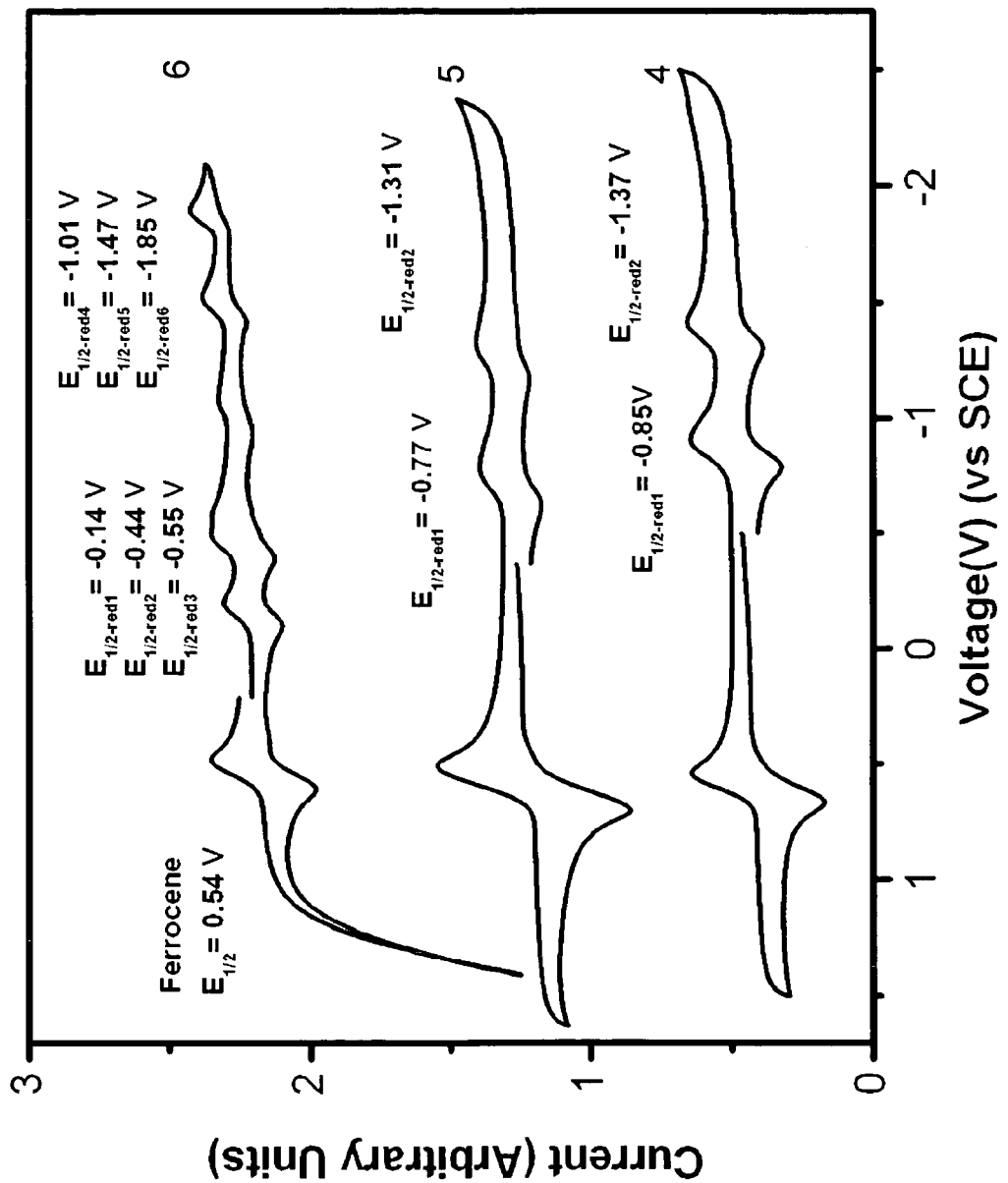
FIG. 1A shows cyclic voltammograms of exemplary compounds of the present teachings (4, 5, and 6) in THF. (Ferrocene was used as an internal standard with its peak adjusted to 0.54 V).

The present teachings relate to small molecule compounds based on a ladder-type π-conjugated core. These compounds can be polymerized or co-polymerized with other moieties to provide polymeric compounds that exhibit good semiconducting activity. The present teachings further relate to methods for preparing these compounds, as well as to compositions, composites, materials, articles, structures, and devices that incorporate such compounds.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

As used herein, "polymer" or "polymeric compound" refers to a molecule including a plurality of repeating units connected by covalent chemical bonds. The polymer can have only one type of repeating unit as well as two or more types of different repeating units. In the former case, the polymer can be referred to as a homopolymer and is the product of self-polymerization of a certain monomer. In the latter case, the term "copolymer" or "copolymeric compound" can be used instead, especially when the polymer includes chemically significantly different repeating units. The co-polymer is a product of polymerization of two or more different monomers. Regardless of how many types of repeating units it has, a polymer can be linear or branched. Branched polymers can include dendritic polymers, such as dendronized polymers, hyperbranched polymers, brush polymers (also called bottle-brushes), and so forth. Unless specified otherwise, the assembly of the repeating units in the copolymer can be head-to-tail, head-to-head, or tail-to-tail. In addition, unless specified otherwise, the copolymer can be a random copolymer, an alternating copolymer, or a block copolymer.

As used herein, "solution-processable" refers to compounds, materials, or compositions that can be used in various solution-phase processes including spin-coating, printing (e.g., inkjet printing), spray coating, electrospray coating, drop casting, dip coating, and blade coating.

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and isopropyl), butyl (e.g., n-butyl, isobutyl, sec-butyl, tert-butyl), pentyl groups (e.g., n-pentyl, isopentyl, neopentyl), hexyl, heptyl, and so forth. In various embodiments, an alkyl group can have 1 to 30 carbon atoms, i.e., a $C_{1-30}$ alkyl group. In some embodiments, an alkyl group can have 1 to 20 carbon atoms, i.e., a $C_{1-20}$ alkyl group. In certain embodiments, an alkyl group can have 1 to 6 carbon atoms, and can be referred to as a "lower alkyl group." Examples of lower alkyl groups include methyl, ethyl, propyl (e.g., n-propyl and isopropyl), and butyl groups (e.g., n-butyl, isobutyl, sec-butyl, tert-butyl). In some embodiments, alkyl groups can be substituted as disclosed herein. An alkyl group is generally not substituted with another alkyl group or an alkenyl or alkynyl group.

As used herein, "haloalkyl" refers to an alkyl group having one or more halogen substituents. Examples of haloalkyl groups include $CF_3$, $C_2F_5$, $CHF_2$, $CH_2F$, $CCl_3$, $CHCl_2$, $CH_2Cl$, $C_2Cl_5$, and so forth. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-30}$ haloalkyl group can have the formula —$C_mH_{2m+1-t}X_t$, where X is F, Cl, Br, or I, m is an integer in the range of 1 to 30, and t is an integer in the range of 1 to 61, provided that t is less than or equal to 2m+1. Haloalkyl groups that are not perhaloalkyl groups optionally can be substituted as disclosed herein.

As used herein, "arylalkyl" refers to an -alkyl-aryl group, where the arylalkyl group is covalently linked to the defined chemical structure via the alkyl group. An arylalkyl group is within the definition of an —Y—$C_{6-14}$ aryl group, where Y is as defined herein. An example of an arylalkyl group is a benzyl group (—$CH_2$—$C_6H_5$). An arylalkyl group can be optionally substituted, i.e., the aryl group and/or the alkyl group can be substituted as disclosed herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and so forth. The one or more carbon-carbon double bonds can be internal (such as in 2-butene) or terminal (such as in 1-butene). In various embodiments, an alkenyl group can have 2 to 30 carbon atoms, i.e., a $C_{2-30}$ alkenyl group. In some embodiments, an alkenyl group can have 2 to 20 carbon atoms, i.e., a $C_{2-20}$ alkenyl group. In some embodiments, alkenyl groups can be substituted as disclosed herein. An alkenyl group is generally not substituted with another alkenyl group or an alkyl or alkynyl group.

As used herein, "alkynyl" refers to a straight-chain or branched alkyl group having one or more triple carbon-carbon bonds. Examples of alkynyl groups include ethynyl, propynyl, butynyl, pentynyl, and so forth. The one or more triple carbon-carbon bonds can be internal (such as in 2-butyne) or terminal (such as in 1-butyne). In various embodiments, an alkynyl group can have 2 to 30 carbon atoms, i.e., a $C_{2-30}$ alkynyl group. In some embodiments, an alkynyl group can have 2 to 20 carbon atoms, i.e., a $C_{2-20}$ alkynyl group. In some embodiments, alkynyl groups can be substituted as disclosed herein. An alkynyl group is generally not substituted with another alkynyl group or an alkyl or alkenyl group.

As used herein, "cycloalkyl" refers to a non-aromatic carbocyclic group including cyclized alkyl, alkenyl, and alkynyl groups. A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro [4.5]decanyl groups, as well as their homologs, isomers, and so forth. In some embodiments, cycloalkyl groups can be substituted as disclosed herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 20 ring atoms, for example, 3 to 14 ring atoms (i.e., 3-14 membered cycloheteroalkyl group). One or more N, P, S, or Se atoms (e.g., N or S) in a cycloheteroalkyl ring can be oxidized (e.g., morpholine N-oxide, thiomorpholine S-oxide, thiomorpholine S,S-dioxide). In some embodiments, nitrogen atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and so forth. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and so forth. In some embodiments, cycloheteroalkyl groups can be substituted as disclosed herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have from 6 to 14 carbon atoms in its ring system, which can include multiple fused rings. In some embodiments, a polycyclic aryl group can have from 8 to 14 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/ aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and so forth. In some embodiments, aryl groups can be substituted as disclosed herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —C$_6$F$_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least 1 ring heteroatom selected from oxygen (O), nitrogen (N), sulfur (S), silicon (Si), and selenium (Se) or a polycyclic ring system where at least one of the rings present in the ring system is aromatic and contains at least 1 ring heteroatom. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have, for example, from 5 to 14 ring atoms and contain 1-5 ring heteroatoms. The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

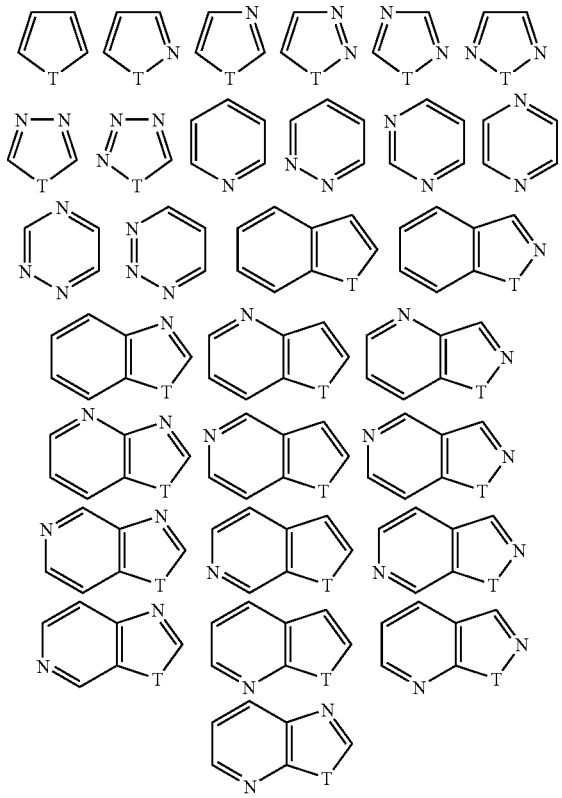

where T is O, S, NH, N-alkyl, N-aryl, N-(arylalkyl) (e.g., N-benzyl), SiH$_2$, SiH-(alkyl), Si(alkyl)$_2$, SiH-(arylalkyl), Si-(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and so forth. Further examples of heteroaryl groups include 4,5,6,7-tetrahydroindolyl, tetrahydroquinolinyl, benzothienopyridinyl, benzofuropyridinyl groups, and so forth. In some embodiments, heteroaryl groups can be substituted as disclosed herein.

Compounds of the present teachings can include a "divalent group" defined herein as a linking group capable of forming a covalent bond with two other moieties. For example, compounds of the present teachings can include a divalent C$_{1-20}$ alkyl group, such as, for example, a methylene group.

The electron-donating or electron-withdrawing properties of several hundred of the most common substituents, reflecting all common classes of substituents have been determined, quantified, and published. The most common quantification of electron-donating and electron-withdrawing properties is in terms of Hammett a values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein. It should be understood that the term "electron-accepting group" can be used synonymously herein with "electron acceptor" and "electron-withdrawing group". In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halide (e.g., F, Cl, Br, I), —NO$_2$, —CN, —NC, —OH, —OR$^o$, —SH, —SR$^o$, —S(R$^o$)$_2^+$, —NH$_2$, —NHR$^o$, —NR$^o_2$, —N(R$^o$)$_3^+$, —SO$_3$H, —SO$_2$R$^o$, —SO$_3$R$^o$, —SO$_2$NHR$^o$, —SO$_2$N(R$^o$)$_2$, —COOH, —COR$^o$, —COOR$^o$, —CONHR$^o$, —CON(R$^o$)$_2$, C$_{1-30}$ haloalkyl groups, C$_{6-14}$ aryl groups, and 5-14 membered heteroaryl groups; where R$^o$ is a C$_{1-30}$ alkyl group, a C$_{2-30}$ alkenyl group, a C$_{2-30}$ alkynyl group, a C$_{1-30}$ haloalkyl group, a C$_{1-30}$ alkoxy group, a C$_{6-14}$ aryl group, a C$_{3-14}$ cycloalkyl group, a 3-14 membered cycloheteroalkyl group, and a 5-14 membered heteroaryl group, each of which can be optionally substituted with 1-5 R$^9$ and R$^9$ is as defined herein.

At various places in the present specification, substituents of compounds are disclosed in groups or in ranges. It is specifically intended that the description include each and every individual subcombination of the members of such groups and ranges. For example, the term "C$_{1-6}$ alkyl" is specifically intended to individually disclose C$_1$, C$_2$, C$_3$, C$_4$, C$_5$, C$_6$, C$_{1-6}$, C$_{1-5}$, C$_{1-4}$, C$_{1-3}$, C$_{1-2}$, C$_{2-6}$, C$_{2-5}$, C$_{2-4}$, C$_{2-3}$, C$_{3-6}$, C$_{3-5}$, C$_{3-4}$, C$_{4-6}$, C$_{4-5}$, and C$_{5-6}$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

As used herein, a "p-type semiconducting material" or a "p-type semiconductor" refers to a semiconducting material having holes as the majority current carriers. In some embodiments, when a p-type semiconducting material is deposited on a substrate, it can provide a hole mobility in excess of about $10^{-5}$ cm$^2$/Vs. In the case of field-effect devices, a p-type semiconductor can also exhibit a current on/off ratio of greater than about 10.

As used herein, an "n-type semiconducting material" or an "n-type semiconductor" refers to a semiconducting material having electrons as the majority current carriers. In some embodiments, when an n-type semiconducting material is deposited on a substrate, it can provide an electron mobility in excess of about $10^{-5}$ cm$^2$/Vs. In the case of field-effect devices, an n-type semiconductor can also exhibit a current on/off ratio of greater than about 10.

As used herein, "field effect mobility" refers to a measure of the velocity with which charge carriers, for example, holes (or units of positive charge) in the case of a p-type semiconducting material and electrons in the case of an n-type semiconducting material, move through the material under the influence of an electric field.

Throughout the specification, structures may or may not be presented with chemical names. Where any question arises as to nomenclature, the structure prevails.

In one aspect, the present teachings provide compounds having a planar π-conjugated core that can be functionalized with one or more (e.g., two or more) electron-withdrawing groups and, optionally, one or more (e.g., two or more) chemical groups that can improve solubility. The planar π-conjugated core generally includes three or more rings (e.g., 3, 5, 7 or 9), the center ring of which can be optionally functionalized with one or more solubility-enhancing groups. Other positions of the π-conjugated core can be optionally substituted as described herein.

More specifically, in one aspect, the present teachings provide compounds of formula I:

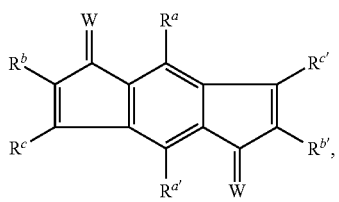

I wherein:
$R^a$ and $R^{a'}$ independently are a) H, b) a $C_{1-30}$ alkyl group, c) a $C_{2-30}$ alkenyl group, d) a $C_{2-30}$ alkynyl group, e) a $C_{1-30}$ haloalkyl group, f) a —Y—$C_{3-14}$ cycloalkyl group, g) a —Y—$C_{6-14}$ aryl group, h) a —Y-3-14 membered cycloheteroalkyl group, or i) a —Y-5-14 membered heteroaryl group, wherein each of the $C_{1-30}$ alkyl group, the $C_{2-30}$ alkenyl group, the $C_{2-30}$ alkynyl group, the $C_{1-30}$ haloalkyl group, the $C_{3-14}$ cycloalkyl group, the $C_{6-14}$ aryl group, the 3-14 membered cycloheteroalkyl group, and the 5-14 membered heteroaryl group optionally is substituted with 1-5 $R^i$ groups;

$R^b$, $R^{b'}$, $R^c$, and $R^{c'}$ independently are a) H, b) halogen, c) —CN, d) —NO$_2$, e) —OS(O)$_2$R$^e$, f) —Sn(R$^e$)$_3$, g) —B(OR$^e$)$_2$, h) —Y—R$^f$, i) a $C_{1-30}$ alkyl group, j) a $C_{2-30}$ alkenyl group, k) a $C_{2-30}$ alkynyl group, or l) a $C_{1-30}$ haloalkyl group, wherein each of the $C_{1-30}$ alkyl group, the $C_{2-30}$ alkenyl group, the $C_{2-30}$ alkynyl group, and the $C_{1-30}$ haloalkyl group optionally is substituted with 1-5 $R^i$ groups, or alternatively, each of $R^b$ and $R^c$, and $R^{b'}$ and $R^{c'}$, together with each pair of carbon atoms to which each group is attached, independently forms a $C_{6-14}$ aryl group optionally substituted with 1-5 $R^d$ groups;

W, at each occurrence, independently is O, S, NR$^e$, or C(CN)$_2$;

$R^d$, at each occurrence, independently is a) halogen, b) —CN, c) —NO$_2$, d) —OS(O)$_2$R$^e$, e) —Sn(R$^e$)$_3$, f) —B(OR$^e$)$_2$, g) —Y—R, h) =W, i) a $C_{1-30}$ alkyl group, j) a $C_{2-30}$ alkenyl group, k) a $C_{2-30}$ alkynyl group, or l) a $C_{1-30}$ haloalkyl group, wherein each of the $C_{1-30}$ alkyl group, the $C_{2-30}$ alkenyl group, the $C_{2-30}$ alkynyl group, and the $C_{1-30}$ haloalkyl group optionally is substituted with 1-5 $R^i$ groups;

$R^e$, at each occurrence, independently is H or a $C_{1-30}$ alkyl group optionally substituted with 1-5 $R^i$ groups;

$R^f$, at each occurrence, independently is -(L)$_r$-R$^g$;

L, at each occurrence, independently is a) a divalent $C_{3-14}$ cycloalkyl group, b) a divalent $C_{6-14}$ aryl group, c) a divalent 3-14 cycloheteroalkyl group, or d) a divalent 5-14 membered heteroaryl group, wherein each of a)-d) optionally is substituted with 1-5 $R^i$ groups;

$R^g$, at each occurrence, independently is a) a $C_{3-14}$ cycloalkyl group, b) a $C_{6-14}$ aryl group, c) a 3-14 cycloheteroalkyl group, or d) a 5-14 membered heteroaryl group, wherein each of a)-d) optionally is substituted with 1-5 $R^h$ groups;

$R^h$, at each occurrence, independently is a) halogen, b) —CN, c) —NO$_2$, d) —OS(O)$_2$R$^e$, e) —Sn(R$^e$)$_3$, f) —B(OR$^e$)$_2$, g) a $C_{1-30}$ alkyl group, h) a $C_{2-30}$ alkenyl group, i) a $C_{2-30}$ alkynyl group, or j) a $C_{1-30}$ haloalkyl group, wherein each of the $C_{1-30}$ alkyl group, the $C_{2-30}$ alkenyl group, the $C_{2-30}$ alkynyl group, and the $C_{1-30}$ haloalkyl group optionally is substituted with 1-5 $R^i$ groups;

$R^i$, at each occurrence, independently is a) halogen, b) —CN, e) —NO$_2$, f) —OH, g) —NH$_2$, h) —OC$_{1-10}$ alkyl, i) —NH(C$_{1-10}$ alkyl), j) —N(C$_{1-10}$ alkyl)$_2$, k) —CHO, l) —C(O)OH, m) —C(O)(C$_{1-10}$ alkyl), n) —C(O)O(C$_{1-10}$ alkyl), o) —C(O)NH$_2$, p) —C(O)NH(C$_{1-10}$ alkyl), q) —C(O)N(C$_{1-10}$ alkyl)$_2$, r) a $C_{1-30}$ alkyl group, s) a $C_{2-30}$ alkenyl group, t) a $C_{2-30}$ alkynyl group, u) a $C_{1-30}$ haloalkyl group, v) a $C_{3-14}$ cycloalkyl group, w) a $C_{6-14}$ aryl group, x) a 3-14 membered cycloheteroalkyl group, or y) a 5-14 membered heteroaryl group;

Y, at each occurrence, independently is a) a divalent $C_{1-10}$ alkyl group, b) a divalent $C_{2-10}$ alkenyl group, c) a divalent $C_{2-10}$ alkynyl group, d) a divalent $C_{1-10}$ haloalkyl group, or e) a covalent bond; and r, at each occurrence, independently is 0, 1, 2, 3, 4, 5, or 6.

It should be understood that the present teachings can exclude certain compounds. For example, the present teachings can exclude compounds having the formula:

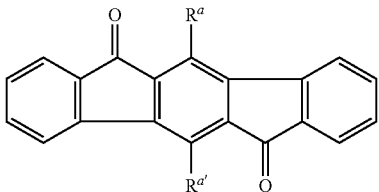

where $R^a$ and $R^{a'}$ independently are H or an unsubstituted phenyl group.

In various embodiments of compounds of formula I, W can be O or $C(CN)_2$. In some embodiments, W can be O. In some embodiments, W can be $C(CN)_2$.

In various embodiments, $R^a$ and $R^{a'}$ independently can be H, a $C_{1-30}$ alkyl group, or a $C_{1-30}$ haloalkyl group. In some embodiments, $R^a$ and $R^{a'}$ independently can be H, a $C_{6-22}$ alkyl group, or a $C_{6-22}$ haloalkyl group.

In various embodiments, compounds of the present teachings can have formula I':

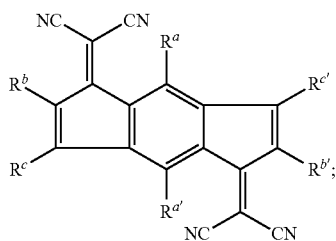

wherein $R^b$, $R^{b'}$, $R^c$, and $R^{c'}$ independently are a) H, b) halogen, c) —CN, d) —$NO_2$, e) —$OS(O)_2R^e$, f) —$Sn(R^e)_3$, g) —$B(OR^e)_2$, h) —Y—$R^f$, i) a $C_{1-30}$ alkyl group, j) a $C_{2-30}$ alkenyl group, k) a $C_{2-30}$ alkynyl group, or l) a $C_{1-30}$ haloalkyl group, wherein each of the $C_{1-30}$ alkyl group, the $C_{2-30}$ alkenyl group, the $C_{2-30}$ alkynyl group, and the $C_{1-30}$ haloalkyl group optionally can be substituted with 1-5 $R^i$ groups; and $R^a$, $R^{a'}$, $R^e$, $R^f$, $R^i$, and Y are as defined herein.

In some embodiments, $R^b$, $R^{b'}$, $R^c$, and $R^{c'}$ independently can be H, halogen, —CN, —$NO_2$, —$OS(O)_2R^e$, —$Sn(R^e)_3$, —$B(OR^e)_2$, or —Y—$R^f$, where $R^e$, $R^f$, and Y are as defined herein. For example, $R^b$, $R^{b'}$, $R^c$, and $R^{c'}$ independently can be H, halogen, —$OS(O)_2R^e$, —$Sn(R^e)_3$, —$B(OR^e)_2$, or —Y—$R^f$, where $R^e$, $R^f$, and Y are as defined herein. In certain embodiments, Y can be a covalent bond. In certain embodiments, $R^b$, $R^{b'}$, $R^c$, and $R^{c'}$ independently are H or halogen. For example, at least one of $R^b$, $R^{b'}$, $R^c$, and $R^{c'}$ can be halogen, including Br. In certain embodiments, $R^b$, $R^{b'}$, $R^c$, and $R^{c'}$ independently can be H or -(L)$_r$-$R^g$, where L, $R^g$, and r are as defined herein. In particular embodiments, each of $R^c$ and $R^{c'}$ can be H.

In various embodiments, r can be 0, 1, or 2. In various embodiments, L can be a divalent $C_{6-14}$ aryl group or a divalent 5-14 membered heteroaryl group, each of which optionally can be substituted with 1-5 $R^i$ groups, where $R^i$ is as defined herein. In some embodiments, L can be a divalent phenyl group optionally substituted with 1-4 $R^i$ groups. In certain embodiments, L can be a divalent thienyl group optionally substituted with 1-4 $R^i$ groups. In some embodiments, $R^g$ can be a $C_{6-14}$ aryl group or a 5-14 membered heteroaryl group, each of which optionally can be substituted with 1-5 $R^h$ groups, where $R^h$ is as defined herein. In certain embodiments, $R^g$ can be a phenyl group optionally substituted with 1-5 $R^h$ groups. In certain embodiments, $R^g$ can be a thienyl group optionally substituted with 1-4 $R^h$ groups. For example, -(L)$_r$-$R^g$, at each occurrence, independently can be selected from:

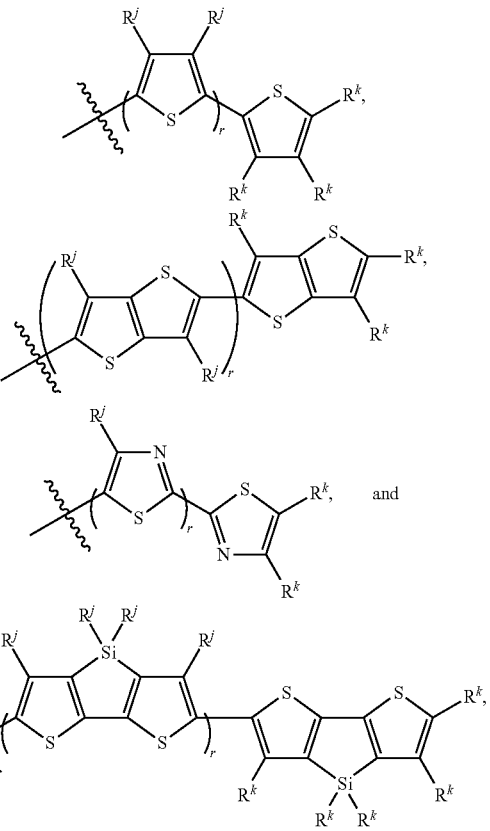

where r can be 0, 1, or 2; $R^j$, at each occurrence, independently can be H or $R^i$; $R^k$, at each occurrence, independently can be H or $R^h$; and $R^h$ and $R^i$ are as defined herein.

In various embodiments, $R^b$ and $R^c$, together with each pair of carbon atoms to which each group is attached, can form a $C_{6-14}$ aryl group optionally substituted with 1-5 $R^d$ groups, where $R^d$ is as defined herein. In some embodiments, $R^b$ and $R^c$, together with each pair of carbon atoms to which each group is attached, can form a phenyl group optionally substituted with 1-4 $R^d$ groups, where $R^d$ is as defined herein. In various embodiments, $R^{b'}$ and $R^{c'}$, together with each pair of carbon atoms to which each group is attached, can form a $C_{6-14}$ aryl group optionally substituted with 1-5 $R^d$ groups, where $R^d$ is as defined herein. In some embodiments, $R^{b'}$ and $R^{c'}$, together with each pair of carbon atoms to which each group is attached, can form a phenyl group optionally substituted with 1-5 $R^d$ groups, where $R^d$ is as defined herein.

Accordingly, in various embodiments, the compounds of the present teachings can have formula I":

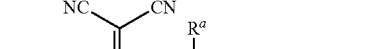

where $R^a$, $R^{a'}$, and $R^d$ are as defined herein.

In various embodiments, $R^d$, at each occurrence, independently can be selected from halogen, —CN, —$NO_2$, —OS $(O)_2R^e$, —Sn($R^e)_3$, —B(O$R^e)_2$, and —Y—$R^f$, where $R^e$, $R^f$, and Y are as defined herein. In some embodiments, Y can be a covalent bond. In some embodiments, $R^d$, at each occurrence, independently can be selected from halogen and -(L)$_r$-$R^g$, where $R^g$, L, and r are as defined herein. For example, r can be 0, 1, or 2. For example, L can be a divalent $C_{6-14}$ aryl group or a divalent 5-14 membered heteroaryl group, each of which optionally can be substituted with 1-5 $R^i$ groups, where $R^i$ is as defined herein. In certain embodiments, L can be a divalent phenyl group optionally substituted with 1-5 $R^i$ groups. In certain embodiments, L can be a divalent thienyl group optionally substituted with 1-4 $R^i$ groups. For example, $R^g$ can be a $C_{6-14}$ aryl group or a 5-14 membered heteroaryl group, each of which optionally can be substituted with 1-5 $R^h$ groups, where $R^h$ is as defined herein. In certain embodiments, $R^g$ can be a phenyl group optionally substituted with 1-5 $R^h$ groups. In certain embodiments, $R^g$ can be a thienyl group optionally substituted with 1-4 $R^h$ groups. In particular embodiments, -(L)$_r$-$R^g$, at each occurrence, can be independently selected from:

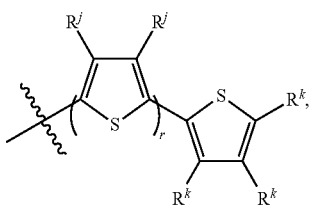

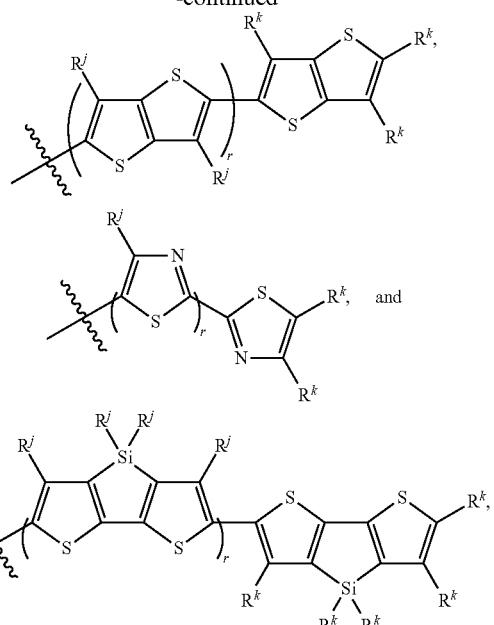

where r can be 0, 1, or 2; $R^j$, at each occurrence, independently can be H or $R^i$; $R^k$, at each occurrence, independently can be H or $R^h$; and $R^h$ and $R^i$ are as defined herein.

Exemplary compounds of formula I include:

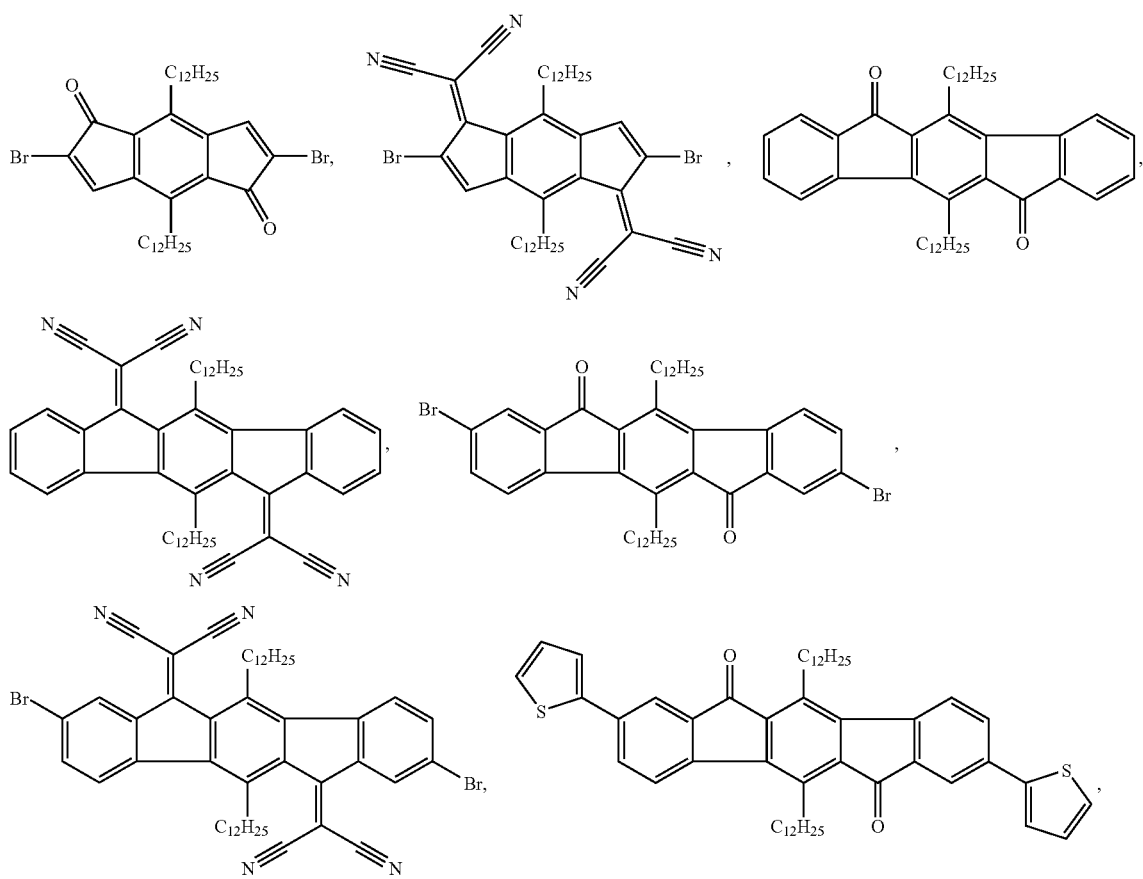

-continued
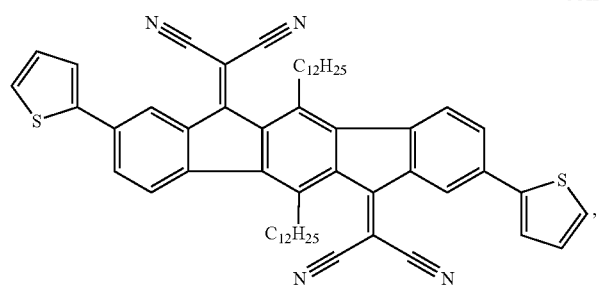
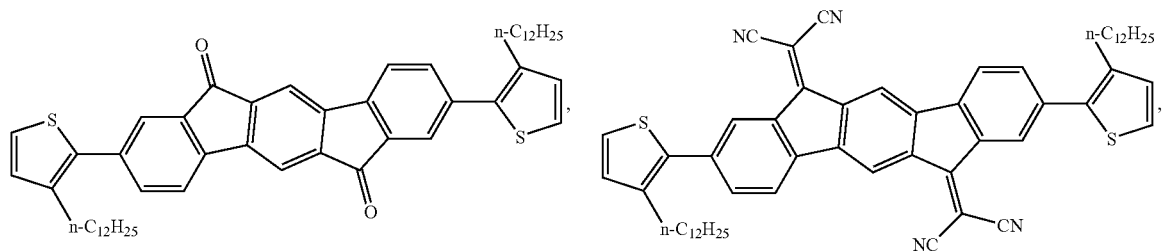
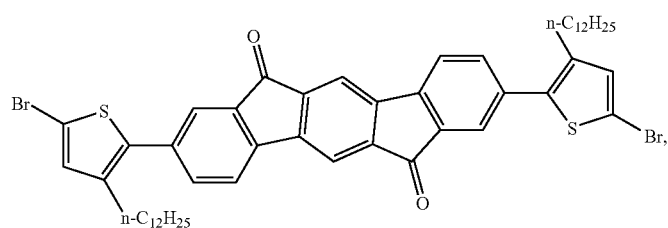
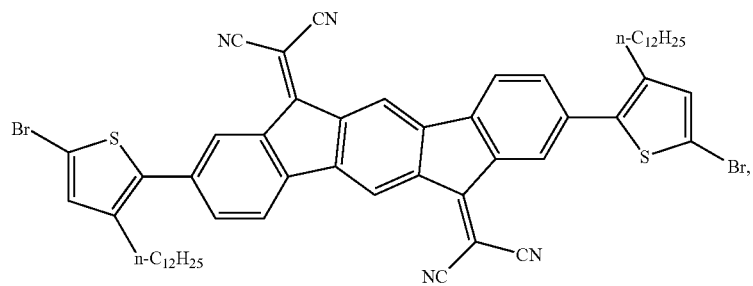
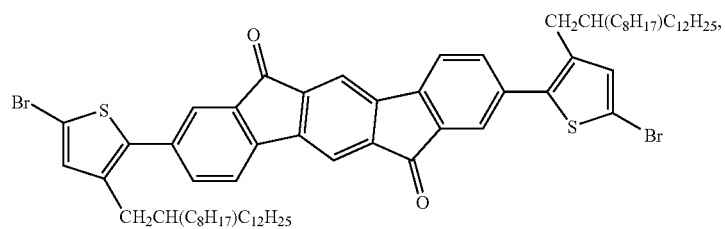
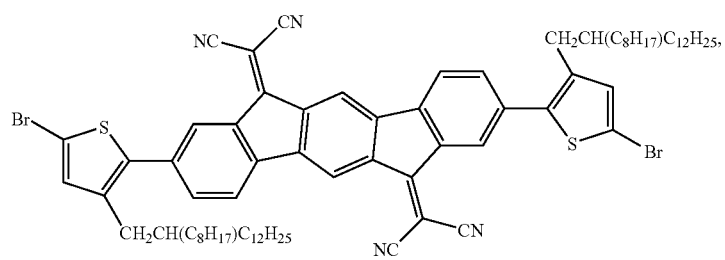

-continued

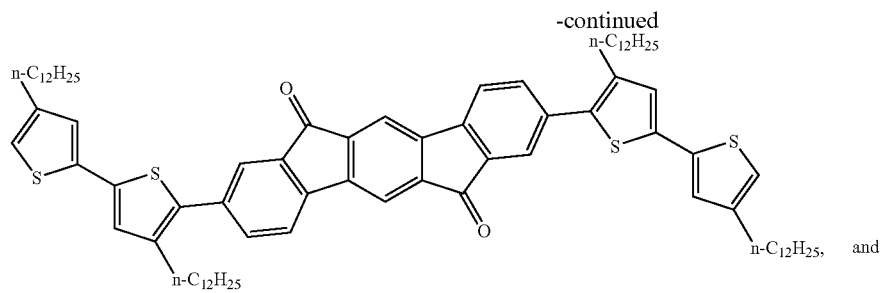

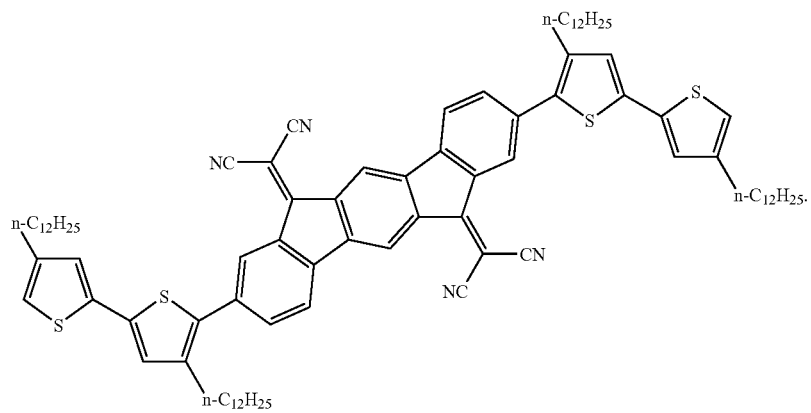

In another aspect, the present teachings provide polymerized products of one or more monomers, where at least one of the monomers can be a compound of formula I.

Accordingly, in various embodiments, the polymers can include a repeating unit of formula II' or formula II":

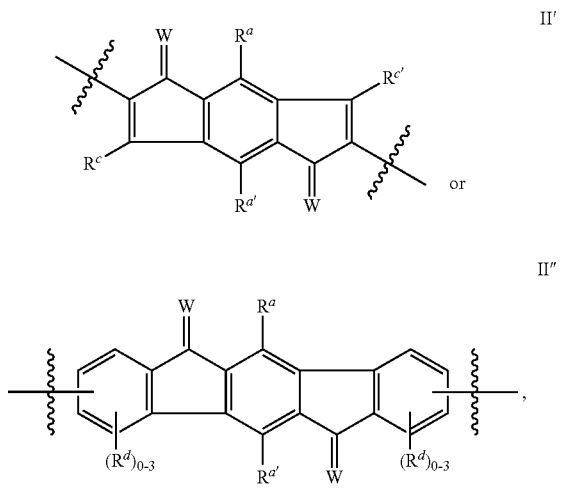

where $R^a$, $R^{a'}$, $R^c$, $R^{c'}$, $R^d$, and W are as defined herein.

In various embodiments of compounds of formula II' and formula II", $R^a$ and $R^{a'}$ independently can be H, a $C_{1-30}$ alkyl group, or a $C_{1-30}$ haloalkyl group. In some embodiments, $R^a$ and $R^{a'}$ independently can be H, a $C_{6-22}$ alkyl group, or a $C_{6-22}$ haloalkyl group. In certain embodiments, $R^a$ and $R^{a'}$, at each occurrence, independently can be selected from H, a hexyl group, a dodecyl group, and a docosyl group. In some embodiments, each of $R^c$ and $R^{c'}$ can be H.

In some embodiments, W can be O. In some embodiments, W can be $C(CN)_2$. In some embodiments, $R^d$, at each occurrence, independently can be selected from H, a hexyl group, a dodecyl group, and a docosyl group.

In various embodiments, the polymer can include one or more additional repeating units other than the repeating unit of formula II' or formula II". For example, the one or more additional repeating units independently can be selected from:

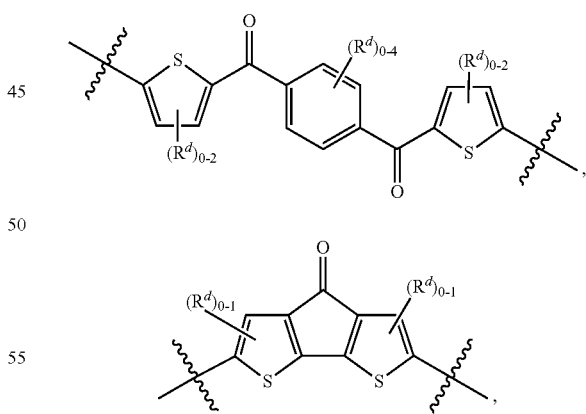

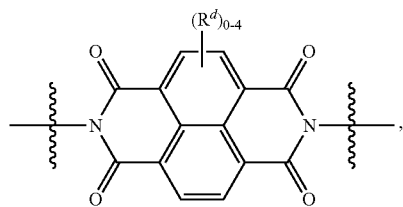

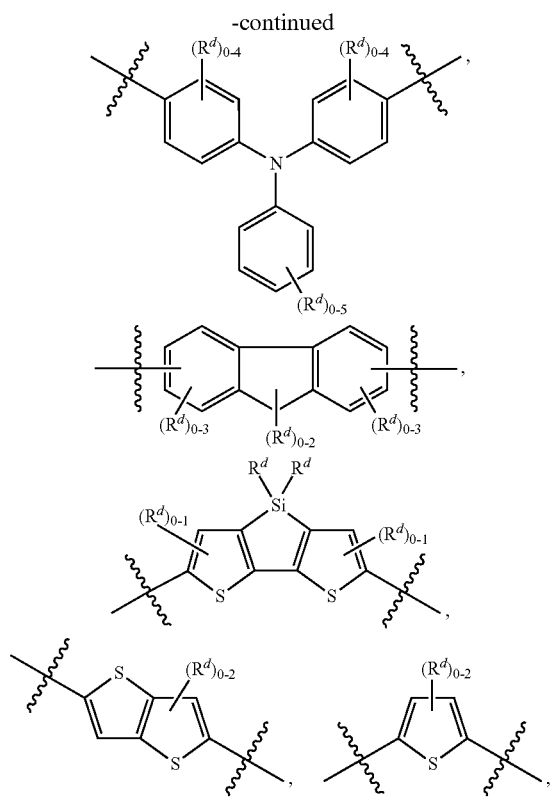
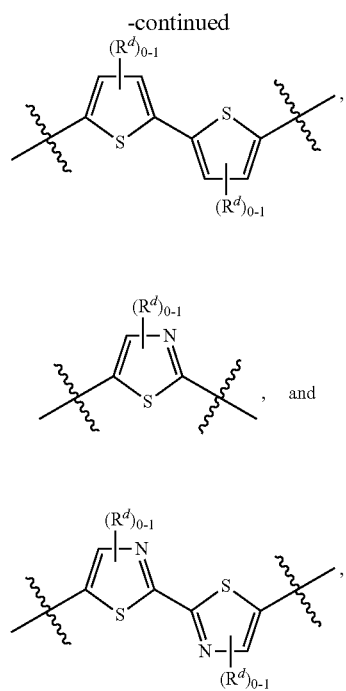
wherein $R^d$ is as defined herein.
Accordingly, in some embodiments, the polymers of the present teachings can have a formula selected from:
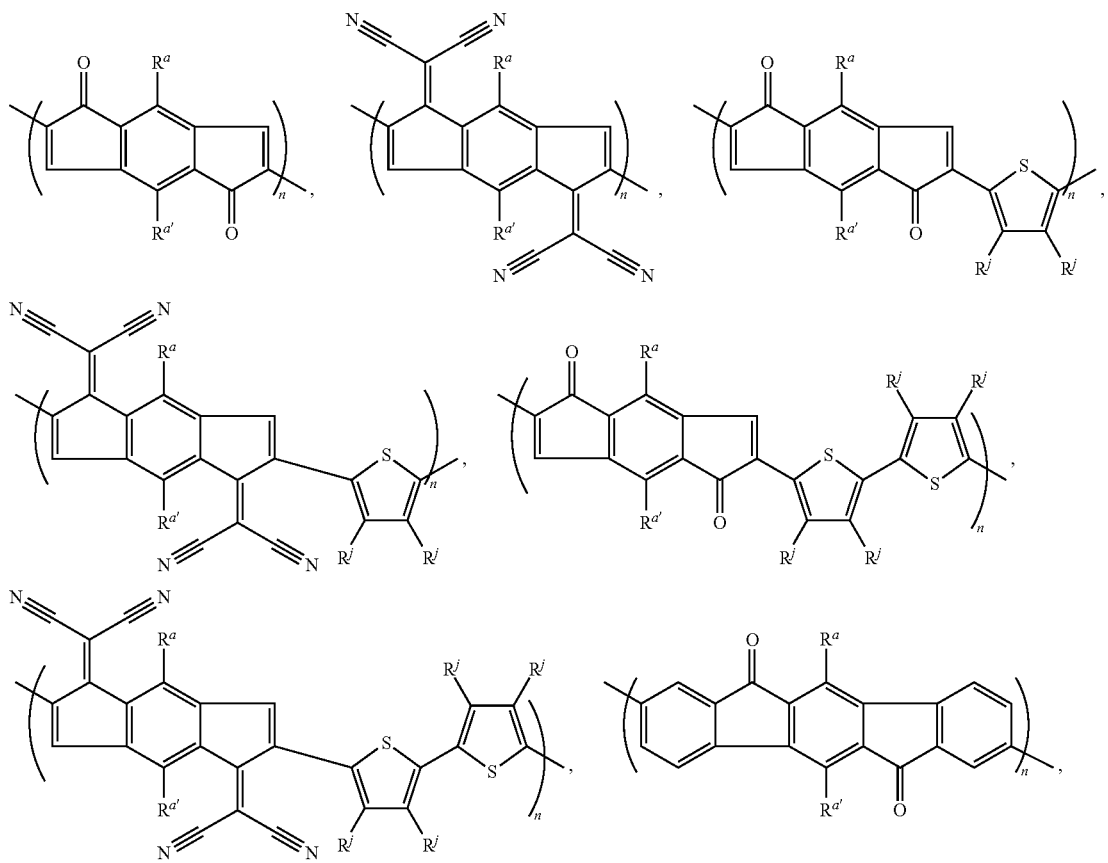

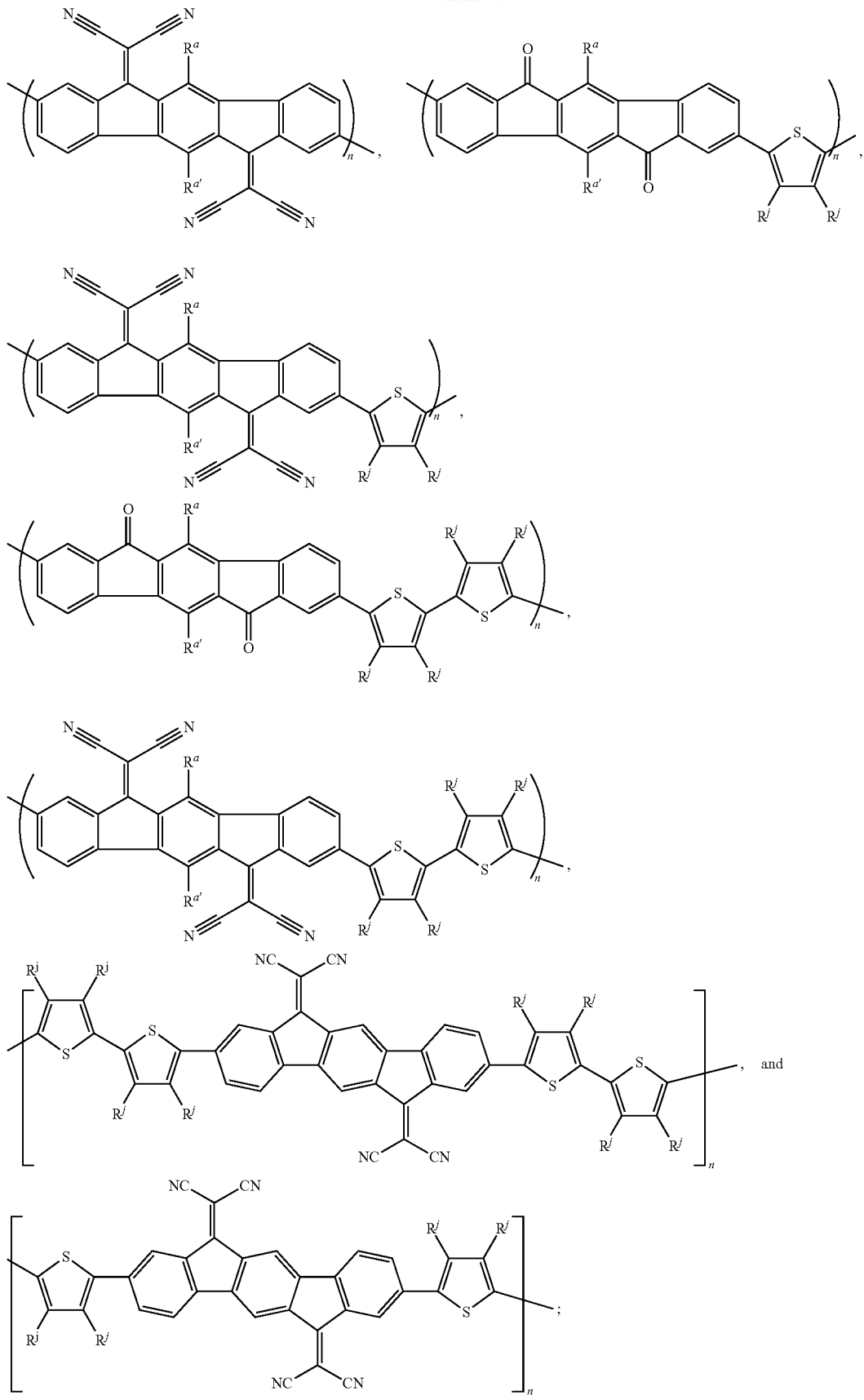

wherein $R^j$, at each occurrence, independently can be H or $R^i$; and $R^i$ is as defined herein; and n is an integer in the range of 5 to 100.

In another aspect, the present teachings provide compounds of formula III, formula IV, or formula V:

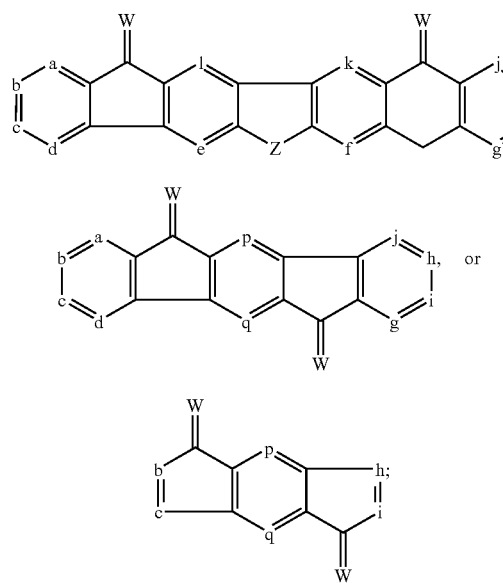

wherein:
a, d, e, f, g, j, k and l independently are $CR^1$, N, or P;
b, c, h and i independently are $CR^2$, N, or P;
p is $CR^3$;
q is $CR^4$;
W, at each occurrence, independently is O, S, $NR^1$, or $C(CN)_2$;
Y, at each occurrence, independently is a) a divalent $C_{1-10}$ alkyl group, b) a divalent $C_{2-10}$ alkenyl group, c) a divalent $C_{2-10}$ alkynyl group, d) a divalent $C_{1-10}$ haloalkyl group, or e) a covalent bond;
Z is $CR^3R^4$ or $SiR^3R^4$;
$R^1$, at each occurrence, independently is a) H, b) halogen, c) —CN, d) —$NO_2$, e) a $C_{1-30}$ alkyl group, f) a $C_{2-30}$ alkenyl group, g) a $C_{2-30}$ alkynyl group, h) a $C_{1-30}$ haloalkyl group, i) a —Y—$C_{3-14}$ cycloalkyl group, j) a —Y—$C_{6-14}$ aryl group, k) a —Y-3-14 membered cycloheteroalkyl group, or l) a —Y-5-14 membered heteroaryl group, wherein each of the $C_{1-30}$ alkyl group, the $C_{2-30}$ alkenyl group, the $C_{2-30}$ alkynyl group, the $C_{1-30}$ haloalkyl group, the $C_{3-14}$ cycloalkyl group, the $C_{6-14}$ aryl group, the 3-14 membered cycloheteroalkyl group, and the 5-14 membered heteroaryl group optionally is substituted with 1-5 $R^9$ groups;
$R^2$, at each occurrence, independently is a) H, b) halogen, c) —CN, d) —$NO_2$, e) —$OS(O)_2R^5$, f) —$Sn(R^5)_3$, g) —$B(OR^5)_2$, h) —Y—$R^6$, i) a $C_{1-30}$ alkyl group, j) a $C_{2-30}$ alkenyl group, k) a $C_{2-30}$ alkynyl group, or l) a $C_{1-30}$ haloalkyl group, wherein each of the $C_{1-30}$ alkyl group, the $C_{2-30}$ alkenyl group, the $C_{2-30}$ alkynyl group, and the $C_{1-30}$ haloalkyl group optionally is substituted with 1-5 $R^9$ groups;
$R^3$ and $R^4$ independently are a) a $C_{1-30}$ alkyl group, b) a $C_{2-30}$ alkenyl group, c) a $C_{2-30}$ alkynyl group, d) a $C_{1-30}$ haloalkyl group, e) a —Y—$C_{3-14}$ cycloalkyl group, f) a —Y—$C_{6-14}$ aryl group, g) a —Y-3-14 membered cycloheteroalkyl group, or h) a —Y-5-14 membered heteroaryl group, wherein each of the $C_{1-30}$ alkyl group, the $C_{2-30}$ alkenyl group, the $C_{2-30}$ alkynyl group, the $C_{1-30}$ haloalkyl group, the $C_{3-14}$ cycloalkyl group, the $C_{6-14}$ aryl group, the 3-14 membered cycloheteroalkyl group, and the 5-14 membered heteroaryl group optionally is substituted with 1-5 $R^9$ groups;
$R^5$, at each occurrence, independently is H or a $C_{1-30}$ alkyl group;
$R^6$, at each occurrence, independently is -(L)$_r$-$R^7$;
L, at each occurrence, independently is a) a divalent $C_{3-14}$ cycloalkyl group, b) a divalent $C_{6-14}$ aryl group, c) a divalent 3-14 cycloheteroalkyl group, or d) a divalent 5-14 membered heteroaryl group, wherein each of a)-d) optionally is substituted with 1-5 $R^9$ groups;
$R^7$, at each occurrence, is a) a $C_{3-14}$ cycloalkyl group, b) a $C_{6-14}$ aryl group, c) a 3-14 cycloheteroalkyl group, or d) a 5-14 membered heteroaryl group, wherein each of a)-d) optionally is substituted with 1-5 $R^8$ groups;
$R^8$, at each occurrence, independently is a) halogen, b) —CN, c) —$NO_2$, d) —$OS(O)_2R^5$, e) —$Sn(R^5)_3$, f) —$B(OR^5)_2$, g) a $C_{1-30}$ alkyl group, h) a $C_{2-30}$ alkenyl group, i) a $C_{2-30}$ alkynyl group, or j) a $C_{1-30}$ haloalkyl group, wherein each of the $C_{1-30}$ alkyl group, the $C_{2-30}$ alkenyl group, the $C_{2-30}$ alkynyl group, and the $C_{1-30}$ haloalkyl group optionally is substituted with 1-5 $R^9$ groups;
$R^9$, at each occurrence, independently is a) halogen, b) —CN, e) —$NO_2$, f) —OH, g) —$NH_2$, h) —$OC_{1-10}$ alkyl, i) —NH($C_{1-10}$ alkyl), j) —N($C_{1-10}$ alkyl)$_2$, k) —CHO, l) —C(O)OH, m) —C(O)($C_{1-10}$ alkyl), n) —C(O)O($C_{1-10}$ alkyl), o) —C(O)$NH_2$, p) —C(O)NH($C_{1-10}$ alkyl), q) —C(O)N($C_{1-10}$ alkyl)$_2$, r) a $C_{1-30}$ alkyl group, s) a $C_{2-30}$ alkenyl group, t) a $C_{2-30}$ alkynyl group, u) a $C_{1-30}$ haloalkyl group, v) a $C_{3-14}$ cycloalkyl group, w) a $C_{6-14}$ aryl group, x) a 3-14 membered cycloheteroalkyl group, or y) a 5-14 membered heteroaryl group; and
r, at each occurrence, independently is 0, 1, 2, 3, 4, 5, or 6.

In various embodiments, W can be O. In various embodiments, W can be $C(CN)_2$.

In various embodiments, a, d, e, f, g, j, k and l independently can be $CR^1$. For example, each of a, d, e, f, g, j, k and l can be CH.

In various embodiments, b, c, h and i independently can be $CR^2$, where $R^2$, at each occurrence, independently can be selected from H, halogen, —$OS(O)_2R^5$, —$Sn(R^5)_3$, —$B(OR^5)_2$, and a —Y—$R^6$ group, where $R^5$, $R^6$, and Y are as defined herein. In some embodiments, Y can be a covalent bond. In some embodiments, each of c and h can be CH. In some embodiments, each of b and i can be C(Br). In some embodiments, each of b and i can be a -(L)$_r$-$R^7$ group, where r, L, and $R^7$ are as defined herein.

In various embodiments, r can be 0, 1, or 2. In various embodiments, L can be a divalent 3-14 membered cycloheteroalkyl group, a divalent $C_{6-14}$ aryl group, or a divalent 5-14 membered heteroaryl group, where each of the divalent 3-14 membered cycloheteroalkyl group, the divalent $C_{6-14}$ aryl group, and the divalent 5-14 membered heteroaryl group optionally can be substituted with 1-5 $R^9$ groups and $R^9$ is as defined herein. In some embodiments, L can be a divalent phenyl group optionally substituted with 1-4 $R^9$ groups. In some embodiments, L can be a divalent thienyl group optionally substituted with 1-4 $R^9$ groups. In various embodiments, $R^7$ can be a 3-14 membered cycloheteroalkyl group, a $C_{6-14}$ aryl group, or a divalent 5-14 membered heteroaryl group, where each of the 3-14 membered cycloheteroalkyl group, the $C_{6-14}$ aryl group, and the 5-14 membered heteroaryl group optionally can be substituted with 1-5 $R^8$ groups and $R^8$ is as defined herein. In some embodiments, $R^7$ can be a phenyl group optionally substituted with 1-5 $R^8$ groups. In some embodiments, $R^7$ can be a thienyl group optionally substituted with 1-4 $R^8$ groups.

In various embodiments of formula III, Z can be $CR^3R^4$, where each of $R^3$ and $R^4$ independently can be a $C_{1-30}$ alkyl group, a $C_{2-30}$ alkenyl group, a $C_{2-30}$ alkynyl group, a $C_{1-30}$ haloalkyl group, a —($C_{1-10}$ alkyl)-$C_{3-14}$ cycloalkyl group, a —($C_{1-10}$ alkyl)-$C_{6-14}$ aryl group, a —($C_{1-10}$ alkyl)-3-14 membered cycloheteroalkyl group, or a —($C_{1-10}$ alkyl)-5-14 membered heteroaryl group, where each of the $C_{1-30}$ alkyl group, the $C_{2-30}$ alkenyl group, the $C_{2-30}$ alkynyl group, the $C_{3-14}$ cycloalkyl group, the $C_{6-14}$ aryl group, the 3-14 membered cycloheteroalkyl group, and the 5-14 membered heteroaryl group can be optionally substituted with 1-5 $R^9$ groups (e.g., 1-5 halogens). In some embodiments, each of $R^3$ and $R^4$ independently can be a $C_{6-20}$ alkyl group, a $C_{6-20}$ alkenyl group, a $C_{6-20}$ alkynyl group, or a $C_{6-20}$ haloalkyl group. In certain embodiments, each of $R^3$ and $R^4$ independently can be a $C_{6-20}$ alkyl group or a $C_{6-20}$ haloalkyl group. In certain embodiments, each of $R^3$ and $R^4$ independently can be a $C_{1-20}$ alkyl group or a $C_{2-20}$ alkenyl group, including a straight chain or branched $C_{6-20}$ alkyl or $C_{6-20}$ alkenyl group. For example, each of $R^3$ and $R^4$ independently can be:

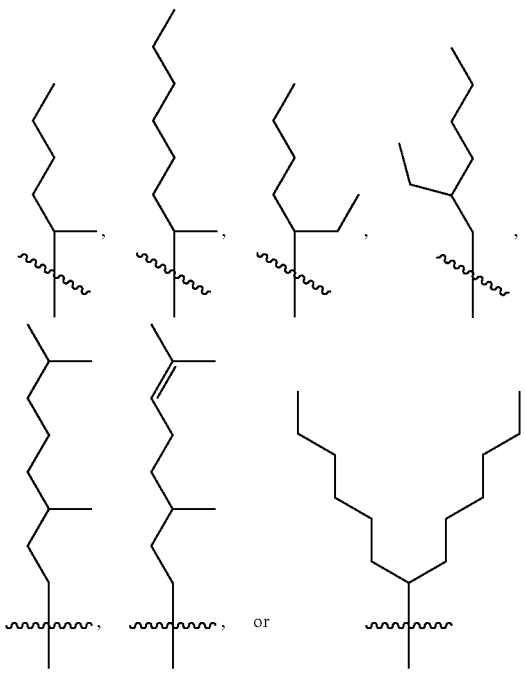

In various embodiments of compounds of formula IV or formula V, each of p and q independently can be a $C(C_{1-30}$ alkyl) group, a $C(C_{2-30}$ alkenyl) group, a $C(C_{2-30}$ alkynyl) group, a $C(C_{1-30}$ haloalkyl) group, a $C(—C_{1-10}$ alkyl-$C_{3-14}$ cycloalkyl) group, a $C(—C_{1-10}$ alkyl-$C_{6-14}$ aryl) group, a $C(—C_{1-10}$ alkyl-3-14 membered cycloheteroalkyl) group, or a $C(—C_{1-10}$ alkyl-5-14 membered heteroaryl) group, where each of the $C_{1-30}$ alkyl group, the $C_{2-30}$ alkenyl group, the $C_{2-30}$ alkynyl group, the $C_{3-14}$ cycloalkyl group, the $C_{6-14}$ aryl group, the 3-14 membered cycloheteroalkyl group, and the 5-14 membered heteroaryl group optionally can be substituted with 1-5 $R^9$ groups (e.g., 1-5 halogens). In some embodiments, each of p and q independently can be a $C(C_{6-20}$ alkyl) group, a $C(C_{6-20}$ alkenyl) group, a $C(C_{6-20}$ alkynyl) group, or a $C(C_{6-20}$ haloalkyl) group. For example, each of p and q independently can be a $C(C_{6-20}$ alkyl) group or a $C(C_{6-20}$ haloalkyl) group. In some embodiments, each of p and q independently can be a $C(C_{1-20}$ alkyl) group or a $C(C_{2-20}$ alkenyl) group, where the $C_{1-20}$ alkyl group and the $C_{2-20}$ alkenyl group can be, for example, a straight chain or branched $C_{6-20}$ alkyl or $C_{6-20}$ alkenyl group. In particular embodiments, each of the straight chain or branched $C_{6-20}$ alkyl and $C_{6-20}$ alkenyl groups can be:

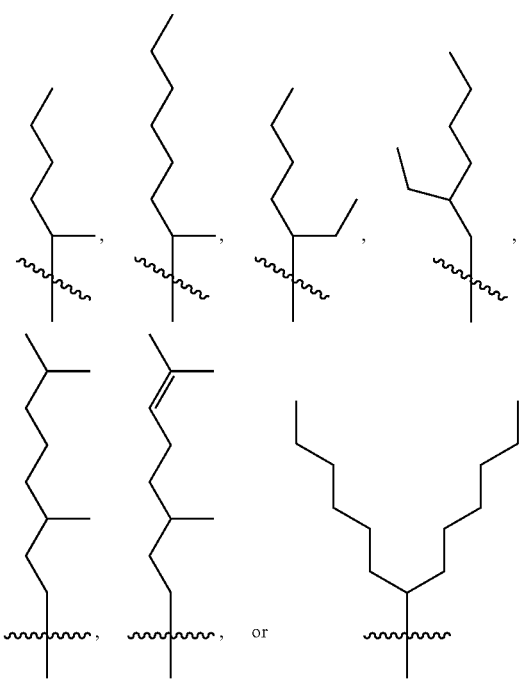

Exemplary compounds of formula III, formula IV and formula V include:

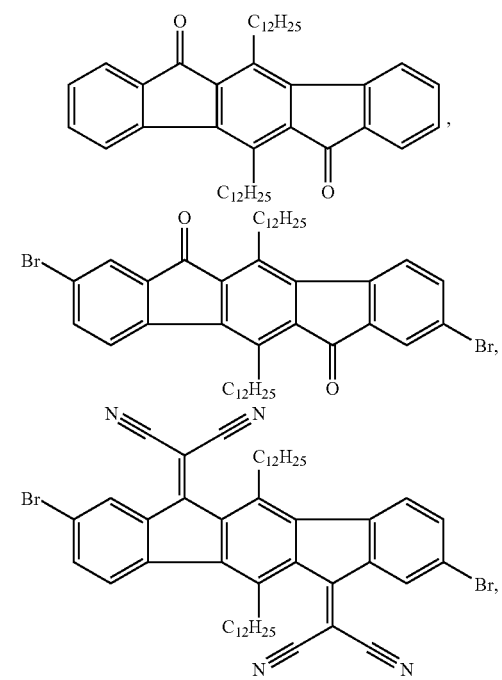

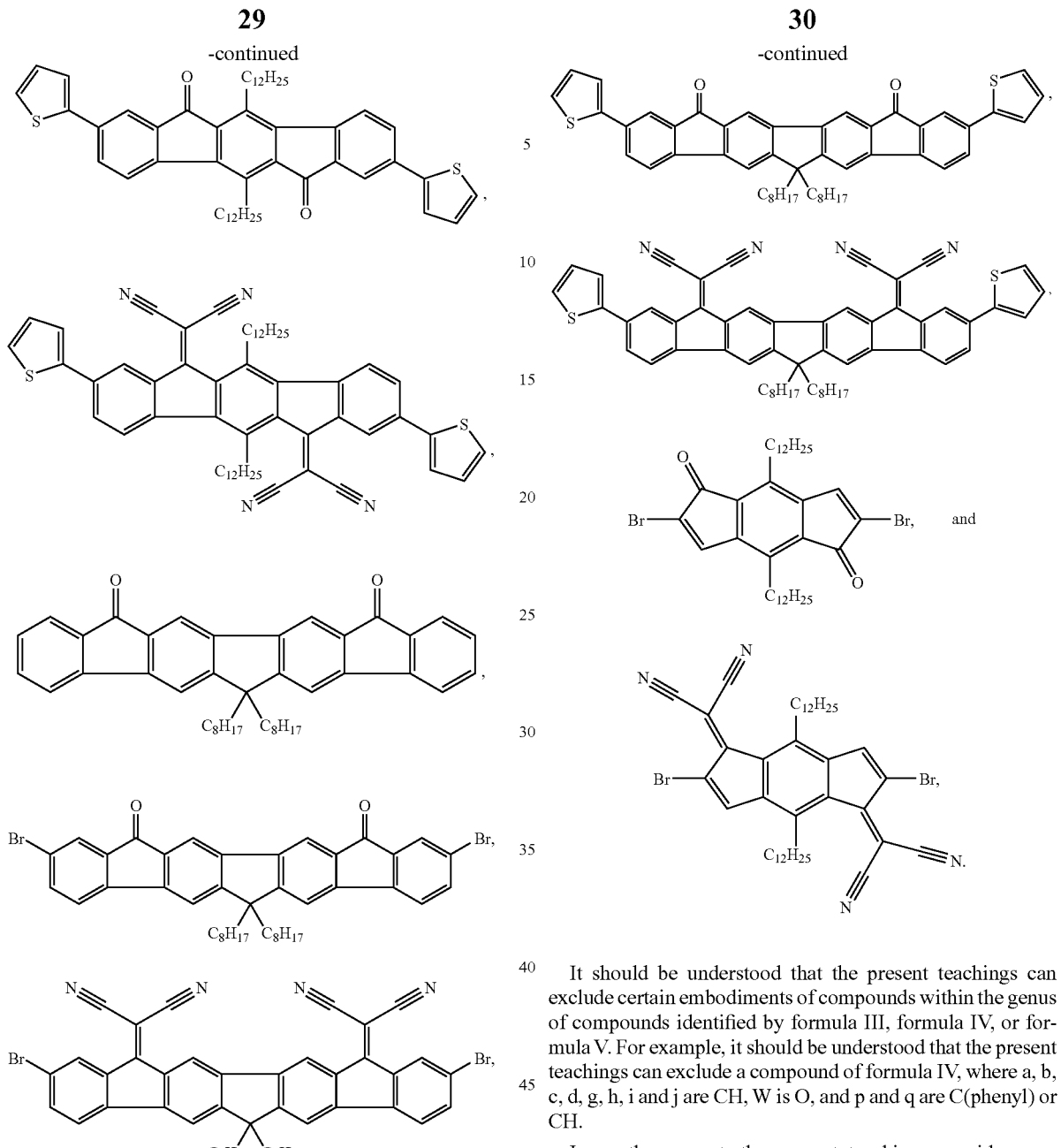

It should be understood that the present teachings can exclude certain embodiments of compounds within the genus of compounds identified by formula III, formula IV, or formula V. For example, it should be understood that the present teachings can exclude a compound of formula IV, where a, b, c, d, g, h, i and j are CH, W is O, and p and q are C(phenyl) or CH.

In another aspect, the present teachings provide compounds of formula VII, formula VIII, and formula IX:

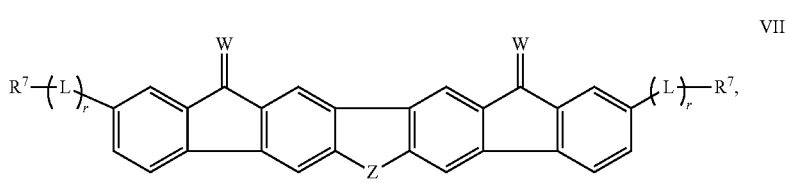

VII

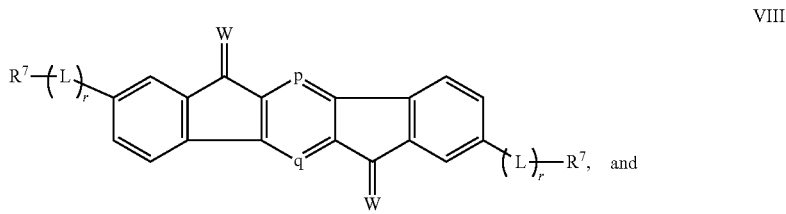

VIII

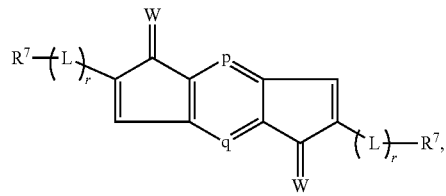

wherein:
p is CR$^{3'}$;
q is CR$^{4'}$;
Z is a) CR$^{3'}$R$^{4'}$, b) SiR$^{3'}$R$^{4'}$, c) C(O), d) C(S), e) C(NR$^5$), or f) C(CR$^1$R$^1$);
R$^{3'}$ and R$^{4'}$ independently are a) H, b) a C$_{1-30}$ alkyl group, c) a C$_{2-30}$ alkenyl group, d) a C$_{2-30}$ alkynyl group, e) a C$_{1-30}$ haloalkyl group, f) a —Y—C$_{3-14}$ cycloalkyl group, g) a —Y—C$_{6-14}$ aryl group, h) a —Y-3-14 membered cycloheteroalkyl group, or i) a —Y-5-14 membered heteroaryl group, wherein each of the C$_{1-30}$ alkyl group, the C$_{2-30}$ alkenyl group, the C$_{2-30}$ alkynyl group, the C$_{1-30}$ haloalkyl group, the C$_{3-14}$ cycloalkyl group, the C$_{6-14}$ aryl group, the 3-14 membered cycloheteroalkyl group, and the 5-14 membered heteroaryl group optionally is substituted with 1-5 R$^9$ groups; and
R$^1$, R$^5$, R$^7$, R$^9$, r, L, W, and Y are as defined herein.

In various embodiments of formula VII, Z can be CR$^{3'}$R$^{4'}$, where each of R$^{3'}$ and R$^{4'}$ independently can be H, a C$_{1-30}$ alkyl group, a C$_{2-30}$ alkenyl group, a C$_{2-30}$ alkynyl group, a C$_{1-30}$ haloalkyl group, a —(C$_{1-10}$ alkyl)-C$_{3-14}$ cycloalkyl group, a —(C$_{1-10}$ alkyl)-C$_{6-14}$ aryl group, a —(C$_{1-10}$ alkyl)-3-14 membered cycloheteroalkyl group, or a —(C$_{1-10}$ alkyl)-5-14 membered heteroaryl group, where each of the C$_{1-30}$ alkyl group, the C$_{2-30}$ alkenyl group, the C$_{2-30}$ alkynyl group, the C$_{3-14}$ cycloalkyl group, the C$_{6-14}$ aryl group, the 3-14 membered cycloheteroalkyl group, and the 5-14 membered heteroaryl group can be optionally substituted with 1-5 R$^9$ groups and R$^9$ is as defined herein. In some embodiments, each of R$^{3'}$ and R$^{4'}$ independently can be H, a C$_{1-30}$ alkyl group, a C$_{2-30}$ alkenyl group, a C$_{2-30}$ alkynyl group, or a C$_{1-30}$ haloalkyl group. In certain embodiments, each of R$^{3'}$ and R$^{4'}$ independently can be H, a C$_{1-30}$ alkyl group or a C$_{1-30}$ haloalkyl group. In particular embodiments, each of R$^{3'}$ and R$^{4'}$ independently can be H.

In various embodiments of formula VIII or formula IX, each of p and q independently can be C(R$^{3'}$) or C(R$^{4'}$), where R$^{3'}$ and R$^{4'}$ independently can be H, a C$_{1-30}$ alkyl group, a C$_{2-30}$ alkenyl group, a C$_{2-30}$ alkynyl group, a C$_{1-30}$ haloalkyl group, a —C$_{1-10}$ alkyl-C$_{3-14}$ cycloalkyl group, a —C$_{1-10}$ alkyl-C$_{6-14}$ aryl group, a —C$_{1-10}$ alkyl-3-14 membered cycloheteroalkyl group, or a —C$_{1-10}$ alkyl-5-14 membered heteroaryl, where each of the C$_{1-30}$ alkyl group, the C$_{2-30}$ alkenyl group, the C$_{2-30}$ alkynyl group, the C$_{3-14}$ cycloalkyl group, the C$_{6-14}$ aryl group, the 3-14 membered cycloheteroalkyl group, and the 5-14 membered heteroaryl group optionally can be substituted with 1-5 R$^9$ groups and R$^9$ is as defined herein. In some embodiments, each of p and q independently can be CH, a C(C$_{1-30}$ alkyl) group, a C(C$_{2-30}$ alkenyl) group, a C(C$_{2-30}$ alkynyl) group, or a C(C$_{1-30}$ haloalkyl) group. In certain embodiments, each of p and q independently can be CH, a C(C$_{1-30}$ alkyl) group or a C(C$_{1-30}$ haloalkyl) group. In particular embodiment, each of p and q can be CH.

In some embodiments, the compounds of formula VII, formula VIII, or formula IX can be selected from:

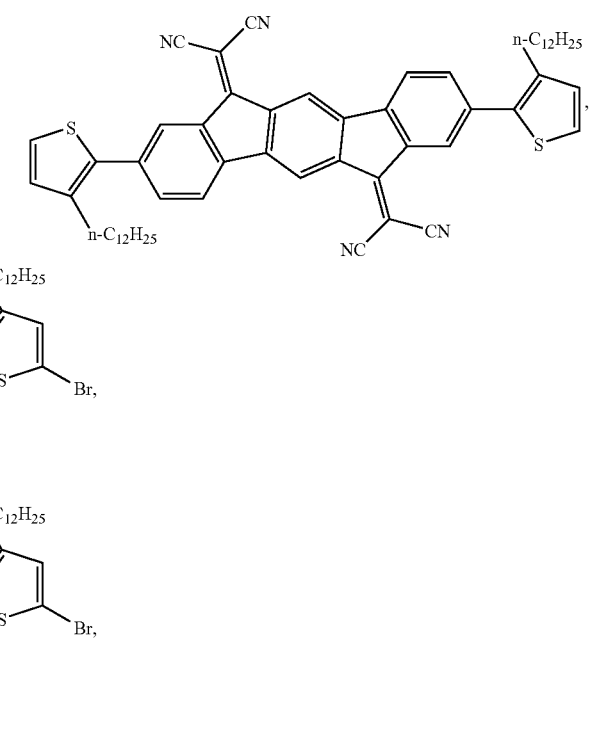

-continued

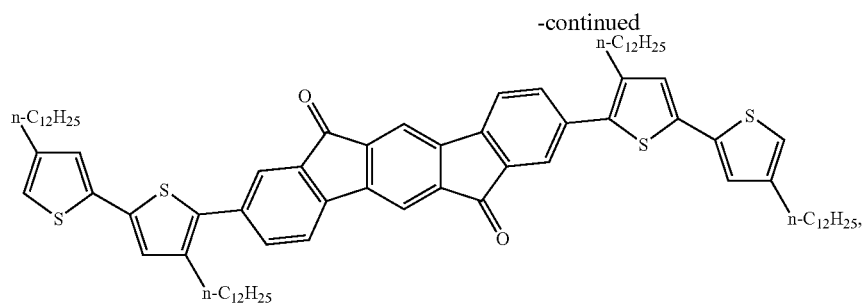

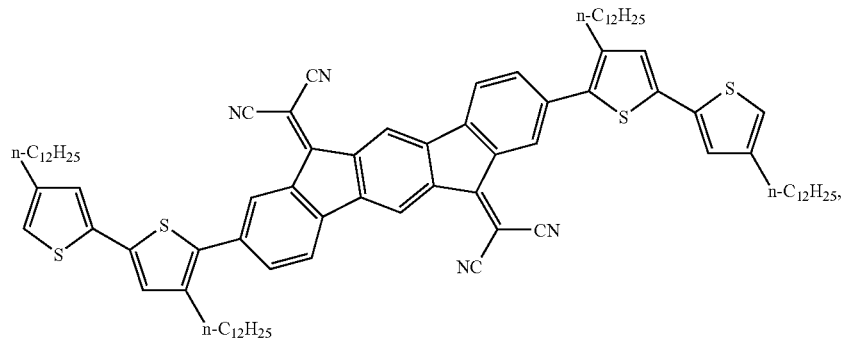

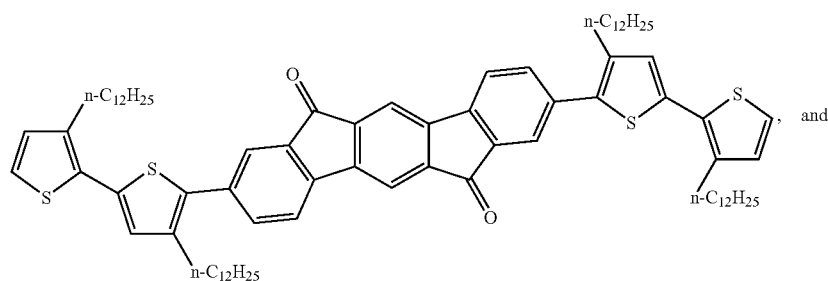, and

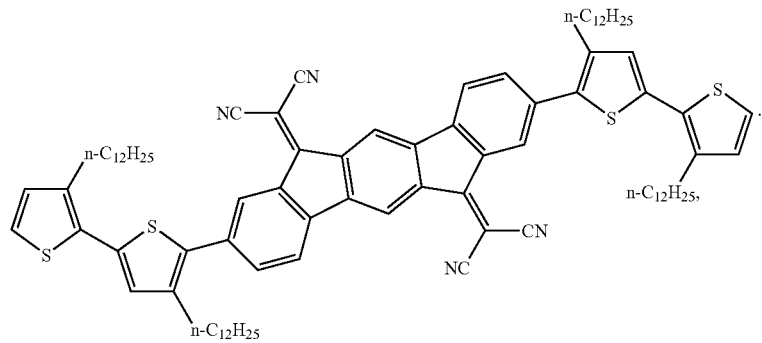.

In another aspect, the present teachings provide polymerized products of one or more monomers, where at least one of the monomers can be a compound of formula III, formula IV, formula V, formula VII, formula VIII, or formula IX.

Accordingly, in various embodiments, the polymers can include a repeating unit of formula VI:

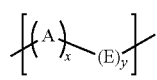

VI wherein:

A, at each occurrence, independently has formula III', formula IV', or formula V':

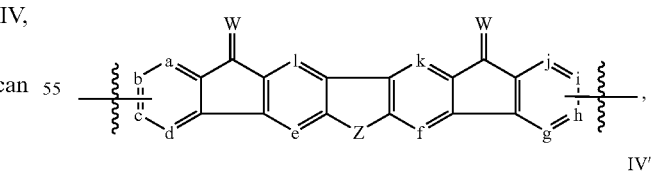

III'

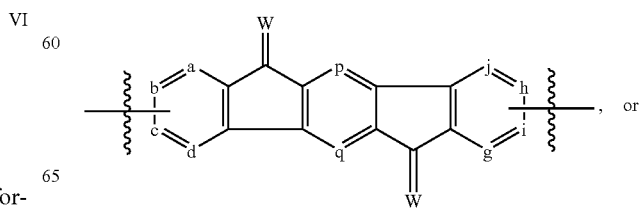

IV'

, or

-continued

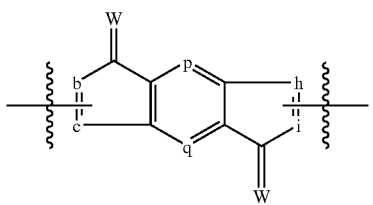
V'

E, at each occurrence, independently is a divalent $C_{6-14}$ aryl group or a divalent 5-14 membered heteroaryl group, each of which optionally is substituted with 1-5 $R^9$ groups;
x is 1, 2, 3, 4, 5, 6, 7, 8, 9, or 10; and
y is 0, 1, 2, 3, 4, 5, 6, 7, 8, 9, and 10;
wherein:
a, b, c, d, e, f, g, h, i, j, k, and l independently are $CR^1$, N, or P, provided that one of b and c and one of h and i are C⁃;
p is $CR^3$;
q is $CR^4$;
W, at each occurrence, independently is O, S, or $C(CN)_2$;
Y, at each occurrence, independently is a) a divalent $C_{1-10}$ alkyl group, b) a divalent $C_{2-10}$ alkenyl group, c) a divalent $C_{2-10}$ alkynyl group, d) a divalent $C_{1-10}$ haloalkyl group, or e) a covalent bond;
Z is a) $CR^{3'}R^{4'}$, b) $SiR^{3'}R^{4'}$, c) C(O), d) C(S), e) $C(NR^5)$, or f) $C(CR^1R^1)$;
$R^1$, at each occurrence, independently is a) H, b) halogen, c) —CN, d) —NO$_2$, e) a $C_{1-30}$ alkyl group, f) a $C_{2-30}$ alkenyl group, g) a $C_{2-30}$ alkynyl group, h) a $C_{1-30}$ haloalkyl group, i) a —Y—$C_{3-14}$ cycloalkyl group, j) a —Y—$C_{6-14}$ aryl group, k) a —Y-3-14 membered cycloheteroalkyl group, or l) a —Y-5-14 membered heteroaryl group, wherein each of the $C_{1-30}$ alkyl group, the $C_{2-30}$ alkenyl group, the $C_{2-30}$ alkynyl group, the $C_{1-30}$ haloalkyl group, the $C_{3-14}$ cycloalkyl group, the $C_{6-14}$ aryl group, the 3-14 membered cycloheteroalkyl group, and the 5-14 membered heteroaryl group optionally is substituted with 1-5 $R^9$ groups;

$R^{3'}$ and $R^{4'}$ independently are a) H, b) a $C_{1-30}$ alkyl group, c) a $C_{2-30}$ alkenyl group, d) a $C_{2-30}$ alkynyl group, e) a $C_{1-30}$ haloalkyl group, f) a —Y—$C_{3-14}$ cycloalkyl group, g) a —Y—$C_{6-14}$ aryl group, h) a —Y-3-14 membered cycloheteroalkyl group, or i) a —Y-5-14 membered heteroaryl group, wherein each of the $C_{1-30}$ alkyl group, the $C_{2-30}$ alkenyl group, the $C_{2-30}$ alkynyl group, the $C_{1-30}$ haloalkyl group, the $C_{3-14}$ cycloalkyl group, the $C_{6-14}$ aryl group, the 3-14 membered cycloheteroalkyl group, and the 5-14 membered heteroaryl group optionally is substituted with 1-5 $R^9$ groups;
$R^5$, at each occurrence, independently is H or a $C_{1-30}$ alkyl group; and
$R^9$, at each occurrence, independently is a) halogen, b) —CN, e) —NO$_2$, f) —OH, g) —NH$_2$, h) —OC$_{1-10}$ alkyl, i) —NH($C_{1-10}$ alkyl), j) —N($C_{1-10}$ alkyl)$_2$, k) —CHO, l) —C(O)OH, m) —C(O)($C_{1-10}$ alkyl), n) —C(O)O($C_{1-10}$ alkyl), o) —C(O)NH$_2$, p) —C(O)NH($C_{1-10}$ alkyl), q) —C(O)N($C_{1-10}$ alkyl)$_2$, r) a $C_{1-30}$ alkyl group, s) a $C_{2-30}$ alkenyl group, t) a $C_{2-30}$ alkynyl group, u) a $C_{1-30}$ haloalkyl group, v) a $C_{3-14}$ cycloalkyl group, w) a $C_{6-14}$ aryl group, x) a 3-14 membered cycloheteroalkyl group, or y) a 5-14 membered heteroaryl group.

In some embodiments, A, at each occurrence, can have formula III″, formula IV″, or formula V″:

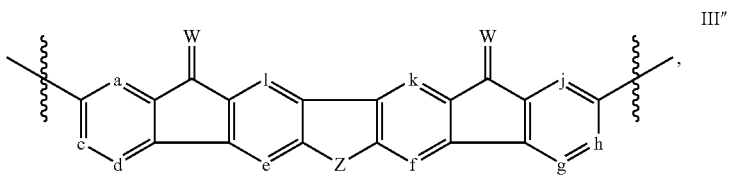
III″

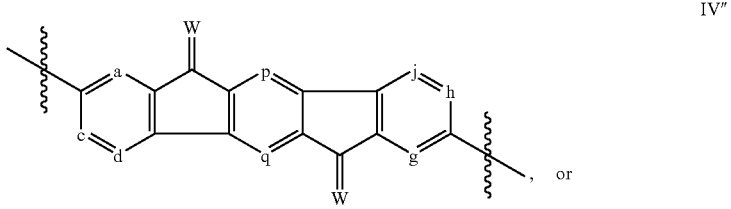
IV″, or

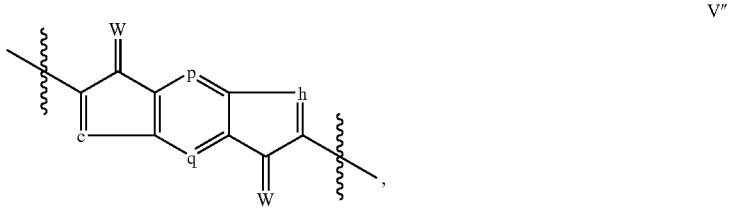
V″ where a, c, d, e, f, g, h, j, k, l, p, q, W, and Z are as defined herein.

In various embodiments, W can be O or $C(CN)_2$. In some embodiments, a, c, d, e, f, g, h, j, k and l independently can be $CR^1$. For example, each of a, c, d, e, f, g, h, j, k and l can be CH.

In some embodiments of formula III″, Z can be C(O) or $CR^{3'}R^{4'}$, where each of $R^{3'}$ and $R^{4'}$ independently can be H, a $C_{1-30}$ alkyl group, a $C_{2-30}$ alkenyl group, a $C_{2-30}$ alkynyl group, a $C_{1-30}$ haloalkyl group, a —($C_{1-10}$ alkyl)-$C_{3-14}$ cycloalkyl group, a —($C_{1-10}$ alkyl)-$C_{6-14}$ aryl group, a —($C_{1-10}$ alkyl)-3-14 membered cycloheteroalkyl group, or a —($C_{1-10}$ alkyl)-5-14 membered heteroaryl group, where each of the $C_{1-30}$ alkyl group, the $C_{2-30}$ alkenyl group, the $C_{2-30}$ alkynyl group, the $C_{3-14}$ cycloalkyl group, the $C_{6-14}$ aryl group, the 3-14 membered cycloheteroalkyl group, and the 5-14 membered heteroaryl group optionally can be substituted with 1-5 $R^9$ groups (e.g., 1-5 halogens). In certain embodiments, each of $R^{3'}$ and $R^{4'}$ independently can be H, a $C_{1-30}$ alkyl group, a $C_{2-30}$ alkenyl group, a $C_{2-30}$ alkynyl group, or a $C_{1-30}$ haloalkyl group. In particular embodiments, each of $R^{3'}$ and $R^{4'}$ independently can be H, a $C_{1-30}$ alkyl group, or a $C_{1-30}$ haloalkyl group, for example, a $C_{6-20}$ alkyl group or a $C_{6-20}$ haloalkyl group.

In some embodiments of formula IV" or formula V", each of p and q independently can be CH, a C($C_{1-30}$ alkyl) group, a C($C_{2-30}$ alkenyl) group, a C($C_{2-30}$ alkynyl) group, a C($C_{1-30}$ haloalkyl) group, a C(—$C_{1-10}$ alkyl-$C_{3-14}$ cycloalkyl) group, a C(—$C_{1-10}$ alkyl-$C_{6-14}$ aryl) group, a C(—$C_{1-10}$ alkyl-3-14 membered cycloheteroalkyl) group, or a C(—$C_{1-10}$ alkyl-5-14 membered heteroaryl) group, where each of the $C_{1-30}$ alkyl group, the $C_{2-30}$ alkenyl group, the $C_{2-30}$ alkynyl group, the $C_{3-14}$ cycloalkyl group, the $C_{6-14}$ aryl group, the 3-14 membered cycloheteroalkyl group, and the 5-14 membered heteroaryl group optionally can be substituted with 1-5 $R^9$ groups (e.g., 1-5 halogens). In certain embodiments, each of p and q independently can be CH, a C($C_{1-30}$ alkyl) group, a C($C_{2-30}$ alkenyl) group, a C($C_{2-30}$ alkynyl) group, or a C($C_{1-30}$ haloalkyl) group. In particular embodiments, each of p and q independently can be CH, a C($C_{1-30}$ alkyl) group, or a C($C_{1-30}$ alkyl) group, for example, a C($C_{6-20}$ alkyl) group or a C($C_{6-20}$ haloalkyl) group.

In some embodiments, E can be a divalent phenyl group optionally substituted with 1-5 $R^9$ groups or a divalent 5-membered heteroaryl group optionally substituted with 1-4 $R^9$ groups, where $R^9$ is as defined herein. In certain embodiments, E can be a divalent thienyl group optionally substituted with 1-2 $R^9$ groups, where $R^9$ is as defined herein.

In some embodiments, $R^9$ independently can be selected from halogen, —CN, —$NO_2$, a $C_{1-30}$ alkyl group, a $C_{2-30}$ alkenyl group, a $C_{2-30}$ alkynyl group, a $C_{1-30}$ haloalkyl group, and a $C_{3-14}$ cycloalkyl group. For example, $R^9$ independently can be selected from halogen, —CN, —$NO_2$, a $C_{1-30}$ alkyl group, or a $C_{1-30}$ haloalkyl group. In certain embodiments, the $C_{1-30}$ alkyl group can be a hexyl group, a dodecyl group, or a docosyl group.

In some embodiments, x can be 1, 2, 3, 4, and 5; and y can be 0, 1, 2, 3, 4, and 5. In certain embodiments, x can be 1, and y can be 0, 1 or 2.

Accordingly, in various embodiments, the polymers can have formula VI':

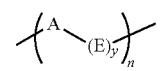

wherein n is an integer in the range of 5 to 100; and A, E, and y are as defined herein.

In some embodiments, the polymers can have formula III''', formula IV''', or formula V''':

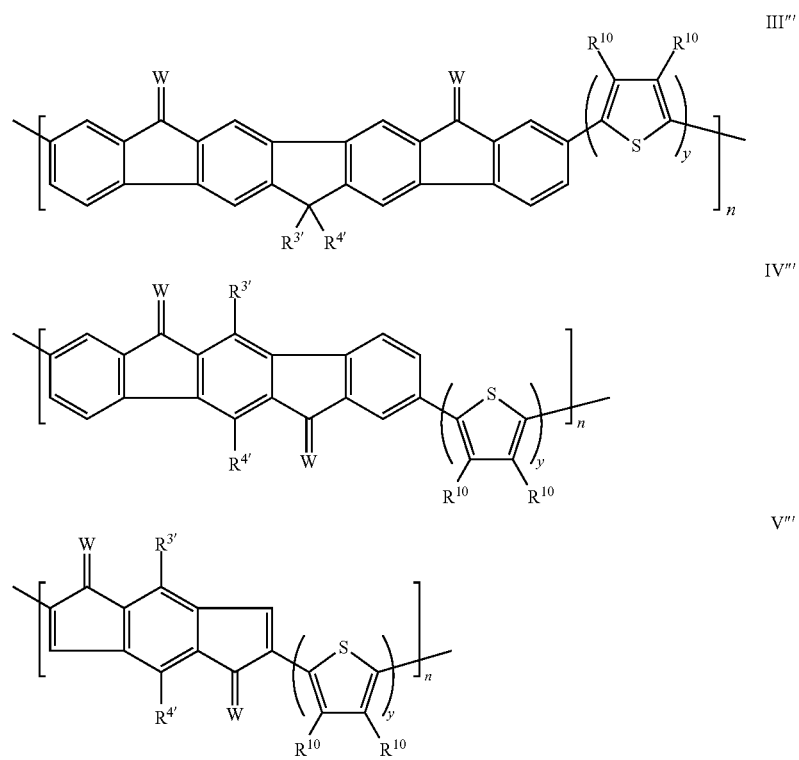

wherein $R^{10}$, at each occurrence, independently is H or $R^9$, and n is an integer in the range of 5 to 100; and $R^{3'}$, $R^{4'}$, $R^9$, W and y are as defined herein.

More specifically, the polymers can have a formula selected from:

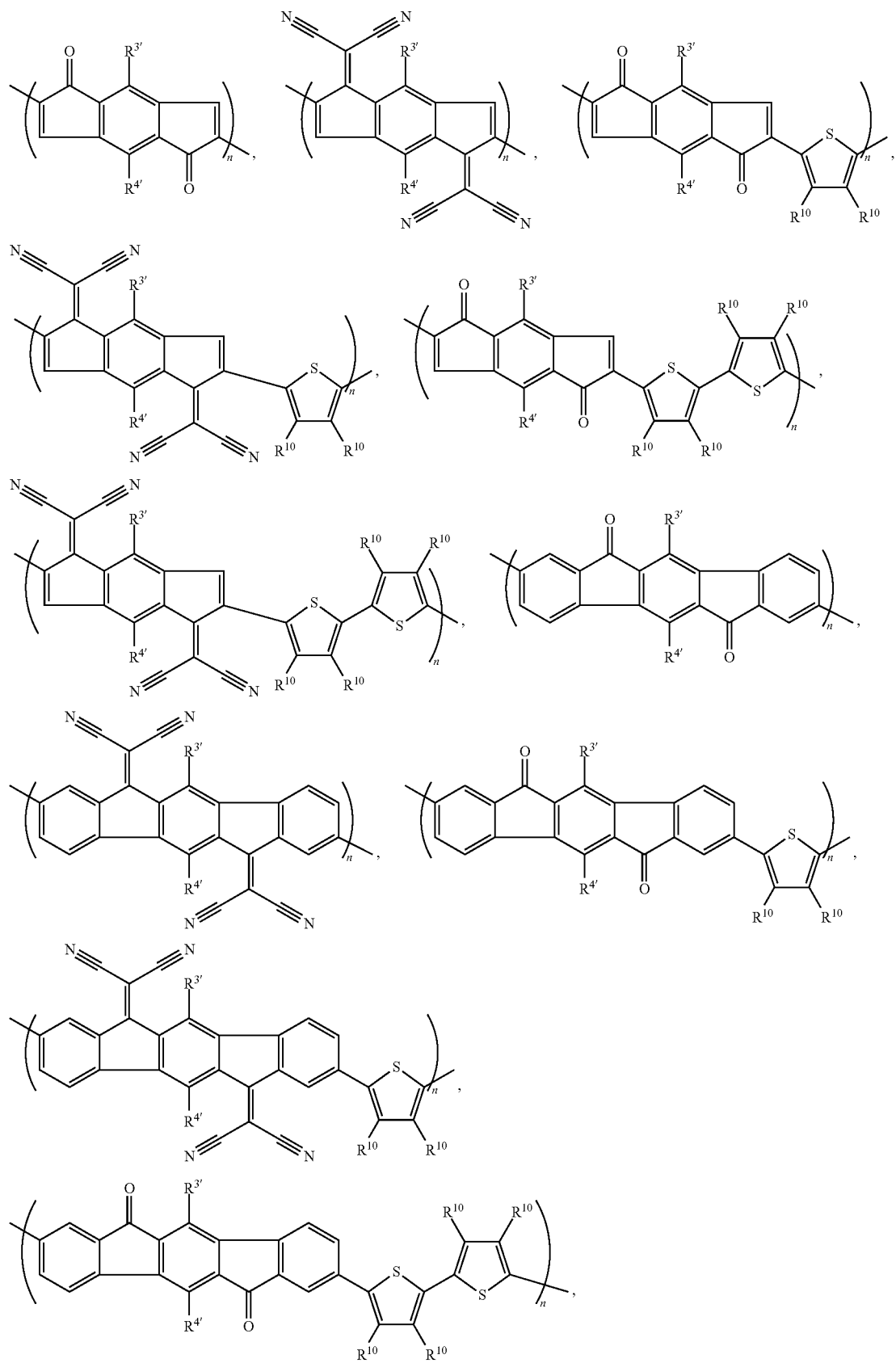

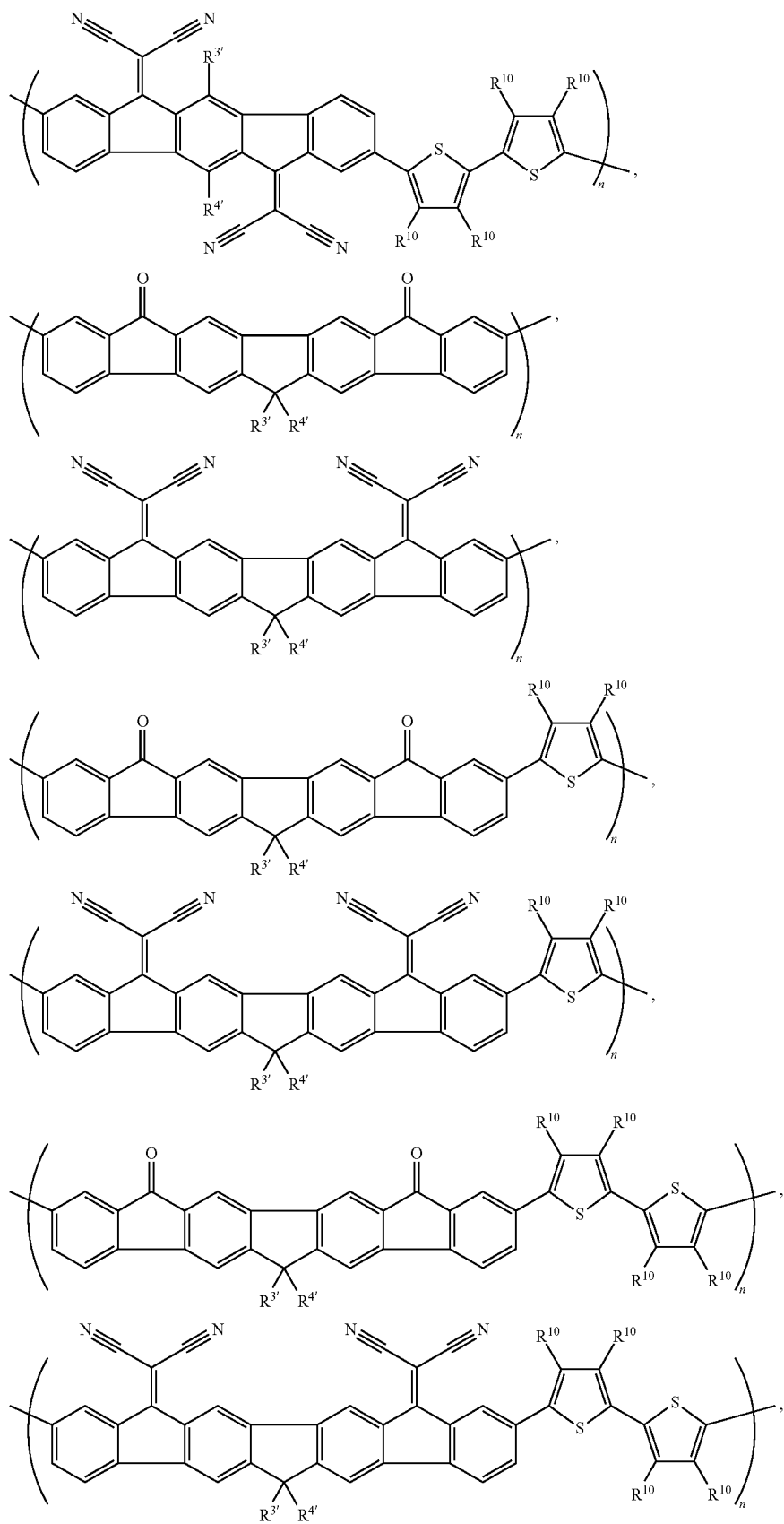

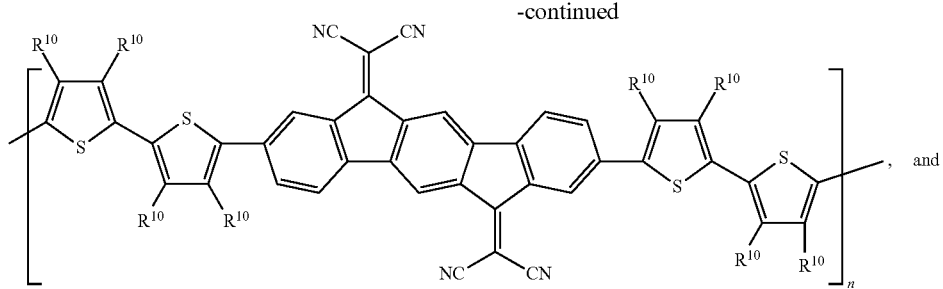

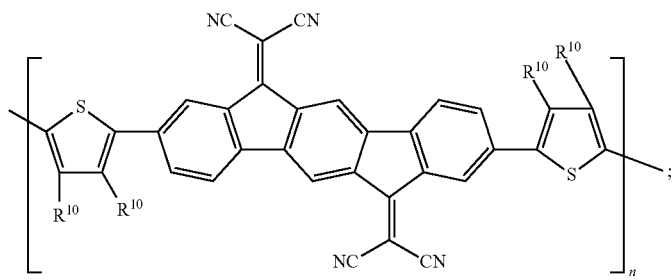

where $R^{10}$, at each occurrence, independently can be H or $R^9$; n is an integer in the range of 5 to 100; and $R^{3'}$, $R^{4'}$, and $R^9$ is as defined herein.

The polymers described above optionally can include one or more additional repeating units other than the repeating unit of formula VI or formula VI'. For example, the one or more additional repeating units can be selected from various moieties (e.g., conjugated moieties) known in the art that exhibit semiconducting activity. In certain embodiments, the one or more additional repeating units can be selected from:

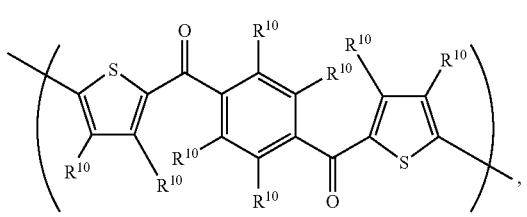

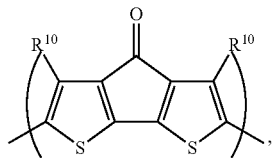

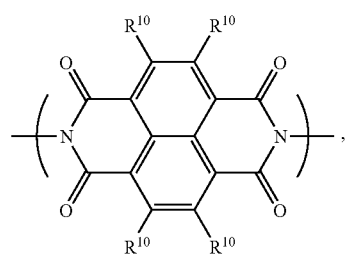

-continued

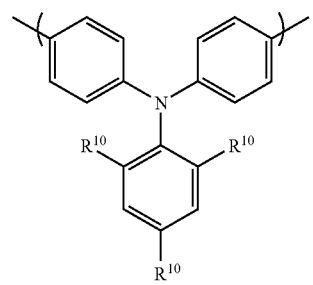

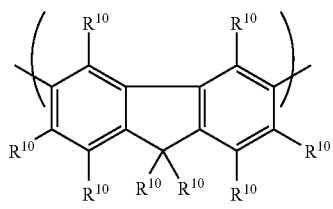

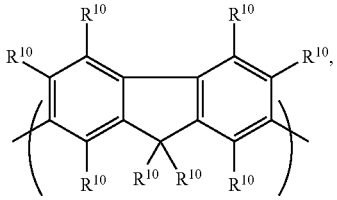

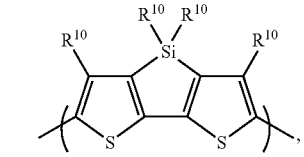

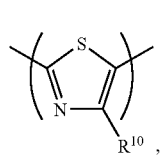

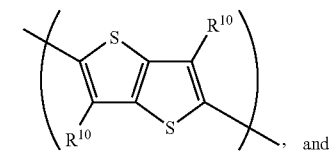

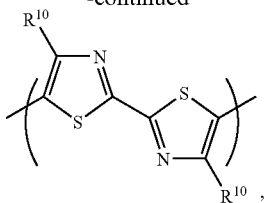
where $R^{10}$, at each occurrence, independently can be H or $R^9$, and $R^9$ is as defined herein. In particular embodiments, the one or more additional repeating units can be selected from:
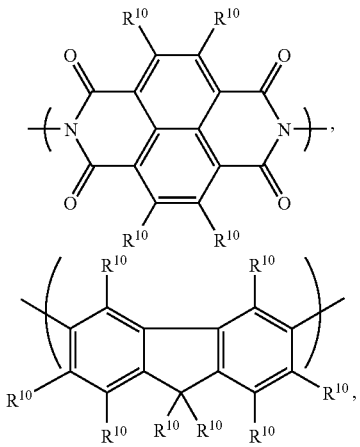
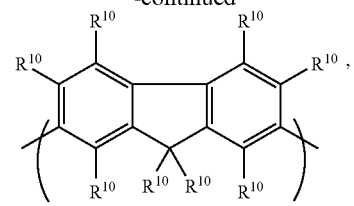
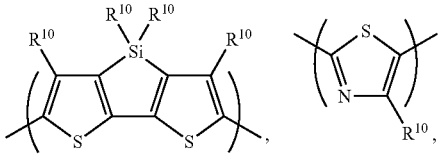
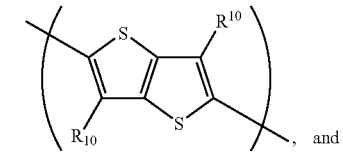
, and
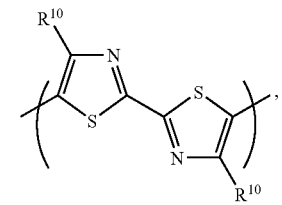
where $R^{10}$ is as defined herein.
Exemplary polymers of the present teachings include:
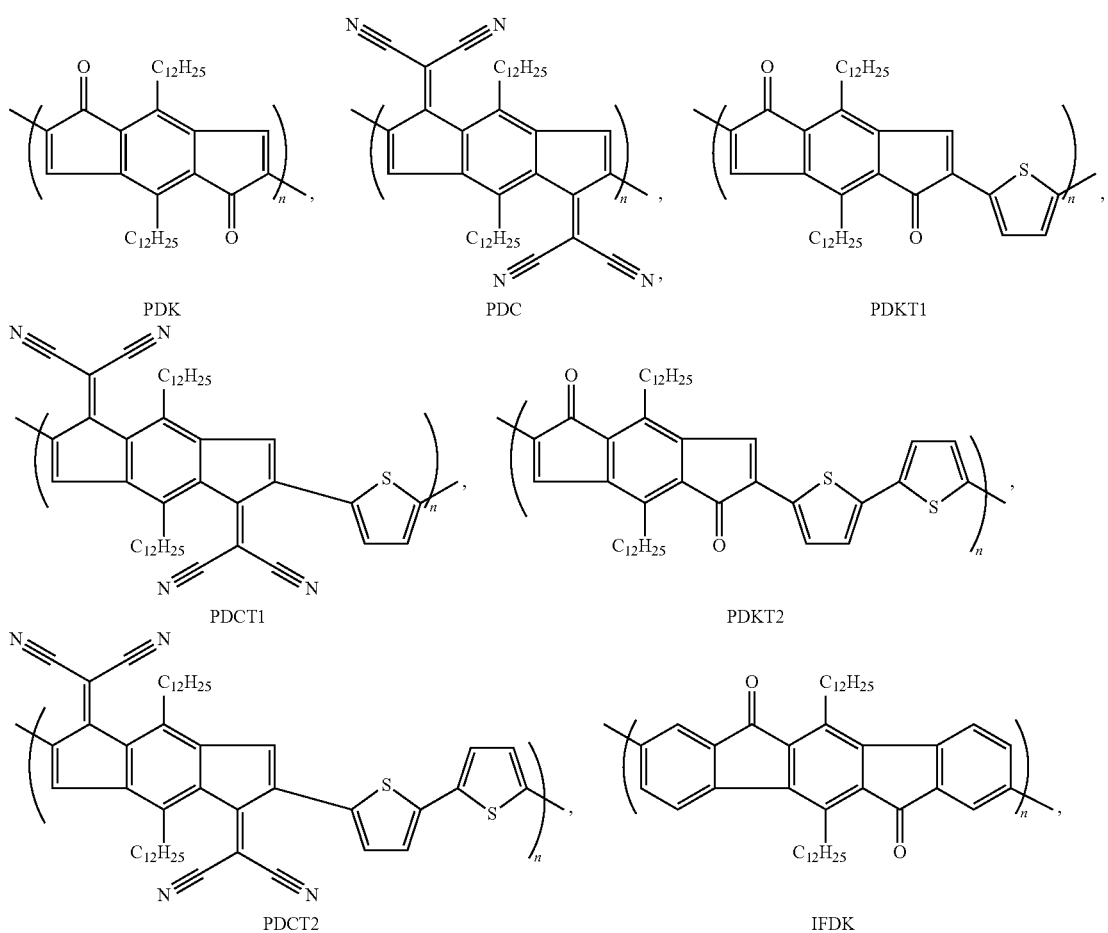

-continued
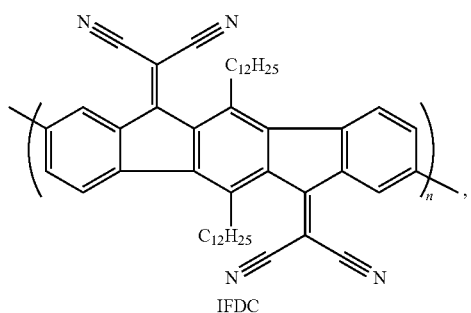
IFDC
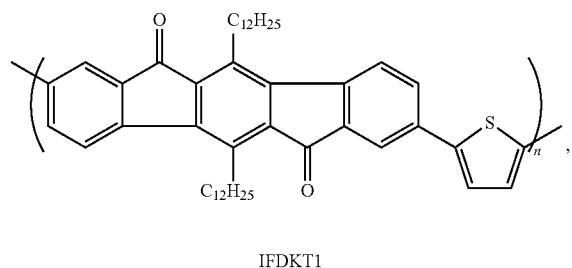
IFDKT1
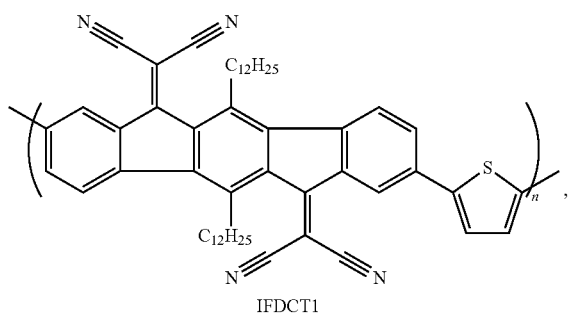
IFDCT1
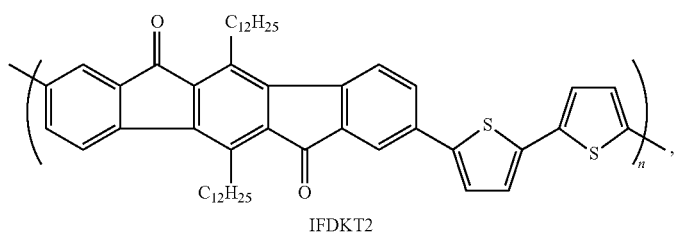
IFDKT2
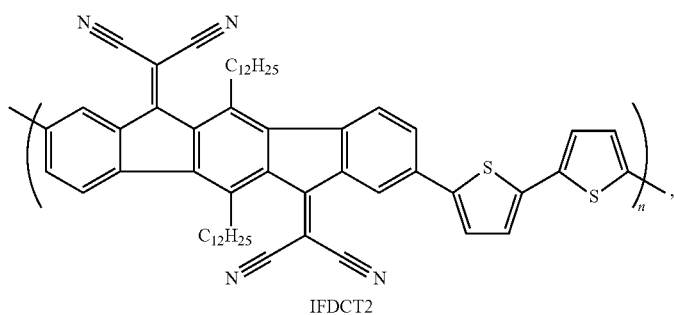
IFDCT2
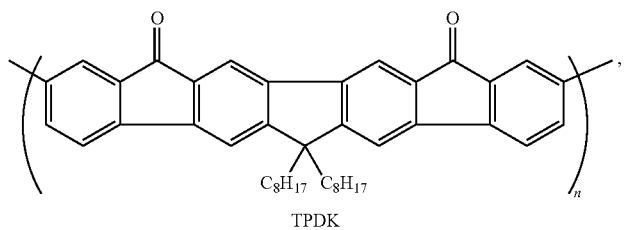
TPDK -continued
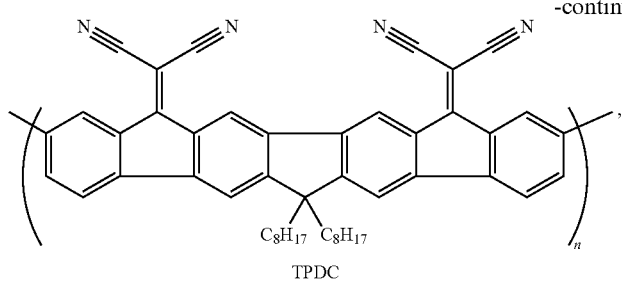
TPDC
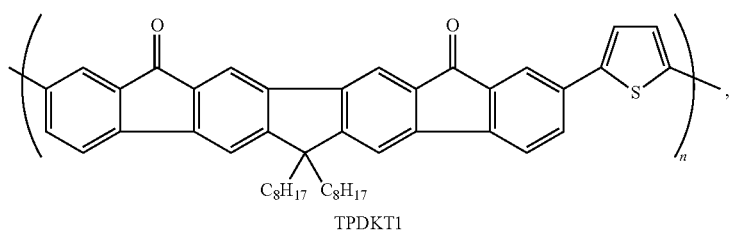
TPDKT1
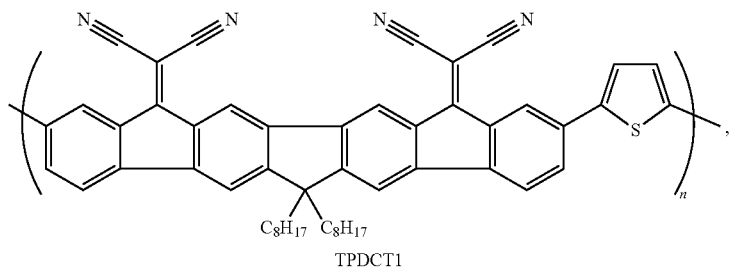
TPDCT1
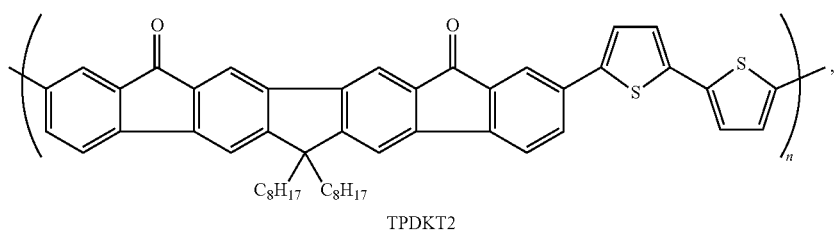
TPDKT2
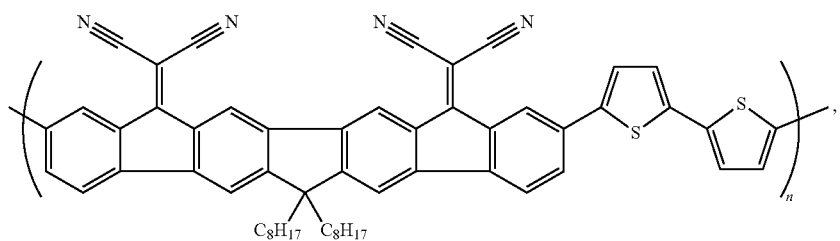
TPDCT2
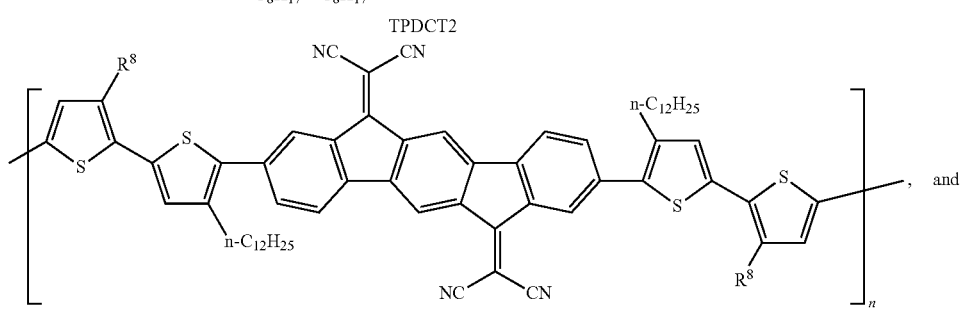
IFDMT 4-12, R$^8$ = C$_{12}$H$_{25}$,
IFDMT 4-6, R$^8$ = C$_6$H$_{13}$
and

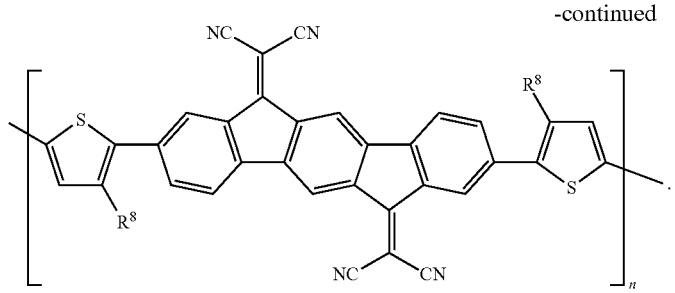

TIFDMT-12, $R^8 = C_{12}H_{25}$, and
TIFDMT-8, 12, $R^8 = CH_2CH(C_8H_{17})C_{12}H_{25}$ where n is an integer in the range of 5 to 100.

Compounds of the present teachings can be prepared in accordance with the procedures outlined in the schemes below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (NMR, e.g., $^1H$ or $^{13}C$), infrared spectroscopy (IR), spectrophotometry (e.g., UV-visible), mass spectrometry (MS), or by chromatography such as high pressure liquid chromatograpy (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Compounds of formula I, formula I', formula I'', formula III, formula IV, formula V, formula VII, formula VIII, and formula IX, including compounds 4, 5, 5B, 6, 6B, 9, 9B, 10, 10B, 15, 16, 19, 20, 21, 22, 30 and 31 can be prepared generally according to Schemes 1-8 below.

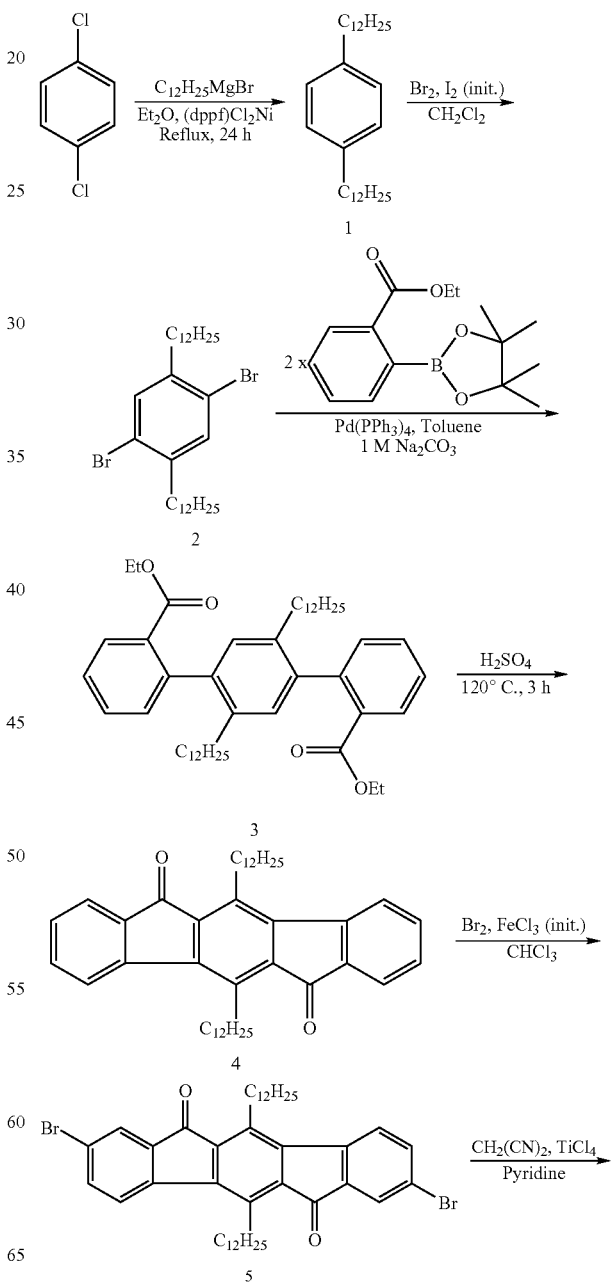

Scheme 1

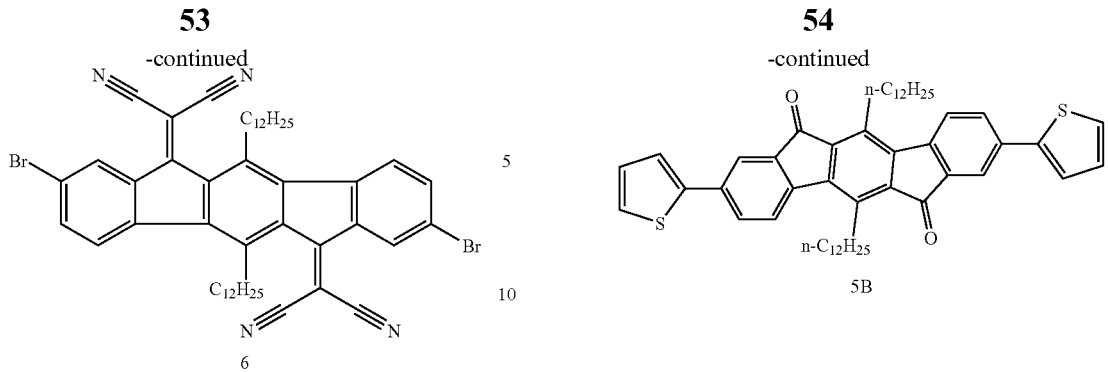

As shown in Scheme 1, the Kumada coupling reaction of n-dodecylmagnesium bromide with 1,4-dichlorobenzene can provide 1,4-di-n-dodecylbenzene 1, which can be selectively brominated in dichloromethane under exclusion of light resulting in 2,5-dibromo-1,4-di-n-dodecylbenzene 2. The Suzuki coupling of compound 2 with 2-(ethoxycarbonyl) phenylboronic acid pinacol ester can provide compound 3. The indenofluorenedione product 4 can be prepared by a double intramolecular Friedel-Crafts acylation of the diester 3 with concentrated sulfuric acid at an elevated temperature. Compound 4 can be brominated at the 2 and 8 positions selectively to give the monomer 5 by using $FeCl_3/Br_2$ under exclusion of light. The dimalononitrile compound 6 can be prepared by the Knoevenagel condensation of compound 5 using an excess amount of malononitrile with piperidine in the presence of $TiCl_4$. The conversion from compound 5 to compound 6 has been confirmed by Fourier transform infrared (FTIR) spectra, in which the carbonyl stretching disappears and the cyano stretching at 2222 $cm^{-1}$ can be seen.

Scheme 2

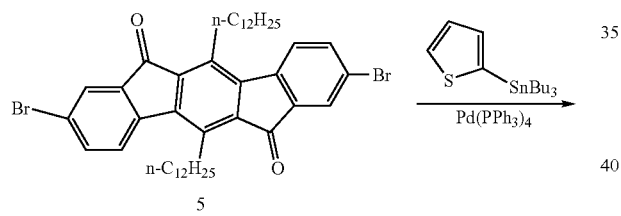

As shown in Scheme 2, compounds 5B and 6B can be obtained through the couplings of 5 and 6, respectively, with 2-tributylstannylthiophene by Stille reactions using $Pd(PPh_3)_4$ as the catalyst.

Scheme 3

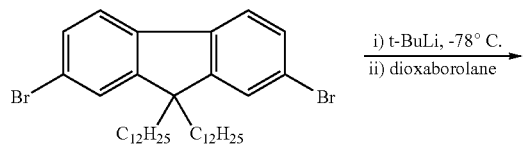

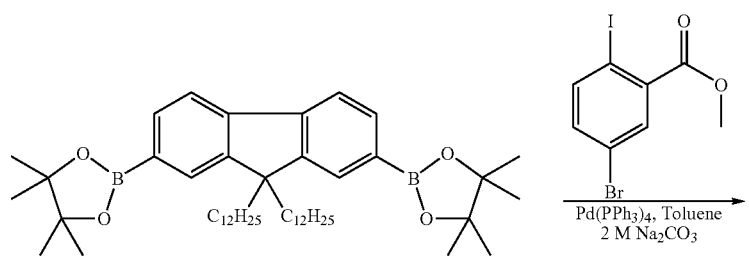

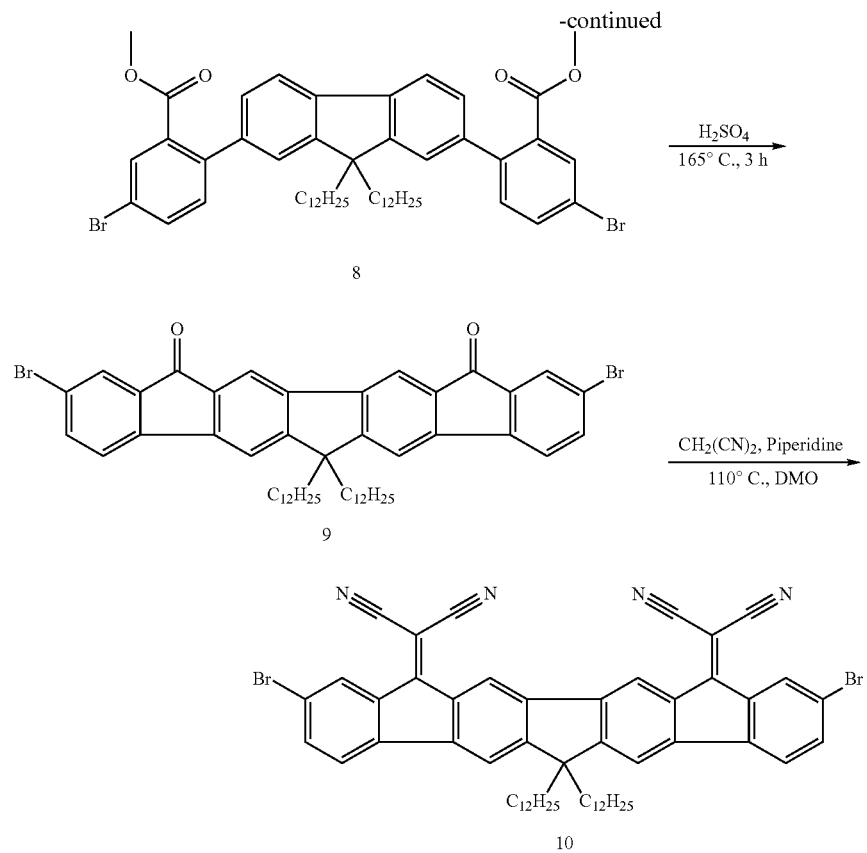

As shown in Scheme 3, monomers 9 and 10 can be prepared by a Friedel-Crafts acylation, followed by a Knoevagel condensation. More specifically, fluorene boronic ester 7 can be prepared from 2,7-dibromofluorene by a double lithiation with t-butyllithium and subsequent addition of 2-isopropoxy-4,4,5,5-tetramethyl[1,3,2]dioxaborolane. Tetraphenyldiester compound 8 can be prepared by the selective Suzuki coupling of the resulting boronic ester 7 with methyl 2-iodo-5-bromobenzoate. Monomer 9 can be prepared by the double intramolecular Friedel-Crafts acylation of compound 8 with concentrated sulfuric acid at an elevated temperature. The Knoevenagel condensation of tetraphenyldione 9 with malononitrile in the presence of piperidine can provide monomer 10.

Scheme 4

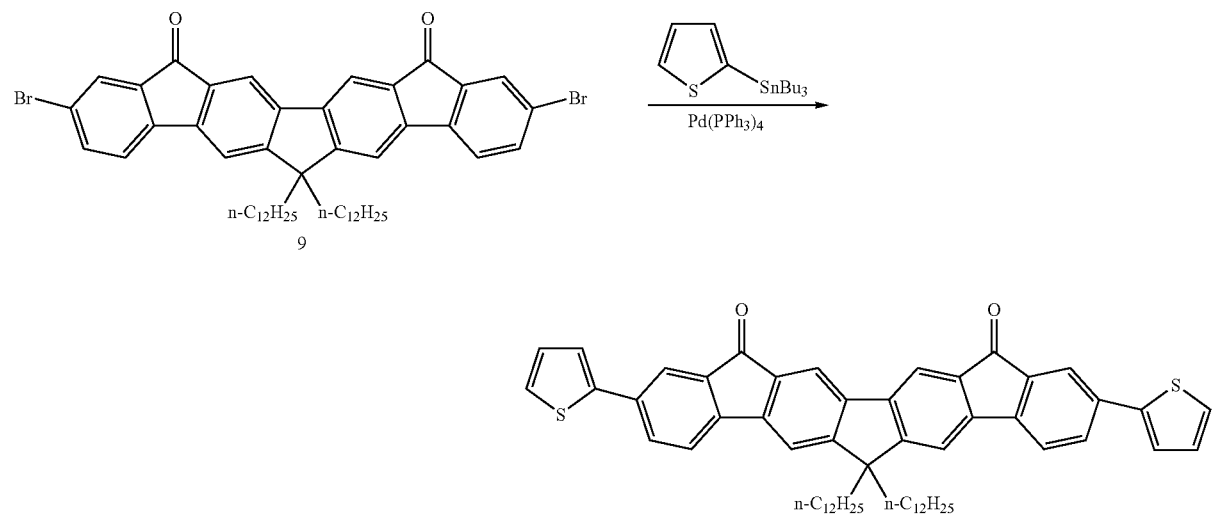

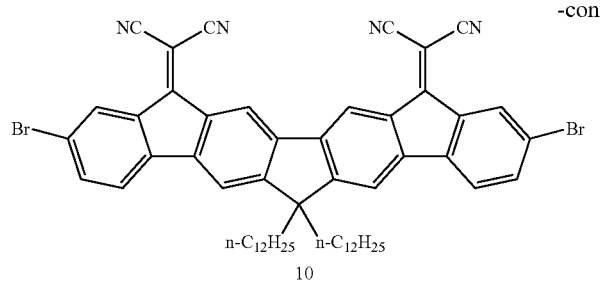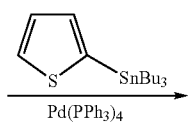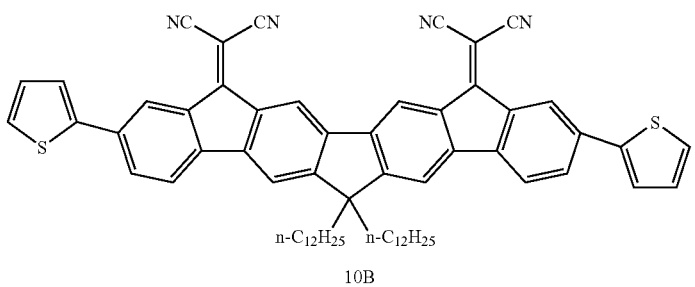
As shown in Scheme 4, the Stille couplings of 9 and 10 with 2-tributylstannylthiophene using Pd(PPh$_3$)$_4$ as the catalyst can provide compounds 9B and 10B, respectively.
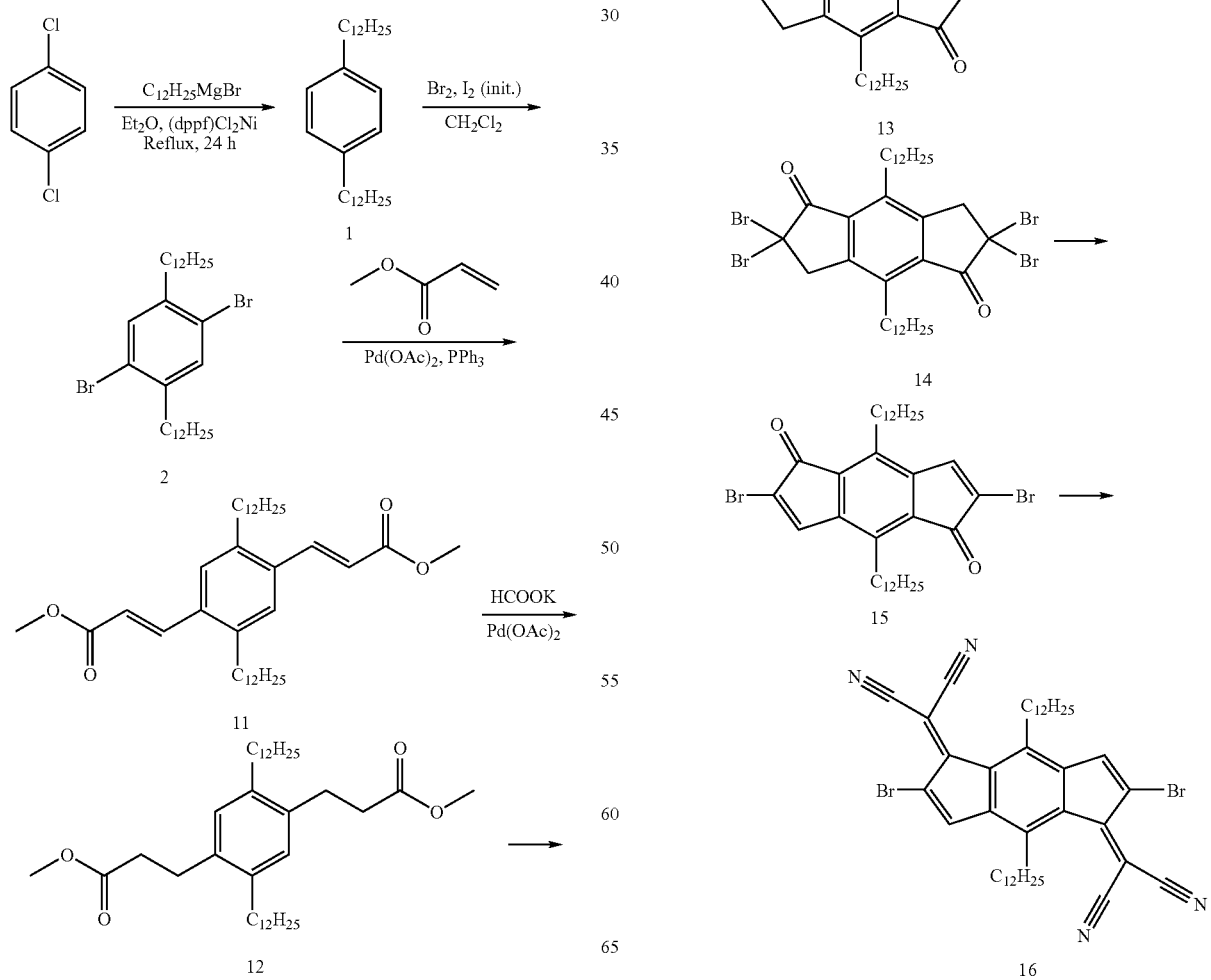

As shown in Scheme 5, diester 11 can be prepared by the Heck coupling of compound 2 with methyl acrylate. Compound 14 can be prepared by a selective reduction of the double bond of the diester 11, followed by a Friedel-Crafts acylation and a double bromination at a positions. Debromination of compound 14 can provide the indacenedione monomer 15. The Knoevenagel condensation of 15 with malononitrile in the presence of piperidine can provide dimalononitrileindacene 16.

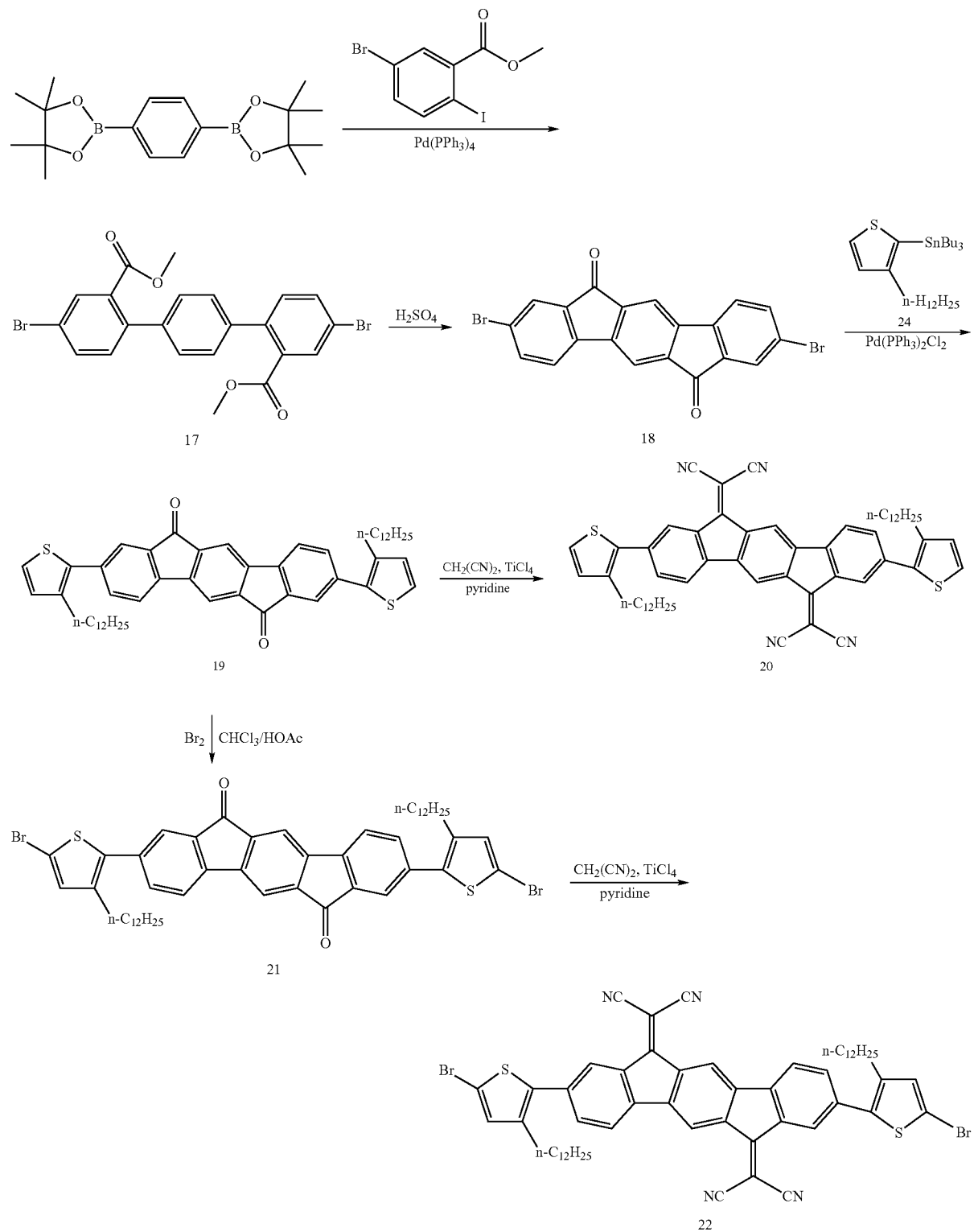

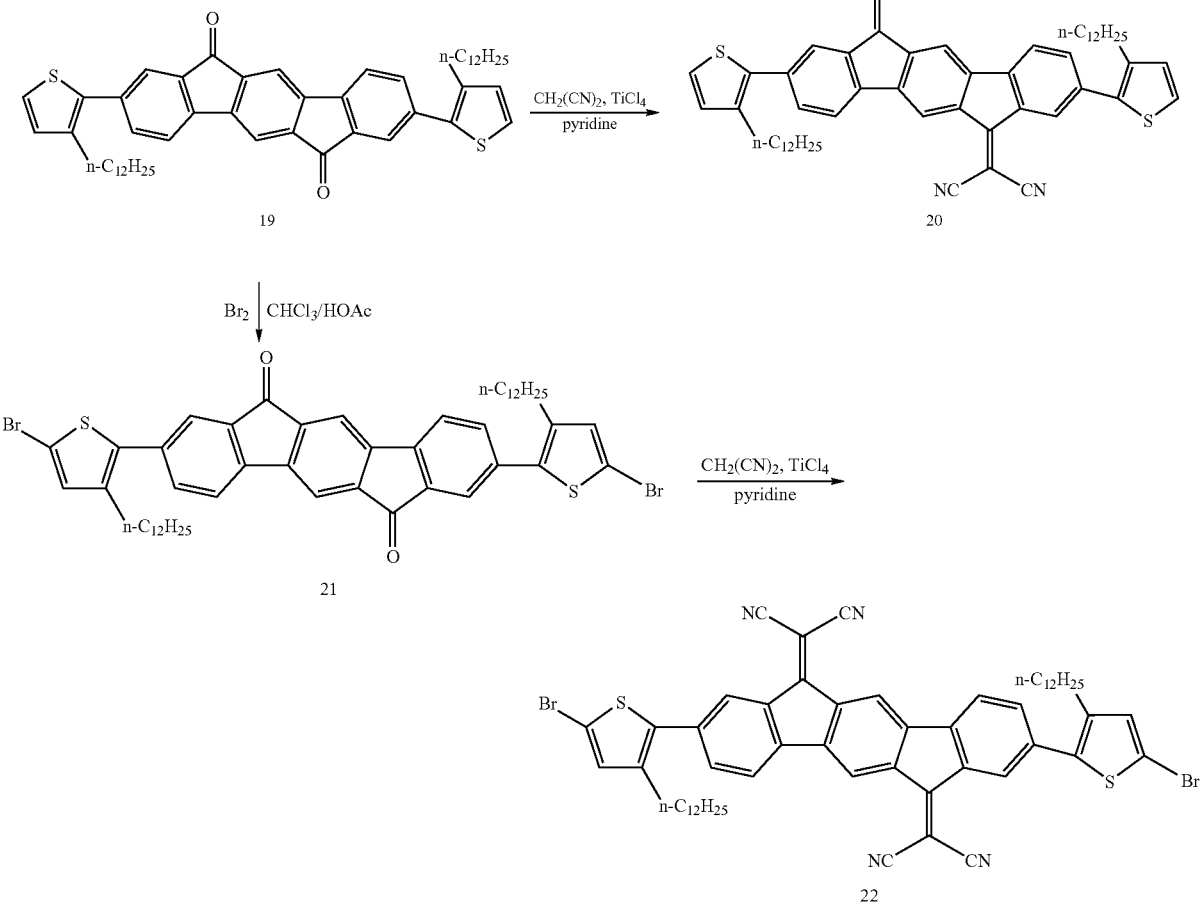

As shown in Scheme 6, compound 17 can be prepared by the Suzuki coupling of 1,4-benzenediboronic acid dipinacol ester with methyl 5-bromo-2-iodobenzoate. An intramolecular Friedel-Crafts acylation of 17 with $H_2SO_4$ at 120° C. can provide compound 18. The $Pd(PPh_3)_2Cl_2$-catalyzed Stille coupling of 18 and 2-tributylstannyl-3-dodecylthiophene (24) in DMF can provide compound 19, which can undergo a reaction with excess malononitrile in the presence pyridine and $TiCl_4$ to afford 20. Polymer building block 21 can be prepared by the bromination of compound 19, which can under to a Knoevenagel condensation with malononitrile to provide compound 22.

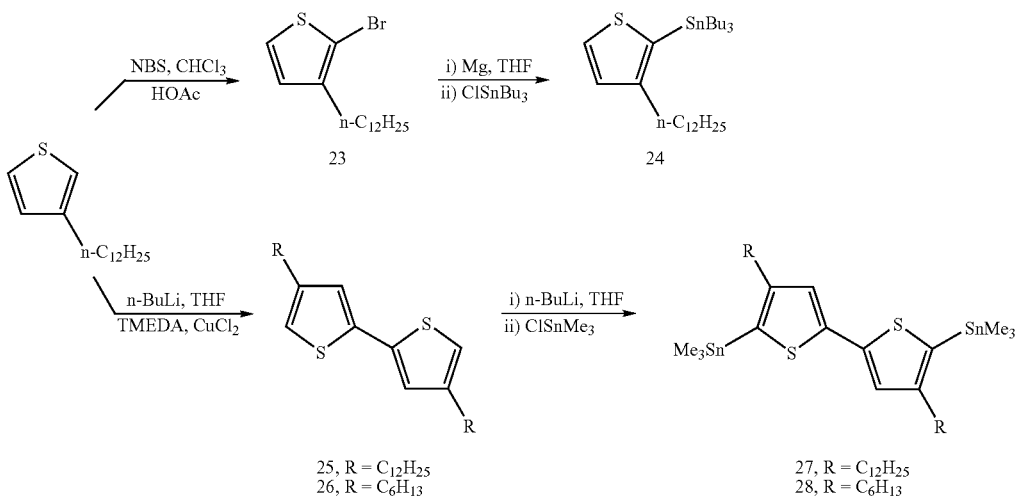

Scheme 7

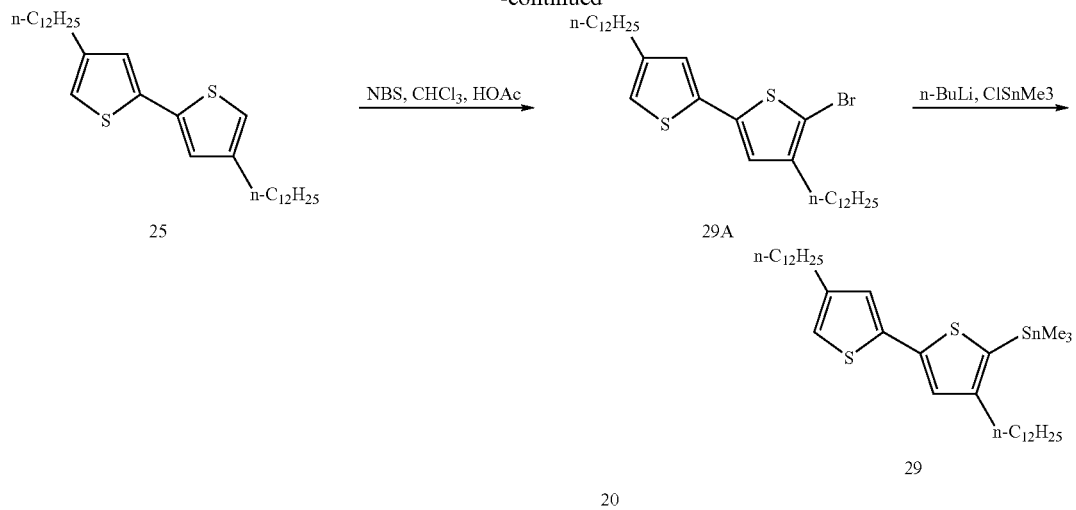

As shown in Scheme 7, the thiophene-based compounds 23-28 can be prepared by selective bromination and stannylation reactions. The oxidative coupling of the mono-lithiated derivative of 3-dodecylthiophene and 3-hexylthiophene in the presence of copper chloride can afford compounds 25 and 26. The selective bromination of 3-dodecylthiophene at 2 position and subsequent lithiation/stannyl chloride addition can give compound 24. Compounds 27 and 28, which can be used as comonomers in the polymerization reactions, can be obtained from compounds 25 and 26, respectively, through double lithiation by n-BuLi followed by the addition of $(CH_3)_3SnCl$. Compound 29 can be obtained by mono-bromination of compound 25 followed by a mono-stannylation.

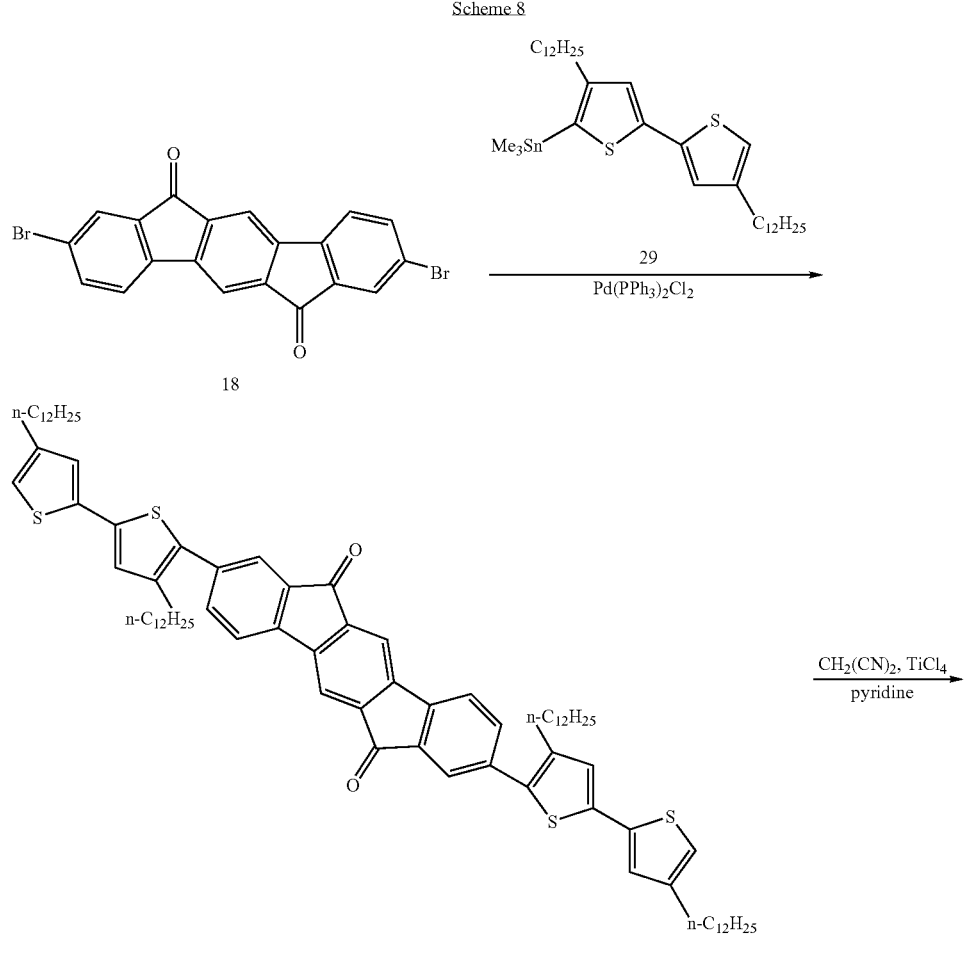

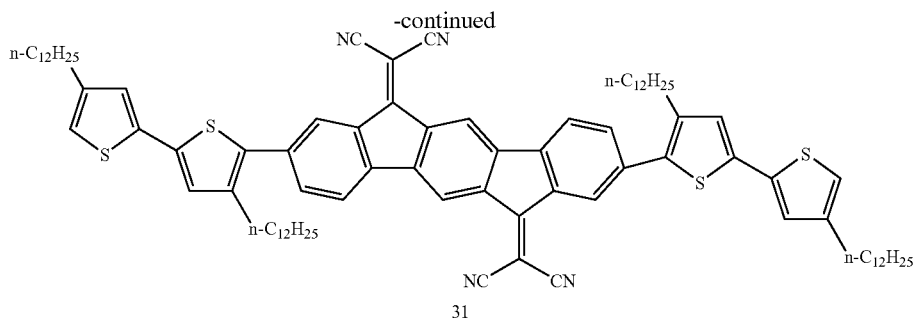

31

As shown in Scheme 8, compound 30 can be obtained by the Stille coupling of compound 18 with 5-tributylstannyl-4,4'-didodecyl-2,2'-bithiophene 29. The Knoevenagel condensation of compound 30 can provide compound 31.

The monomers disclosed herein (e.g., compounds of formula I, formula I', formula I", formula III, formula IV, formula V, formula VII, formula VIII, or formula IX) can react with a suitable boronic ester to provide a polymer of formula VI', including polymers of formula III'", formula IV'", or formula V'", in the form of a copolymer. Alternatively, monomers of the present teachings can self-polymerize under suitable conditions to provide a polymer including repeating units of formula II', formula II", formula III', formula IV', formula V', or formula VI such as a polymer of formula VI' where y is 0 in the form of a homopolymer. Various coupling reactions can be used for preparing the polymers of formulae III'", IV'", V'", and VI'. Exemplary coupling reactions include Suzuki coupling, Yamamoto coupling, Stille coupling, and Negishi coupling.

More specifically, polymers of formula III'", IV'", V'", or VI' can be prepared according to Scheme 9 below.

Scheme 9

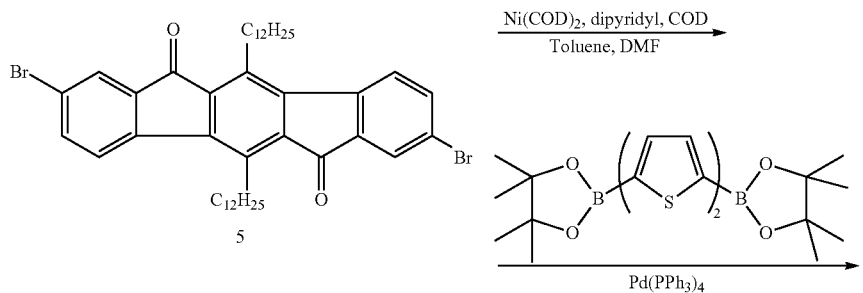

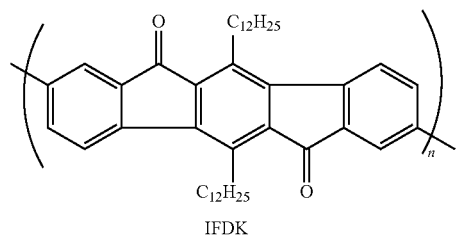

IFDK

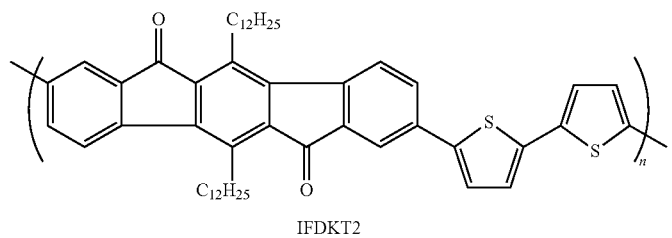

IFDKT2

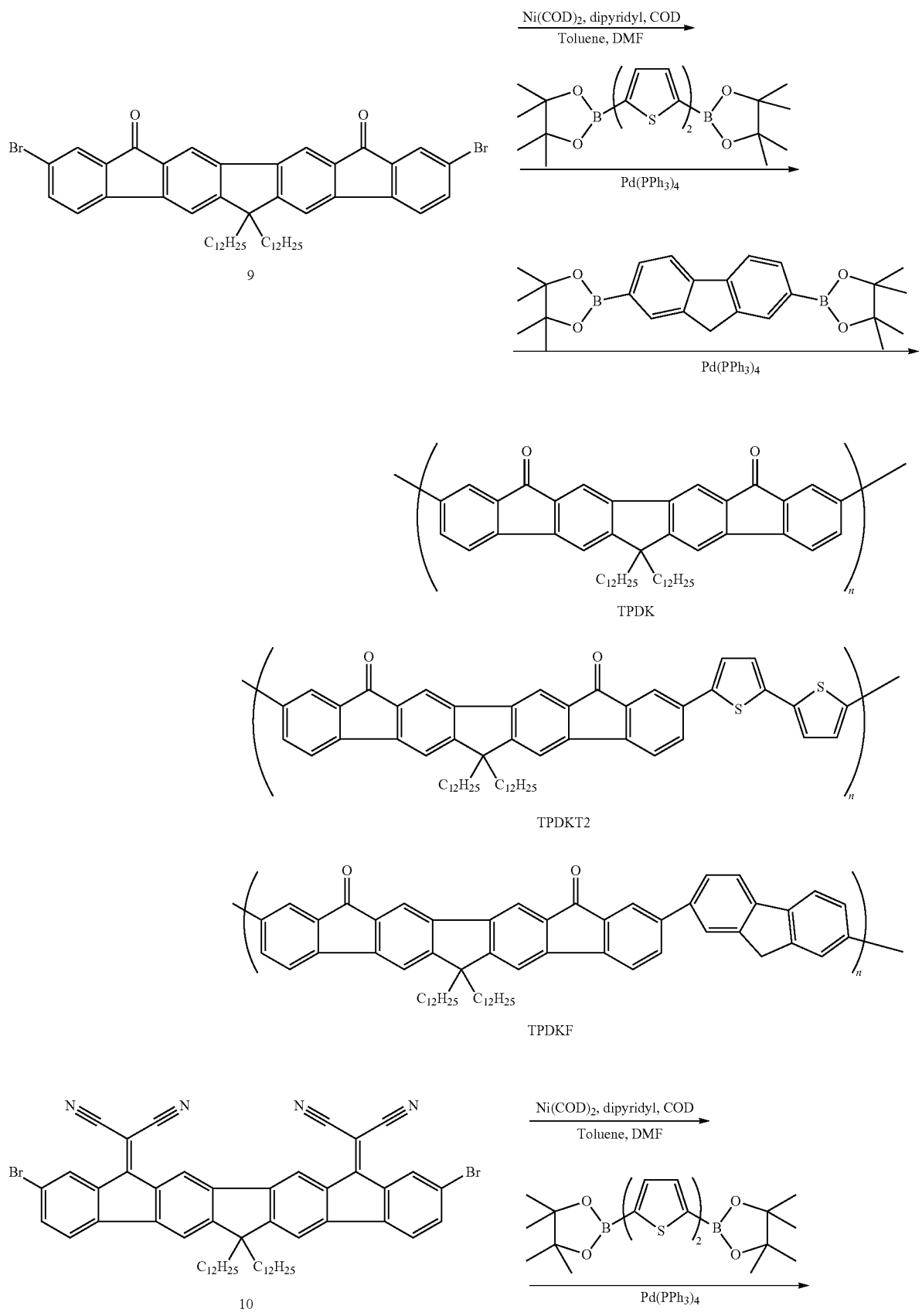

-continued
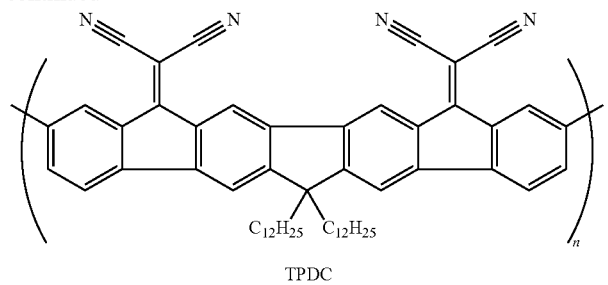
TPDC
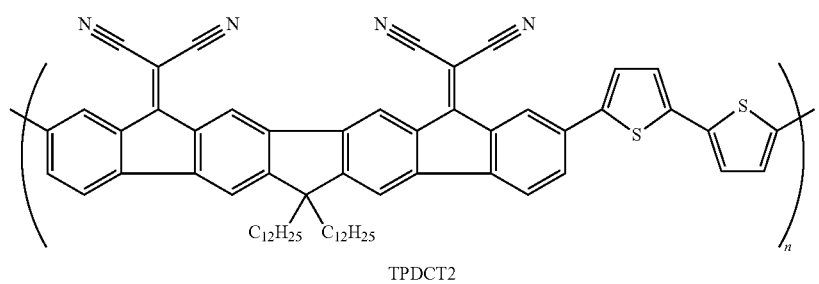
TPDCT2
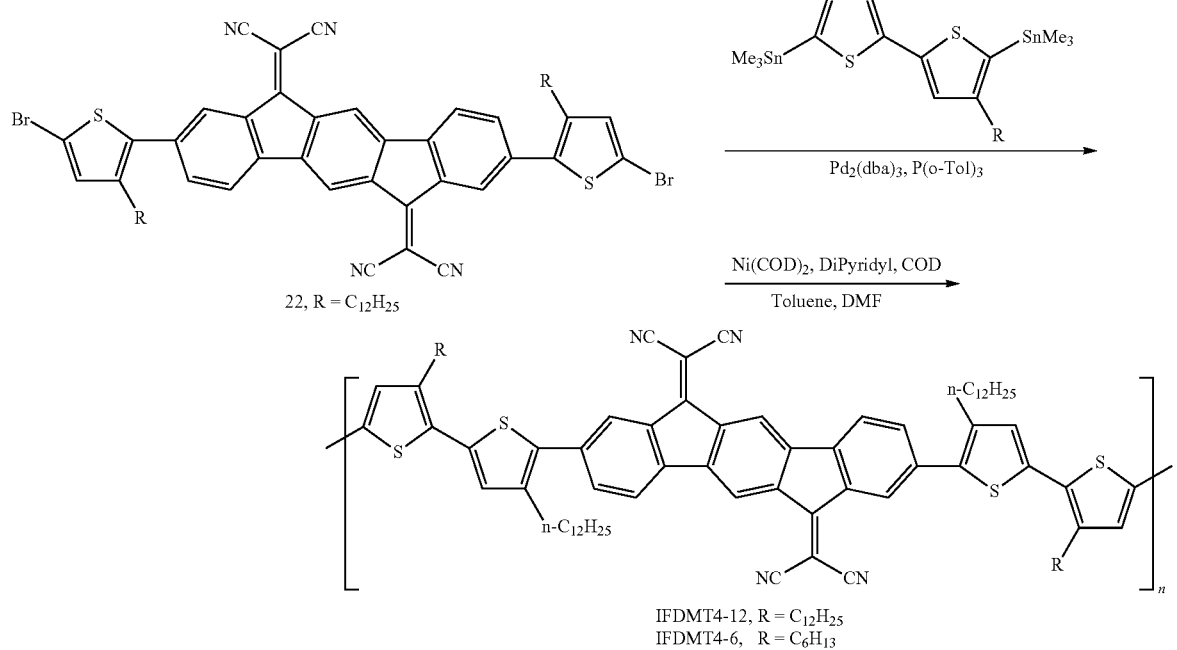
22, R = C$_{12}$H$_{25}$
IFDMT4-12, R = C$_{12}$H$_{25}$
IFDMT4-6, R = C$_6$H$_{13}$
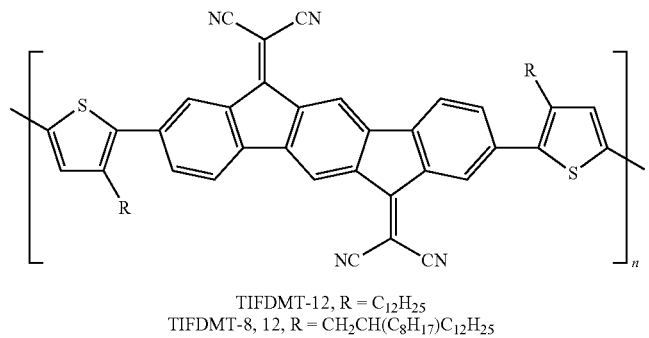
TIFDMT-12, R = C$_{12}$H$_{25}$
TIFDMT-8, 12, R = CH$_2$CH(C$_8$H$_{17}$)C$_{12}$H$_{25}$ As shown in Scheme 9, copolymers including one or more monomers of the present teachings (e.g., copolymers including a monomer of the present teachings and thiophene, bithiophene or 9H-fluorene), can be prepared by a Suzuki coupling of a dibromo-functionalized monomer of the present teachings (e.g., compounds 5, 9, and 10) and a suitable boronic ester (e.g., 5,5'-bis(4,4,5,5-tetramethyl-1,3,2-dioxaborolan-2-yl)-2,2'-bithiophene or 2,2'-(9,9-dioctyl-9H-fluorene-2,7-diyl)bis(4,4,5,5-tetramethyl-1,3,2-dioxaborolane)). For example, thiophene boronic esters can be prepared from mono- and bithiophene according to known procedures such as by double lithiation of 2,2'-bithiophene or thiophene with n-butyllithium and tetramethylethylenediamine (TMEDA), followed by reaction with 2-isopropoxy-4,4,5,5-tetramethyl[1,3,2]dioxaborolane. See, e.g., Hallberg, J. et al., *Synthesis-Stuttgart*, 2003: 2199-2205 (2003). Alternatively, copolymers of the present teachings can be prepared by a Stille coupling of a dibromo-functionalized monomer (e.g., compound 22) with a suitable organotin compound (e.g., (4,4'-dihexyl-2,2'-bithiophene-5,5'-diyl)bis(trimethylstannane)). Following procedures analogous to these as described herein, copolymers IFDKT2, TPDKT2, TPDKF, TPDCT2, IFDMT4-12, and IFDMT4-6 can be prepared, and certain embodiments of these copolymers were found to be soluble in common organic solvents such as chloroform, toluene, and THF.

Referring again to Scheme 9, homopolymers of monomers of the present teachings (e.g., IFDK, TPDK, TPDC, TIFDMT-12, and TIFDMT-8,12) can be prepared via a nickel-mediated homopolymerization reaction. In some embodiments, substitution of the ketone core with the dimalononitrile group (for example, converting TPDK to TPDC) can improve the solubility of the polymer. In some embodiments, polymers of the present teachings can have a limited solubility. For example, diketone-functionalized indenofluorene and tetrapheylene-based homopolymers IFDK and TPDK can be sparsely soluble in conventional organic solvents. Without being bound to any particular theory, the solubility can be mainly due to the highly rigid structure of the ladder-type cores. In some embodiments, polymers of the present teachings can be soluble. For example, bithiophene copolymers can be more soluble than the above homopolymers. Gel permeation chromatography (GPC) showed that one embodiment of TPDC has a weight-average molecular weight ($M_W$) of 12,455 g mol$^{-1}$ with a polydispersity ("PD") of 1.55 versus polystyrene standard at room temperature. This particular embodiment corresponds to a number average degree of polymerization of approximately 10 repeating units. In some embodiments, the weight-average molecular weights ($M_W$s) for TPDKT2, IFDKT2 and IFDMT4-12 can be 9,400 (PD=1.52), 11,200 (PD=1.20), 23,273 (PD=3.48), respectively.

Compounds discussed herein can be used for preparing semiconductor materials (e.g., compositions and composites), which in turn can be used to fabricate various electronic articles, structures and devices. In some embodiments, semiconductor materials incorporating one or more compounds of the present teachings can exhibit n-type semiconducting activity. In some embodiments, semiconductor materials incorporating one or more compounds of the present teachings can exhibit p-type semiconducting activity. In some embodiments, semiconductor materials incorporating one or more compounds of the present teachings can exhibit ambipolar semiconducting activities, i.e. n-type and p-type semiconducting activities under different conditions.

As certain embodiments of the compounds disclosed herein can be soluble in common solvents, the compounds of the present teachings can offer processing advantages when used to fabricate electrical devices such as thin film semiconductors, field-effect devices, organic light emitting diodes (OLEDs), organic photovoltaics, photodetectors, capacitors, and sensors. As used herein, a compound can be considered soluble in a solvent when at least 1 mg of the compound is soluble in 1 mL of the solvent. Examples of common organic solvents include petroleum ethers; acetonitrile; aromatic hydrocarbons such as benzene, toluene, xylene, and mesitylene; ketones such as acetone, and methyl ethyl ketone; ethers such as tetrahydrofuran, dioxane, bis(2-methoxyethyl) ether, diethyl ether, di-isopropyl ether, and t-butyl methyl ether; alcohols such as methanol, ethanol, butanol, and isopropyl alcohol; aliphatic hydrocarbons such as hexanes; acetates such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone. Examples of common inorganic solvents include water and ionic liquids.

Accordingly, the present teachings further provide compositions that can include one or more compounds disclosed herein dissolved or dispersed in a liquid medium, for example, an organic solvent, an inorganic solvent, or combinations thereof (e.g., a mixture of organic solvents, inorganic solvents, or organic and inorganic solvents). In some embodiments, the composition can further include one or more additives independently selected from detergents, dispersants, binding agents, compatiblizing agents, curing agents, initiators, humectants, antifoaming agents, wetting agents, pH modifiers, biocides, and bactereriostats. For example, surfactants and/or other polymers (e.g., polystyrene, polyethylene, poly-alpha-methylstyrene, polyisobutene, polypropylene, polymethylmethacrylate, and so forth) can be included as a dispersant, a binding agent, a compatiblizing agent, and/or an antifoaming agent. In some embodiments, such compositions can include one or more compounds disclosed herein, for example, two or more different compounds of the present teachings can be dissolved in an organic solvent to prepare a composition for deposition.

Various deposition techniques, including various solution-processing techniques, have been used in organic electronics. For example, much of the printed electronics technology has focused on inkjet printing. Inkjet printing is a noncontact process, which offers the benefits of greater control over feature position, multilayer registration, and not requiring a preformed master (compared to contact printing techniques), as well as digital control of ink ejection, thereby providing drop-on-demand printing. However, contact printing techniques have the key advantage of being well-suited for very fast roll-to-roll processing. Exemplary contact printing techniques include, but are not limited to, screen-printing, gravure printing, offset printing, flexographic printing, lithographic printing, pad printing, and microcontact printing. As used herein, "printing" includes noncontact printing process, such as inkjet printing and so forth, and contact printing process, such as screen printing, gravure printing, offset printing, flexographic printing, lithographic printing, pad printing, micro-contact printing, and so forth. Other solution processing techniques include, for example, spin coating, drop-casting, zone casting, dip coating, blade coating, or spraying. In addition, the deposition step can be carried out by vacuum vapor deposition.

The present teachings, therefore, further provide methods of preparing a semiconductor material. The methods can include preparing a precursor composition that includes one or more compounds disclosed herein in a solvent or a mixture of solvents, depositing the precursor composition on a substrate to provide a semiconductor material precursor, and processing (e.g., heating) the semiconductor precursor to provide a semiconductor material (e.g., a thin film semiconductor) that includes a compound disclosed herein. In some embodiments, the depositing step can be carried out by printing, including inkjet printing and various contact printing techniques (e.g., screen-printing, gravure printing, offset printing, pad printing, and microcontact printing). In other embodiments, the depositing step can be carried out by spin coating, drop-casting, zone coating, dip coating, blade coating, or spraying. In yet other embodiments, the depositing step can be carried out by vacuum vapor deposition.

The present teachings further provide articles of manufacture, for example, composites that include a semiconductor material of the present teachings and a substrate component and/or a dielectric component. The substrate component can be selected from materials including doped silicon, an indium tin oxide (ITO), ITO-coated glass, ITO-coated polyimide or other plastics, aluminum or other metals alone or coated on a polymer or other substrate, a doped polythiophene, and so forth. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), and a self-assembled superlattice/self-assembled nanodielectric (SAS/SAND) material (e.g., described in Yoon, M-H. et al., *PNAS*, 102 (13): 4678-4682 (2005), the entire disclosure of which is incorporated by reference herein), as well as a hybrid organic/inorganic dielectric material (e.g., described in U.S. patent application Ser. No. 11/642,504, the entire disclosure of which is incorporated by reference herein). The self-assembled superlattice/self-assembled nanodielectric materials mentioned above can include periodically alternating layers, wherein these alternating layers can include two or more of: (i) layers including a silyl or siloxane moiety, (ii) layers including a π-polarizing moiety (e.g., a stilbazolium group), and (iii) coupling layers including a siloxane matrix. In certain embodiments, the self-assembled superlattice/self-assembled nanodielectric materials can be prepared by layer-by-layer solution phase deposition of molecular silicon precursors, for example, silicon-containing aliphatic and aromatic compounds. With regard to the hybrid organic/inorganic dielectric materials, these materials can have periodically alternating layers that include one or more inorganic layers having an inorganic moiety selected from one or more main group metals and transition metals, and two or more organic layers selected from: (i) layers including a silyl or siloxane moiety, (ii) layers including a π-polarizing moiety (e.g., a stilbazolium group), and (iii) coupling layers including a siloxane matrix. The dielectric component also can be prepared from one of the crosslinked polymer blends described in U.S. patent application Ser. Nos. 11/998,159, 11/823,859, and 11/315,076, the entire disclosure of each of which is incorporated by reference herein. In some embodiments, the crosslinked polymer blends can include a polymeric component (e.g., a polyalkylene) and a crosslinker (e.g., a siloxane moiety). In certain embodiments, the polymeric component and the crosslinker can be the same molecule, e.g., the crosslinker can be a pendant group on the polymeric backbone.

The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)). One or more of the composites described herein can be incorporated within various organic electronic, optical, and optoelectronic devices such as organic thin film transistors (OTFTs), specifically, organic field effect transistors (OFETs), as well as sensors, photovoltaics such as solar cells, capacitors, complementary circuits (e.g., inverter circuits), and so forth.

Other articles of manufacture in which compounds of the present teachings specifically can be useful include photovoltaics or solar cells. Compounds of the present teachings can exhibit broad optical absorption and/or a very positively shifted reduction potential, making them desirable for such applications. Accordingly, the compounds described herein can be used as a semiconductor in a photovoltaic design, for example, such compounds can be included in a semiconducting material that forms a p-n junction. The compounds can be in the form of a thin film semiconductor, which can be a composite of the thin film semiconductor deposited on a substrate. Exploitation of compounds of the present teachings in such devices is within the knowledge of the skilled artisan.

Accordingly, another aspect of the present teachings relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures.

In certain embodiments, OTFT devices can be fabricated with the present compounds on low resistivity n-type silicon wafers, using thermally grown $SiO_2$ (300 nm), HMDS-treated and OTS-treated $SiO_2$ as the dielectric, in top-contact geometries. In particular embodiments, the active semiconducting layer which incorporates at least a compound of the present teachings can be deposited by vacuum vapor deposition at room temperature or at an elevated temperature. In other embodiments, the active semiconducting layer which incorporates at least a compound of the present teachings can be applied by spin-coating or jet printing. For top-contact devices, gold contacts can be patterned on top of the films using shadow masks, giving channel lengths from about 25 μm to about 100 μm and widths from about 500 μm to about 2000 μm.

The following examples are provided to illustrate further and to facilitate the understanding of the present teachings and are not in any way intended to limit the invention.

All reagents were purchased from commercial sources and used without further purification unless otherwise noted. Anhydrous THF and toluene were distilled from Na/benzophenone. Conventional Schlenk techniques were used and reactions were carried out under $N_2$ unless otherwise noted. Examples 1-34 describe the preparation of certain compounds of the present teachings and related intermediates. Characterization data are provided in some cases by $^1$H-NMR, $^{13}$C-NMR, elemental analysis, and/or electron ionization/electron spray ionization (EI/ESI) mass spectroscopy. NMR spectra were recorded on a Varian Unity Plus 500 spectrometer ($^1$H, 500 MHz; $^{13}$C, 125 MHz). Electrospray mass spectrometry was performed with a Thermo Finnegan model LCQ Advantage mass spectrometer.

Example 1

Preparation of 1,4-di-n-dodecylbenzene (1)

n-Dodecylmagnesium bromide (235 mL, 235.0 mmol, 1.0 M in diethyl ether) was added dropwise over 15 minutes, to a solution of 1,4-dichlorobenzene (15.00 g, 102.0 mmol) and [1,3-bis(diphenylphosphino)propane]nickel(II)chloride ((dppp)Cl$_2$Ni, 70 mg) in dry ether (70 mL) at 0° C. The reaction mixture was subsequently allowed to warm to room temperature for about 30 minutes, heated under reflux for 1 day, and cooled to 0° C. again. The reaction was carefully quenched with water (10 mL) and HCl (70 mL, 2 M) and the aqueous layer was extracted with ether (2×50 mL). The combined organic layers were washed with water (30 mL), dried over MgSO$_4$, and filtered. The solvent was then removed in vacuo and the crude product was heated to 100° C. under high vacuum (~20 mtorr) for 10 hours to remove n-octane and n-octylbromide. 1,4-Di-n-dodecylbenzene (1) was obtained as a white solid (35.00 g, 83%). $^1$H NMR (CDCl$_3$): δ 0.88 (t, 6H), 1.30 (m, 36H), 1.61 (m, 4H), 2.59 (t, 4H), 7.10 (s, 4H) ppm.

Example 2

Preparation of 2,5-dibromo-1,4-di-n-dodecyl-benzene (2)

Bromine (2.5 mL, 44.2 mmol) was added quickly to a stirred solution of 1 (5.00 g, 12.1 mmol) and iodine (15 mg) in dichloromethane (15 mL) at 0° C. and the resulting mixture was stirred under rigorous exclusion of light for 2 days at room temperature. Aqueous KOH solution (20 mL, 20%) was added until the dark color of the solution disappeared. Dichloromethane was removed under reduced pressure and the precipitate was washed with ethanol. The crude material was purified by recrystallization from ethanol to afford 2,5-dibromo-1,4-di-n-dodecylbenzene (2) as a white solid (5.20 g, 75%). $^1$H NMR (CDCl$_3$): δ 0.88 (t, 6H), 1.33 (m, 36H), 1.59 (m, 4H), 2.67 (t, 4H), 7.37 (s, 2H) ppm.

Example 3

Preparation of 2,2"-ethoxycarbonyl-2',5'-didodecyl-[1,1';4',1"]terphenyl (3)

2,5-Dibromo-1,4-di-n-dodecylbenzene (2, 0.7 g, 1.22 mmol), 2-(ethoxycarbonyl)phenylboronic acid pinacol ester (1.01 g, 3.66 mmol), and Pd(PPh$_3$)$_4$ (150 mg) was dissolved in dry toluene (25 mL) under nitrogen. Deaerated K$_2$CO$_3$ (2.2 g dissolved in 2.5 mL of water and 5.0 mL of ethanol) and Aliquat 336 solution (0.4 mL) was added under nitrogen and the reaction mixture was heated at the refluxing temperature for 1 day. The organic phase was filtered through a plug of Celite® and the filtrate was concentrated to dryness to give a semi-solid crude product. The crude product was purified by column chromatography (silica gel, chloroform:hexane (7:3) as the eluent) to give 2,2"-ethoxycarbonyl-2',5'-didodecyl-[1,1';4',1"]terphenyl (3) as a colorless oil (0.7 g, 45%). $^1$H NMR (CDCl$_3$): δ 0.88 (t, 6H), 0.97 (t, 6H), 1.13-1.45 (m, 40H), 2.37 (m, 4H), 4.08 (q, 4H), 6.95 (d, 2H), 7.30 (t, 2H), 7.42 (q, 2H), 7.53 (q, 2H), 7.97 (d, 2H) ppm; $^{13}$C NMR (CDCl$_3$): δ 13.83, 14.29, 14.36, 22.94, 29.53, 29.61, 29.64, 29.72, 29.89, 30.87, 30.96, 31.85, 32.17, 32.86, 32.96, 60.79 (d), 127.08 (d), 129.34 (d), 130.21 (d), 130.99 (d), 131.48, 131.61 (d), 136.80 (d), 140.43 (d), 142.76 (d), 168.41 (d) ppm; and Elemental analysis: C, 81.39; H, 9.44; O, 9.30.

Example 4

Preparation of 5,11-didodecylindeno[1,2-b]fluorene-6,12-dione (4)

The diester 3 (1.0 g, 1.39 mmol) was added to H$_2$SO$_4$ (61 mL, 80%) and the mixture was heated with stirring at 120° C. for 2 hours during which time the initially colorless oil turned into a dark red color. The reaction mixture was poured into ice and filtered to collect pale orange crystals. After filtration, the collected product was stirred in a sodium hydrogen carbonate solution and water respectively, filtered, and dried at 70° C. under vacuum overnight to give 5,11-didodecylindeno[1,2-b]fluorene-6,12-dione (4) as a pale orange solid (0.80 g, 93%). $^1$H NMR (CDCl$_3$): δ 0.89 (t, 6H), 1.27-1.69 (m, 40H), 3.43 (broad s, 4H), 7.32 (t, 2H), 7.53 (t, 2H), 7.67 (t, 4H) ppm; $^{13}$C NMR (CDCl$_3$): δ 14.38, 22.95, 27.19, 29.62, 29.75, 29.91, 29.94, 29.96, 30.34, 32.18, 123.61, 124.18, 128.77, 134.90, 135.17, 135.94, 138.41, 143.20, 145.12, 194.60 ppm.; m.p: 123-124° C.; MS(EI) m/z (M$^+$): 618.4; and Elemental Analysis: C, 85.23; H, 9.46.

Example 5

Preparation of 2,8-dibromo-5,11-didodecylindeno[1,2-b]fluorene-6,12-dione (5)

The indenofluorenedione 4 (0.5 g, 0.8 mmol) was dissolved in 45 mL of CHCl$_3$. Bromine (20.0 mL) and FeCl$_3$ (0.5 g) were added. The reaction mixture was stirred at room temperature for 1 day under rigorous exclusion of light. Aqueous KOH solution (20 mL, 20%) was added until the dark color of the solution disappeared. Chloroform was removed under reduced pressure, and the precipitate was filtered and washed with water. The crude material was purified by column chromatography (silica gel and chloroform: hexane (7:3) as the eluent) to afford 2,8-dibromo-5,11-didodecylindeno[1,2-b]fluorene-6,12-dione (5) as an orange solid (0.53 g, 85%). $^1$H NMR (CDCl$_3$): δ 0.89 (t, 6H), 1.27-1.59 (m, 40H), 3.29 (broad s, 4H), 7.43 (d, 2H), 7.61 (d, 2H), 7.69 (s, 2H) ppm; $^{13}$C NMR (CDCl$_3$): δ 14.38, 22.95, 27.19, 29.61, 29.69, 29.83, 29.90, 29.94, 30.22, 32.04, 32.18, 123.14, 124.91, 127.48, 135.69, 136.36, 137.67, 138.62, 141.51, 144.72, 192.86 ppm; m.p: 122-123° C.; MS(ESI) m/z (M+): 775.9; and Elemental analysis: C, 66.97; H, 6.84.

Example 6

Preparation of 2,2'-(2,8-dibromo-5,11-didodecylindeno[1,2-b]fluorene-6,12-diylidene)dimalononitrile (6)

2,8-Dibromo-5,11-didodecylindeno[1,2-b]fluorene-6,12-dione 5 (0.100 g, 0.128 mmol) and malonitrile (0.085 g, 1.28 mmol) were dissolved in dry chlorobenzene (20 mL) under nitrogen, and pyridine (0.21 mL) and TiCl$_4$ (0.14 mL) were added. The resulting mixture was stirred at 120° C. for 5 hours under nitrogen. Upon cooling, 20 mL of water was added and the mixture was extracted with chloroform. The organic phase was washed with water, dried over MgSO$_4$, and concentrated to dryness. The product was purified by column chromatography (silica gel; chloroform as the eluent) to afford 2,2'-(2,8-dibromo-5,11-didodecylindeno[1,2-b]fluorene-6,12-diylidene) dimalononitrile (6) as a dark green solid (0.06 g, 50%). $^1$H NMR (CDCl$_3$): δ 0.87 (t, 6H), 1.27-1.59 (m, 40H), 3.20 (broad s, 2H), 3.60 (broad s, 2H), 7.57 (d, 2H, J=8.5 Hz), 7.72 (d, 2H, J=8.5 Hz), 8.43 (s, 2H) ppm; $^{13}$C NMR (CDCl3): δ 14.35, 14.41, 22.93, 29.57, 29.68, 29.76, 29.87, 32.15, 34.64, 81.13, 113.06, 113.35, 123.08, 125.84, 137.25, 137.48, 137.90, 138.97, 140.19, 142.95, 164.41 ppm; m.p: 136-137° C.; MS(EI) m/z (M+): 873.0; IR (KBr) ν=2220 (C≡N) (no carbonyl peak is observed); and Elemental analysis: C, 68.67; H, 6.48; N, 6.27.

Example 7

Preparation of 2,7-bis(4,4,5,5-tetramethyl-1,3,2-dioxaborolane)-9,9-didodecylfluorene (7)

Tert-BuLi (43.9 mL, 74.7 mmol, 1.7 M in pentane) was added over 30 minutes to a solution of 2,7-dibromo-9,9-didodecylfluorene (12.02 g, 18.2 mmol) in dry THF (90.0 mL) under nitrogen at −78° C. The reaction mixture was stirred for 30 minutes at −78° C., and 2-isopropoxy-4,4,5,5-tetramethyl-1,3,2-dioxaborolane (22.2 mL, 108.6 mmol) was added dropwise with stirring at room temperature overnight. The reaction was quenched with water. THF was removed, and the mixture was extracted with diethyl ether. The organic layer was washed with water, dried over MgSO$_4$, filtered, and concentrated to dryness to give 2,7-bis(4,4,5,5-tetramethyl-1,3,2-dioxaborolane)-9,9-didodecylfluorene (7) as a white solid (12.36 g, 90%). $^1$H NMR (CDCl$_3$): δ 0.55 (t, 4H), 0.88 (m, 6H), 1.01 (m, 6H), 1.15-1.28 (m, 14H), 1.4 (s, 24H), 2.01 (t, 4H), 7.72 (2H, d, J=7.5 Hz), 7.75 (2H, s), 7.82 (2H, d, J=7.5 Hz) ppm.

Example 8

Preparation of dimethyl 6,6'-(9,9-didodecylfluorene-2,7-diyl)bis(3-bromobenzoate) (8)

A mixture of compound 7 (3.120 g, 4.14 mmol), methyl 2-iodo-5-bromobenzoate (3.300 g, 9.52 mmol), and Aliquat 336 (0.800 g) was degassed 3 times with N$_2$ before 30.0 mL of dry toluene was added. Tetrakis(triphenylphosphine)palladium (0.50 g) in an aqueous sodium carbonate solution (1M, 1.80 g in 17 mL of water, and deaerated for 2 hours) was added under N$_2$. The mixture was stirred vigorously at the refluxing temperature for 3 days. After cooling the mixture to room temperature, the organic layer was passed through a plug of Celite® to remove palladium black, and the filtrate was concentrated to dryness in vacuo. The product was purified by column chromatography (silica gel; ethyl acetate:hexane (1:9) as the eluent) to afford dimethyl 6,6'-(9,9-didodecylfluorene-2,7-diyl)bis(3-bromobenzoate) (8) as a colorless oil (3.69 g, 96%). $^1$H NMR (CDCl$_3$): δ 0.83 (t, 6H), 1.10 (s, 24H), 1.95 (m, 4H), 3.61 (s, 6H), 7.22 (s, 2H), 7.28 (d, 2H, J=7.5 Hz), 7.33 (d, 2H, J=7.5 Hz), 7.67 (d, 2H, J=7.5 Hz), 7.74 (d, 2H, J=7.5 Hz), 7.97 (s, 2H) ppm.

Example 9

Preparation of dibromotetraphenylenedione (9)

The diester 8 (0.341 g, 0.367 mmol) was added to H$_2$SO$_4$ (13 mL, 80%) and the mixture was heated with stirring at 165° C. for 3 hours. The reaction mixture was poured into ice and filtered to collect dark colored crystals, which were extracted into dichloromethane. The combined organic solutions were washed with an aqueous solution of sodium hydrogen carbonate, and dried over MgSO$_4$. After filtration and concentration, the crude product was purified by column chromatography (silica gel; chloroform:hexane (7:3) as the eluent) to afford dibromotetraphenylenedione (9) as a yellow solid (0.220 g, 70%). $^1$H NMR (CDCl$_3$): δ 0.66 (br s, 6H), 0.85-1.24 (m, 40H), 2.08 (t, 4H), 7.45 (s, 2H), 7.47 (d, 2H, J=8.0 Hz), 7.64 (d, 2H, J=8.0 Hz), 7.80 (s, 2H), 7.99 (s, 2H) ppm; $^{13}$C NMR (CDCl3): δ 14.27, 22.79, 24.10, 29.40, 30.17, 31.97, 40.54, 56.64, 115.16, 116.56, 121.93, 123.14, 127.79, 133.99, 136.76, 137.28, 141.66, 143.39, 143.96, 158.99, 191.87 ppm; m.p: 138-139° C.; MS(EI) m/z (M+): 864.3. IR (KBr) ν=1722 (C=O); and Elemental analysis: C, 70.44; H, 7.18.

Example 10

Preparation of dibromotetraphenylenedimalononitrile (10)

Dibromotetraphenylenedione 9 (0.520 g, 0.60 mmol) and malonitrile (0.570 g, 8.66 mmol) were dissolved in dry DMSO (14 mL) and piperidine (0.5 mL) was added. The resulting mixture was stirred at 110° C. for 5 hours. Upon cooling, the product precipitated from the solution as brown solids which was filtered, washed with isopropanol, and dried in vacuo. The product was purified by column chromatography (silica gel; chloroform as the eluent) to afford the dibromotetraphenylenedimalononitrile (10) as a purple solid (0.37 g, 65%). $^1$H NMR (CDCl$_3$): δ 0.67 (br s, 6H), 0.85-1.27 (m, 40H), 2.08 (t, 4H), 7.50 (s, 2H), 7.51 (d, 2H, J=8.0 Hz), 7.67 (d, 2H, J=8.0 Hz), 8.52 (s, 2H), 8.83 (s, 2H) ppm; $^{13}$C NMR (CDCl$_3$): δ 14.20, 22.40, 24.15, 29.60, 30.05, 30.17, 31.68, 40.34, 56.74, 113.16, 113.19, 115.55, 118.91, 122.06, 123.22, 129.98, 133.87, 136.72, 137.48, 141.24, 141.39, 141.99, 158.95, 159.68 ppm; MS(EI) m/z (M+): 960.3; m.p: 252-253° C.; IR (KBr) ν=2222 cm$^{-1}$ (C≡N)(no carbonyl peak is observed); and Elemental analysis: C, 71.49; H, 6.42; N, 5.59.

Example 11

Preparation of (2E,2'E)-dimethyl 3,3'-(2,5-didodecyl-1,4-phenylene)diacrylate (11)

A solution of compound 2 (573 mg, 1 mmol), methyl acrylate (20 mmol), Et$_3$N (2.8 mL, 20 mmol), Pd(OAc)$_2$ (25 mg, 0.11 mmol), and tri-phenylphosphine (57 mg, 0.22 mmol) in DMF (20 mL) was heated in a sealed glass tube under nitrogen at 120° C. for 2 days. After cooling, the solvent was removed under reduced pressure to give a residue that was purified by flash chromatography (hexane:EtOAc, 9:1) to give (2E,2'E)-dimethyl 3,3'-(2,5-didodecyl-1,4-phenylene) diacrylate (11) as an off-white solid (300 mg, 51%). $^1$H NMR (CDCl$_3$): δ 0.87 (t, 6H), 1.26-1.56 (m, 40H), 2.72 (t, 4H), 3.83 (s, 6H), 6.42 (d, 2H), 7.39 (s, 2H), 7.98 (d, 2H) ppm; $^{13}$C NMR (CDCl$_3$): δ 14.36, 22.94, 29.60, 29.68, 29.81, 29.89, 31.81, 32.17, 33.17, 51.98, 119.63, 128.20, 134.62, 140.66, 141.93, 167.56 ppm; and MS(EI) m/z (M$^+$): 583.2.

Example 12

Preparation of 4,4''-dibromo-2,2''-methoxycarbonyl-[1,1';4',1'']terphenyl (17)

A mixture of 1,4-benzenediboronic acid bis(pinacol) ester (4.40 g, 13.33 mmol), methyl 2-iodo-5-bromobenzoate (9.95 g, 29.18 mmol), and Aliquat 336 (1.60 mL) was degassed 3 times with N$_2$ before 90.0 mL of dry toluene was added.

Tetrakis(triphenylphosphine)palladium (1.50 g, 1.30 mmol) and 1M aqueous sodium carbonate solution (5.73 g in 54.0 mL of water) which was already deaerated for 2 hours were added under $N_2$. The mixture was stirred vigorously and heated at the refluxing temperature for 2 days and allowed to cool to room temperature. The solution was passed through a plug of Celite to remove palladium black and the filtrate was concentrated to provide a residue, which was purified by column chromatography (silica gel, chloroform) to afford 4,4''-dibromo-2,2''-methoxycarbonyl-[1,1';4',1'']terphenyl (17) as a white solid (6.00 g, 89% yield). $^1$H NMR (CDCl$_3$): δ 3.72 (s, 6H), 7.32 (d, 2H, J=8.0 Hz), 7.33 (s, 4H), 7.69 (d, 2H, J=8.0 Hz), 8.01 (s, 2H) ppm.

Example 13

Preparation of 2,8-dibromo-indeno[1,2-b]fluorene-6,12-dione (18)

4,4''-Dibromo-2,2''-methoxycarbonyl-[1,1';4',1'']terphenyl 17 (0.50 g, 0.99 mmol) was added to $H_2SO_4$ (80%, 50.0 mL, prepared from 10.0 mL of $H_2O$ and 40.0 mL of concentrated (99.99%) $H_2SO_4$) and the mixture was heated with stirring at 120° C. for 10 hours. The reaction mixture was poured into ice and the resulting mixture was filtered. The solid was washed with sodium hydrogen carbonate solution and water to provide 2,8-dibromo-indeno[1,2-b]fluorene-6,12-dione (18) (0.40 g, 92%). The crude product was used for the next step without any further purification. m.p: >300° C.; MS(MALDI-TOF) m/z (M$^+$): 440.7; and Elemental Analysis: C, 54.12; H, 1.72.

Example 14

Preparation of 2,8-di-(3-dodecylthien-2-yl)-indeno[1,2-b]fluorene-6,12-dione (19)

2-Tributylstannyl-3-dodecylthiophene (24) (0.320 g, 0.591 mmol), 2,8-dibromo-indeno[1,2-b]fluorene-6,12-dione 18 (0.120 g, 0.273 mmol), and Pd(PPh$_3$)$_2$Cl$_2$ (30.0 mg, 0.043 mmol) in anhydrous DMF (12.0 mL) were heated at 125° C. under nitrogen overnight. The reaction mixture was cooled to room temperature and concentrated to dryness. The crude product was purified by column chromatography on silica gel (CHCl$_3$/hexanes (7:3)) to provide 2,8-di-(3-dodecylthien-2-yl)-indeno[1,2-b]fluorene-6,12-dione (19) as a purple solid (70.0 mg, 35% yield). $^1$H NMR (CDCl$_3$): δ 0.88-1.66 (m, 46H), 2.70 (t, 4H), 7.02 (d, 2H, J=4.5 Hz), 7.29 (d, 2H, J=4.5 Hz), 7.59 (d, 2H, J=7.5 Hz), 7.61 (d, 2H, J=7.5 Hz), 7.74 (s, 2H), 7.81 (s, 2H) ppm; $^{13}$C NMR (CDCl$_3$): δ 14.4, 22.96, 29.0, 29.6, 29.7, 29.8, 29.9, 30.0, 31.2, 32.2, 116.3, 121.0, 124.7, 125.5, 130.1, 134.6, 136.1, 136.4, 136.8, 139.8, 140.0, 142.3, 145.9, 192.8 ppm; m.p: 152-153° C.; MS(MALDI-TOF) m/z (M$^+$): 783.0; and Elemental Analysis: C, 79.50; H, 7.89.

Example 15

Preparation of 2,8-di-(3-dodecylthien-2-yl)-indeno[1,2-b]fluorene-6,12-dimalononitrile (20)

A mixture of 2,8-di-(3-dodecylthien-2-yl)-indeno[1,2-b]fluorene-6,12-dione 19 (50.0 mg, 0.064 mmol) and malononitrile (60.0 mg, 0.91 mmol) was dissolved in dry chlorobenzene (5.0 mL) under nitrogen, and pyridine (0.100 mL, 1.24 mmol) and TiCl$_4$ (0.070 mL, 0.64 mmol) were added. The resulting mixture was stirred at 110° C. for 5 hours under nitrogen. Upon cooling, 20.0 mL of water was added and the mixture was extracted with chloroform. The organic phase was washed with water, dried over MgSO$_4$, filtered, and concentrated to dryness. The crude product was purified by column chromatography on silica gel (chloroform) to afford 2,8-di-(3-dodecylthien-2-yl)-indeno[1,2-b]fluorene-6,12-dimalononitrile (20) as a dark green solid (22.5 mg, 40%). $^1$H NMR (CDCl$_3$): δ 0.88-1.67 (m, 46H), 2.74 (t, 4H), 7.05 (d, 2H, J=4.0 Hz), 7.33 (d, 2H, J=4.0 Hz), 7.66 (d, 2H, J=7.5 Hz), 7.71 (d, 2H, J=7.5 Hz), 8.52 (s, 2H), 8.60 (s, 2H) ppm; $^{13}$C NMR (CDCl$_3$): δ 14.4, 22.9, 29.2, 29.6, 29.7, 29.8, 29.9, 31.1, 32.2, 112.9, 113.3, 118.4, 121.5, 125.1, 127.8, 130.3, 134.7, 134.7, 135.8, 136.1, 137.3, 139.6, 139.7, 140.5, 143.4, 159.8 ppm; m.p: 232-233° C.; MS(EI) m/z (M$^+$): 879.5; Elemental Analysis: C, 79.07; H, 7.15; N, 6.35. and IR (KBr): ν=2225 cm$^{-1}$ (C≡N, no carbonyl peak is observed).

Example 16

Preparation of 2,8-di-(5-bromo-3-dodecylthien-2-yl)-indeno[1,2-b]fluorene-6,12-dione (21)

To a solution of 2,8-di-(3-dodecylthien-2-yl)-indeno[1,2-b]fluorene-6,12-dimalononitrile (20, 0.30 g, 0.383 mmol) in CHCl$_3$/HOAc (5:1) (V$_t$=24.0 mL) was added bromine (Br$_2$; 123.0 mg, 0.766 mmol) in one portion. The mixture was stirred at room temperature for 10 hours and water (50 mL) was added. The mixture was extracted with chloroform (3×50 mL) and the combined organic phases were washed with water (50 mL), KOH aqueous solution, and dried over MgSO$_4$. After filtration, the chloroform was removed, and the product was purified by silica gel column chromatography (chloroform) to give 2,8-di-(5-bromo-3-dodecylthien-2-yl)-indeno[1,2-b]fluorene-6,12-dione (21) as a dark green solid (0.340 g, 95% yield). $^1$H NMR (CDCl$_3$): δ 0.87-1.61 (m, 46H), 2.70 (t, 4H), 6.96 (s, 2H), 7.56 (d, 2H, J=7.5 Hz), 7.61 (d, 2H, J=7.5 Hz), 7.69 (s, 2H), 7.84 (s, 2H) ppm; MS(EI) m/z (M$^+$): 941.1; and Elemental Analysis: C, 66.34; H, 6.43.

Example 17

Preparation of 2,8-di-(5-bromo-3-dodecylthien-2-yl)-indeno[1,2-b]fluorene-6,12-dimalononitrile (22)

A mixture of 2,8-di-(5-bromo-3-dodecylthien-2-yl)-indeno[1,2-b]fluorene-6,12-dione (21, 230.0 mg, 0.245 mmol) and malononitrile (230.0 mg, 3.48 mmol) was dissolved in dry chlorobenzene (20.0 mL) under nitrogen, and pyridine (0.40 mL, 4.94 mmol) and TiCl$_4$ (0.30 mL, 2.73 mmol) were added. The resulting mixture was stirred at 110° C. for 5 hours under nitrogen. Upon cooling, 20.0 mL of water was added and the mixture was extracted with chloroform. The organic phase was washed with water, dried over MgSO$_4$, filtered, and concentrated to dryness. The crude product was purified by column chromatography on silica gel (chloroform) to afford 2,8-di-(5-bromo-3-dodecylthien-2-yl)-indeno[1,2-b]fluorene-6,12-dimalononitrile (22) as a dark green solid (120.0 mg, 48% yield). $^1$H NMR (CDCl$_3$): δ 0.89-1.62 (m, 46H), 2.66 (t, 4H), 7.00 (s, 2H), 7.59 (d, 2H, J=7.5 Hz), 7.71 (d, 2H, J=7.5 Hz), 8.47 (s, 2H), 8.62 (s, 2H) ppm; MS(EI) m/z (M$^+$): 1037.4; Elemental Analysis: C, 66.76; H, 5.82; N, 5.18. and IR (KBr): ν=2225 cm$^{-1}$ (C≡N, no carbonyl peak is observed).

Example 18

Preparation of 2-bromo-3-dodecylthiophene (23)

To a solution of 3-dodecylthiophene (5.00 g, 19.8 mmol) in CHCl$_3$/HOAc (1:1) (V$_t$=20.0 mL) at 0° C. was added NBS (3.52 g, 19.8 mmol) in portions over a period of 45 minutes. The reaction mixture was stirred for 1 hour at 0° C., and overnight at room temperature. The reaction mixture was poured into water (50.0 mL) and extracted with chloroform (3×50.0 mL). The combined organic phases were washed with water (50.0 mL), NaOH solution, and dried over $MgSO_4$. After filtration through Celite, the chloroform was removed in vacuo, and the product was obtained as a colorless oil (6.05 g, 93% yield). $^1$H NMR ($CDCl_3$): δ 0.84-1.54 (m, 23H), 2.53 (t, 2H), 6.76 (d, 1H, J=4.5 Hz), 7.15 (d, 1H, J=4.5 Hz).

Example 19

Preparation of 2-tributylstannyl-3-dodecyl-thiophene (24)

To magnesium turnings (0.160 g, 6.6 mmol) in anhydrous THF (8.0 mL), heated to maintain a mild reflux, was added dropwise 2-bromo-3-dodecylthiophene (23; 2.00 g, 6.0 mmol). The reaction mixture was refluxed for 2 hours before being transferred to a solution of tributyltin chloride (1.80 mL, 6.41 mmol) in 10.0 mL of anhydrous THF at −78° C. The mixture was warmed to room temperature and stirred overnight before being poured into water. The aqueous layer was extracted with hexanes and the combined organic phase was washed with brine and dried over magnesium sulfate. After filtration, the solvent was removed in vacuo to yield 2-tributylstannyl-3-dodecylthiophene (24) as a yellow liquid (3.10 g, 95% yield). $^1$H NMR ($CDCl_3$): δ 0.90-1.63 (m, 50H), 2.62 (t, 2H), 7.12 (d, 1H, J=4.5 Hz), 7.55 (d, 1H, J=4.5 Hz) ppm.

Example 20

Preparation of 4,4'-didodecyl-2,2'-bithiophene (25)

n-BuLi (7.04 mL, 2.5 M in hexanes) was added dropwise to a stirring solution of 3-dodecylthiophene (4.000 g, 15.8 mmol) and N,N,N',N'-tetramethylethylenediamine (2.75 mL, 17.6 mmol) in 80.0 mL of dry ether at −78° C. The solution was then warmed to room temperature and refluxed for 1 hour. After the solution was cooled to −78° C., $CuCl_2$ (2.640 g, 19.6 mmol) was added in one portion. The reaction mixture was stirred overnight, during which time the temperature rose to room temperature. The reaction mixture was quenched with water and the resulting mixture was extracted with chloroform. The combined organic layers were washed with water, dried over $MgSO_4$ and filtered, and the filtrate was concentrated to dryness. The crude product was purified by column chromatography on silica gel with hexanes as the eluent to yield a mixture of 4,4'- and 3,3'-didodecylthiophene (~15% of the mixture by $^1$H NMR). Recrystallization from an acetone:ethanol (1:1) mixture gave 4,4'-didodecyl-2,2'-bithiophene (25) as a white solid (2.200 g, 55% yield). $^1$H NMR ($CDCl_3$): δ 0.91 (t, 6H), 1.33 (m, 36H), 1.66 (q, 4H), 2.60 (t, 4H), 6.80 (s, 2H), 7.01 (s, 2H) ppm.

Example 21

Preparation of 4,4'-didocecyl-5,5'-trimethylstannyl-2,2'-bithiophene (27)

To a solution of 4,4'-didodecyl-2,2'-bithiophene (25, 1.00 g, 2.0 mmol) in 30.0 mL of THF was added dropwise a solution of n-butyllithium in hexane (2.0 mL, 2.5 M, 5.0 mmol) at −78° C. The solution was stirred at −78° C. for 30 minutes and at room temperature for 1 hour. The solution was then cooled to −78° C. and a solution of trimethyltin chloride in THF (6.0 mL, 1.0 M, 6.0 mmol) was added in one portion. The solution was warmed to room temperature and 30.0 mL of water and 30.0 mL of ethyl acetate were added. The organic layer was washed twice with 30 mL of water and dried over magnesium sulfate. After filtration, the solvent was removed from the filtrate in vacuo to yield 4,4'-didocecyl-5,5'-trimethylstannyl-2,2'-bithiophene (27) as a yellow oil (0.60 g, 72% yield). $^1$H NMR ($CDCl_3$): δ 0.40 (s, 18H), 0.95 (t, 6H), 1.33 (br, 36H), 1.60 (q, 4H), 2.61 (t, 4H), 7.18 (s, 2H).

Example 22

Preparation of 2,8-dithien-2-yl-5,11-didodecylindeno[1,2-b]fluorene-6,12-dione (5B)

Indenofluorenedione 5 (0.200 g, 0.257 mmol), 2-tributylstannylthiophene (0.231 g, 0.618 mmol), and $Pd(PPh_3)_4$ (20 mg) in anhydrous toluene (8.0 mL) were heated overnight at 110° C. under nitrogen. The reaction mixture was cooled to room temperature and concentrated to dryness. The crude product was purified by column chromatography on silica gel ($CHCl_3$/hexanes (7:3)) to give 2,8-dithien-2-yl-5,11-didodecylindeno[1,2-b]fluorene-6,12-dione (5B) as a purple solid (121 mg, 60.0% yield). $^1$H NMR ($CDCl_3$): δ 0.88-1.66 (m, 46H), 3.41 (b s, 4H), 7.11 (t, 2H), 7.39 (d, 2H, J=3.0 Hz), 7.62 (d, 2H, J=7.5 Hz), 7.74 (d, 2H, J=7.5 Hz), 7.88 (s, 2H) ppm; m.p: 205-206° C.; MS(MALDI-TOF) m/z ($M^+$): 783.0; and Elemental Analysis: C, 79.60; H, 7.82.

Example 23

Preparation of 2,8-dithien-2-yl-tetraphenylenedione (9B)

Dibromotetraphenylenedione 9 (0.400 g, 0.531 mmol), 2-tributylstannylthiophene (0.476 g, 1.275 mmol), and $Pd(PPh_3)_4$ (50 mg) in anhydrous toluene (20.0 mL) were heated at 110° C. overnight under nitrogen. The reaction mixture was cooled to room temperature and concentrated to dryness. The crude product was purified by column chromatography on silica gel ($CHCl_3$/hexanes (7:3)) to give 2,8-dithien-2-yl-tetraphenylenedione (9B) as a yellow solid. $^1$H NMR ($CDCl_3$): δ 0.88-1.66 (m, 46H), 2.13 (t, 4H), 7.15 (t, 2H), 7.36 (d, 2H, J=4.5 Hz), 7.44 (d, 2H, J=3.0 Hz), 7.50 (s, 2H), 7.61 (d, 2H, J=7.5 Hz), 7.78 (d, 2H, J=7.5 Hz), 7.97 (s, 2H), 8.03 (s, 2H) ppm; m.p: 180-181° C.; MS(MALDI-TOF) m/z ($M^+$): 871.9; and Elemental Analysis: C, 81.15; H, 7.76.

Example 24

Preparation of 2,8-dithien-2-yl-tetraphenylenedimalononitrile (10B)

Dibromotetraphenylenedimalononitrile 10 (180 mg, 0.187 mmol), 2-tributylstannylthiophene (168 mg, 0.449 mmol), and $Pd(PPh_3)_4$ (15 mg) in anhydrous toluene (8.0 mL) were heated overnight at 110° C. under nitrogen. The reaction mixture was cooled to room temperature and concentrated to dryness. The crude product was purified by column chromatography on silica gel ($CHCl_3$/hexanes (7:3)) to give 2,8-dithien-2-yl-tetraphenylenedimalononitrile (10B) as a yellow solid (0.114 g, 70% yield). $^1$H NMR ($CDCl_3$): δ 0.88-1.66 (m, 46H), 2.10 (t, 4H), 7.13 (t, 2H) 7.35 (d, 2H, J=4.5 Hz), 7.44 (d, 2H, J=3.5 Hz), 7.51 (s, 2H), 7.75 (d, 2H, J=8.0 Hz), 8.69 (s,

Example 25

Preparation of 2,8-di-(4'-dodecylthien-2'-yl-4-dodecylthien-2-yl)-indeno[1,2-b]fluorene-6,12-dione (30)

5-Trimethylstannyl-4,4'-didodecyl-2,2'-bithiophene (29, 0.457 g, 0.686 mmol), compound 18 (0.140 g, 0.312 mmol), and Pd(PPh$_3$)$_2$Cl$_2$ (45.0 mg, 0.064 mmol) in anhydrous DMF (25.0 mL) were heated at 125° C. overnight under nitrogen. The reaction mixture was cooled to room temperature and concentrated to dryness. The crude product was purified by column chromatography on silica gel (CHCl$_3$/hexanes (4:6)) to give 2,8-di-(4'-dodecylthien-2'-yl-4-dodecylthien-2-yl)-indeno[1,2-b]fluorene-6,12-dione (30) as a green solid (100.0 mg, 25% yield). $^1$H NMR (CDCl$_3$): δ 0.88-1.66 (m, 92H), 2.60 (t, 4H), 2.67 (t, 4H), 6.83 (s, 2H), 7.03 (s, 2H), 7.05 (d, 2H), 7.61 (q, 4H), 7.77 (s, 2H), 7.83 (s, 2H) ppm; m.p: 96-97° C.; MS(MALDI-TOF) m/z (M$^+$): 1284.0; and Elemental Analysis: C, 78.20; H, 8.60.

Example 26

Preparation of 2,8-di-(4'-dodecylthien-2'-yl-4-dodecylthien-2-yl)-indeno[1,2-b]fluorene-6,12-dimalononitrile (31)

A mixture of 2,8-di-(4'-dodecylthien-2'-yl-4-dodecylthien-2-yl)-indeno[1,2-b]fluorene-6,12-dione 30 (40.0 mg, 0.031 mmol) and malononitrile (35.0 mg, 0.53 mmol) was dissolved in dry chlorobenzene (3.0 mL) under nitrogen, and pyridine (0.06 mL) and TiCl$_4$ (0.04 mL, 0.64 mmol) were added. The resulting mixture was stirred at 110° C. for 5 hours under nitrogen. Upon cooling, 20.0 mL of water was added and the mixture extracted with chloroform. The organic phase was washed with water, dried over MgSO$_4$, and filtered, and the filtrate was concentrated to dryness. The crude product was purified by column chromatography on silica gel (chloroform) to afford 2,8-di-(4'-dodecylthien-2'-yl-4-dodecylthien-2-yl)-indeno[1,2-b]fluorene-6,12-dimalononitrile (31) as a dark green solid (25 mg, 58%). $^1$H NMR (CDCl$_3$): δ 0.88-1.66 (m, 92H), 2.58 (t, 4H), 2.71 (t, 4H), 6.83 (s, 2H), 7.05 (s, 2H), 7.06 (d, 2H), 7.63 (d, 2H, J=8.0 Hz), 7.68 (d, 2H, J=8.0 Hz), 8.51 (s, 2H), 8.56 (s, 2H) ppm; m.p: 96-97° C.; MS(MALDI-TOF) m/z (M$^+$): 1380.0; and Elemental Analysis: C, 78.55; H, 8.49.

Example 27

Preparation of 5-bromo-4,4'-didodecyl-2,2'-bithiophene (29A)

To a solution of 4,4'-didodecyl-2,2'-bithiophene (0.100 g, 0.199 mmol) in CHCl$_3$/HOAc (1:1) (V$_r$=2.0 mL) at 0° C. was added N-bromosuccimide (NBS, 35.7 mg, 0.199 mmol) in portions over a period of 45 minutes. The reaction mixture was stirred for 1 hour at 0° C. and overnight at room temperature. The reaction mixture was poured into water (50.0 mL) and extracted with chloroform (3×50.0 mL). The combined organic phases were washed with water (50.0 mL), NaOH solution, and dried over MgSO$_4$. After filtration through Celite, the filtrate was concentrated in vacuo and the residue was purified by column chromatography on silica gel (hexanes) to provide 5-bromo-4,4'-didodecyl-2,2'-bithiophene (29A) as a colorless oil (98.0 mg, 85% yield). $^1$H NMR (CDCl$_3$): δ 0.84-1.54 (m, 46H), 2.57 (m, 4H), 6.81 (s, 1H), 6.84 (s, 1H), 6.94 (s, 1H).

Example 28

Preparation of 5-trimethylstannyl-4,4'-didodecyl-2,2'-bithiophene (29)

To a solution of 5-bromo-4,4'-didodecyl-2,2'-bithiophene (29A, 100 mg, 0.172 mmol) in 4.0 mL of THF was added dropwise a solution of n-butyllithium in hexane (0.076 mL, 2.5 M, 0.189 mmol) at −78° C. The solution was stirred at −78° C. for 1 hour and a solution of trimethyltin chloride in THF (0.20 mL, 1.0 M, 0.20 mmol) was added in one portion. The solution was warmed to room temperature and 10.0 mL of water and 10.0 mL of diethylether were added. The organic layer was separated and washed twice with 20 mL of water and dried over magnesium sulfate. After filtration, the filtrate was concentrated in vacuo to yield 5-trimethylstannyl-4,4'-didodecyl-2,2'-bithiophene (29, 0.103 g, 90% yield) as a yellow oil. $^1$H NMR (CDCl$_3$): δ 0.84-1.64 (m, 46H), 2.58 (m, 4H), 6.77 (s, 1H), 6.99 (s, 1H), 7.13 (s, 1H).

Example 29

Preparation of indenofluorenedionebithiophene copolymer (IFDKT2)

2,5-Bis(tributylstannyl)thiophene (0.095 g, 0.128 mmol), 2,8-dibromo-5,11-didodecylindeno[1,2-b]fluorene-6,12-dione 5 (0.100 g, 0.128 mmol) and Pd(PPh$_3$)$_4$ (10 mg) in anhydrous toluene (5 mL) were heated at 110° C. with stirring under nitrogen for two days. The reaction mixture was cooled to room temperature and poured into methanol (300 mL). The resulting solids were subjected to Soxhlet extraction for two days in acetone and dissolved in chlorobenzene by Soxhlet extraction. Methanol was added and the product precipitated, which was collected to give the tetraphenylenedimalononitrile copolymer as a black solid (78.0 mg, 40%). RT GPC: M$_n$=9400 g mol$^{-1}$, M$_w$=11,200 g mol$^{-1}$, and D=1.20 (against PS standard); and Elemental analysis: C, 79.65; H, 7.50.

Example 30

Preparation of tetraphenylenedionebithiophene copolymer (TPDKT2)

2,5-Bis(tributylstannyl)bithiophene (0.143 g, 0.193 mmol), dibromotetraphenylenedione 9 (0.145 g, 0.193 mmol), and Pd(PPh$_3$)$_4$ (25 mg) in anhydrous toluene (10 mL) were heated at 110° C. with stirring under nitrogen for two days. The reaction mixture was cooled to room temperature and was poured into methanol (300 mL). The resulting solids were subjected to Soxhlet extraction in acetone for two days and dissolved in chlorobenzene by Soxhlet extraction. Methanol was added and the solids was collected to give the tetraphenylenedimalononitrile copolymer as a black solid (100 mg, 35%). RT GPC: M$_n$=6200 g mol$^{-1}$, M$_w$=9,400 g mol$^{-1}$, and D=1.52 (against PS standard); and Elemental analysis: C, 81.20; H, 7.10.

Example 31

Preparation of IFDMT4-12

To a 20 mL microwave glass vial was charged 2,8-di-(5-bromo-3-dodecylthien-2-yl)-indeno[1,2-b]fluorene-6,12-dimalononitrile (22) (100.0 mg, 0.096 mmol), 4,4'-didocecyl-5,5'-trimethylstannyl-2,2'-bithiophene (26; 80.0 mg, 0.096 mmol), tris(dibenzylideneacetone)dipalladium(0) (2.0 mg, 0.002 mmol), tri-(o-tolylphosphine) (2.5 mg, 0.008 mmol) and chlorobenzene (2.0 mL). The glass vial was purged with nitrogen, sealed, and heated in a microwave reactor. A temperature ramp was used such that the vial was heated with stirring at 140° C. for 120 seconds, at 160° C. for 120 seconds, and at 180° C. for 900 seconds. The power was 300 W during the reaction. After cooling to 50° C., the crude product was precipitated with methanol. The precipitate was collected by filtration, dissolved in THF, filtered through a 0.45 μm filter, and precipitated with methanol again. This dissolution/precipitation procedure was repeated three more times. The final polymer was subjected to Soxhlet extraction (with acetone and methanol) and dried overnight at 100° C. to give product IFDMT4-12 as a dark-colored solid (79.6 mg, 60% yield). $^1$H NMR (CDCl$_3$): δ 0.88-1.62 (br m, 92H), 2.57 (br, 4H), 2.74 (br, 4H), 7.00 (br, 2H), 7.42 (br, 2H), 7.65 (br, 4H), 8.55 (br, 4H) ppm; Elemental Analysis: C, 78.87; H, 8.42; N, 3.65. and GPC (HT in TCB) M$_w$=23273 g/mol, M$_n$=6685 g/mol, PDI=3.48.

Example 32

Preparation of tetraphenylenedione-fluorene copolymer (TPDKF)

A mixture of compound 9 (150.0 mg, 0.173 mmol), 2,2'-(9,9-dioctyl-9H-fluorene-2,7-diyl)bis(4,4,5,5-tetramethyl-1,3,2-dioxaborolane) (131.0 mg, 0.173 mmol), and Aliquat 336 (0.02 g) was degassed 3 times with N$_2$ before 3.0 mL of dry toluene was added. Tetrakis(triphenylphosphine)palladium (10 mg, 0.005 mmol) in an aqueous sodium carbonate solution (0.6 mL, 2M, deaerated for 2 hours) was added under N$_2$. The mixture was stirred vigorously and heated at the refluxing temperature for 2 days. The highly viscous reaction mixture was poured into a boiling methanol (30 mL) to precipitate an orange polymer. The polymer was collected by filtration and washed with acetone, methanol, water, and dried under vacuum at 60° C. overnight. The polymer was dissolved in THF (170 mg in 9 mL of THF) and reprecipitated with 40 mL of acetone twice to give 140 mg of TPDKF as an orange polymer (45%); and Elemental analysis: C, 87.30; H, 9.57; O, 2.58.

Example 33

Preparation of tetraphenylenedimalononitrile homopolymer (TPDC)

Ni(COD)$_2$ (211 mg, 0.746 mmol), 2,2'-bipyridyl (116.5 mg, 0.746 mmol), and 1,5-cyclooctadiene (COD, 0.091 mL, 0.746 mmol) were mixed in dry DMF (5 mL) and dry toluene (1.6 mL) in a glove box. The purple solution was heated to 80° C. for 30 minutes. Dibromotetraphenylenedimalononitrile 10 (300 mg, 0.311 mmol) in 6 mL of dry toluene was added. The solution was stirred under argon for 1 day and bromobenzene (1.0 mL) was added. The reaction mixture was poured in methanol and filtered. The resulting solids were subjected to Soxhlet extraction for 2 days in acetone, dissolved in THF, precipitated in methanol (3 times), and filtered to give the tetraphenylenedimalononitrile homopolymer as a yellow solid (125 mg, 50%). RT GPC: Mn=8037 g mol$^{-1}$, Mw=12,455 g mol$^{-1}$, and D=1.55 (against PS standard); and Elemental analysis: C, 83.85; H, 7.63; N, 6.77.

Example 34

Preparation of tetraphenylenedimalononitrilebithiophene copolymer (TPDCT2)

2,5-Bis(tributylstannyl)bithiophene (0.45 mmol, 0.30 g), dibromotetraphenylenedimalononitrile 10 (0.45 mmol, 0.43 g), and Pd(PPh$_3$)$_2$Cl$_2$ (40 mg) in anhydrous toluene (10 mL) were heated at 80° C. with stirring under nitrogen for two days. The reaction mixture was cooled to room temperature and poured into methanol (300 mL). The resulting solids were subjected to Soxhlet extraction for two days in acetone, dissolved in chloroform and precipitated from methanol (3 times). The resulting solids were filtered to give the tetraphenylenedimalononitrile copolymer as a black solid (210 mg, 50%). RT GPC: M$_n$=8100 g mol$^{-1}$, M$_w$=10,500 g mol$^{-1}$, and D=1.30 (against PS standard); and Elemental analysis: C, 81.95; H, 6.70; N, 6.60.

Example 35

Cyclic Voltammetry

Figure 1B:
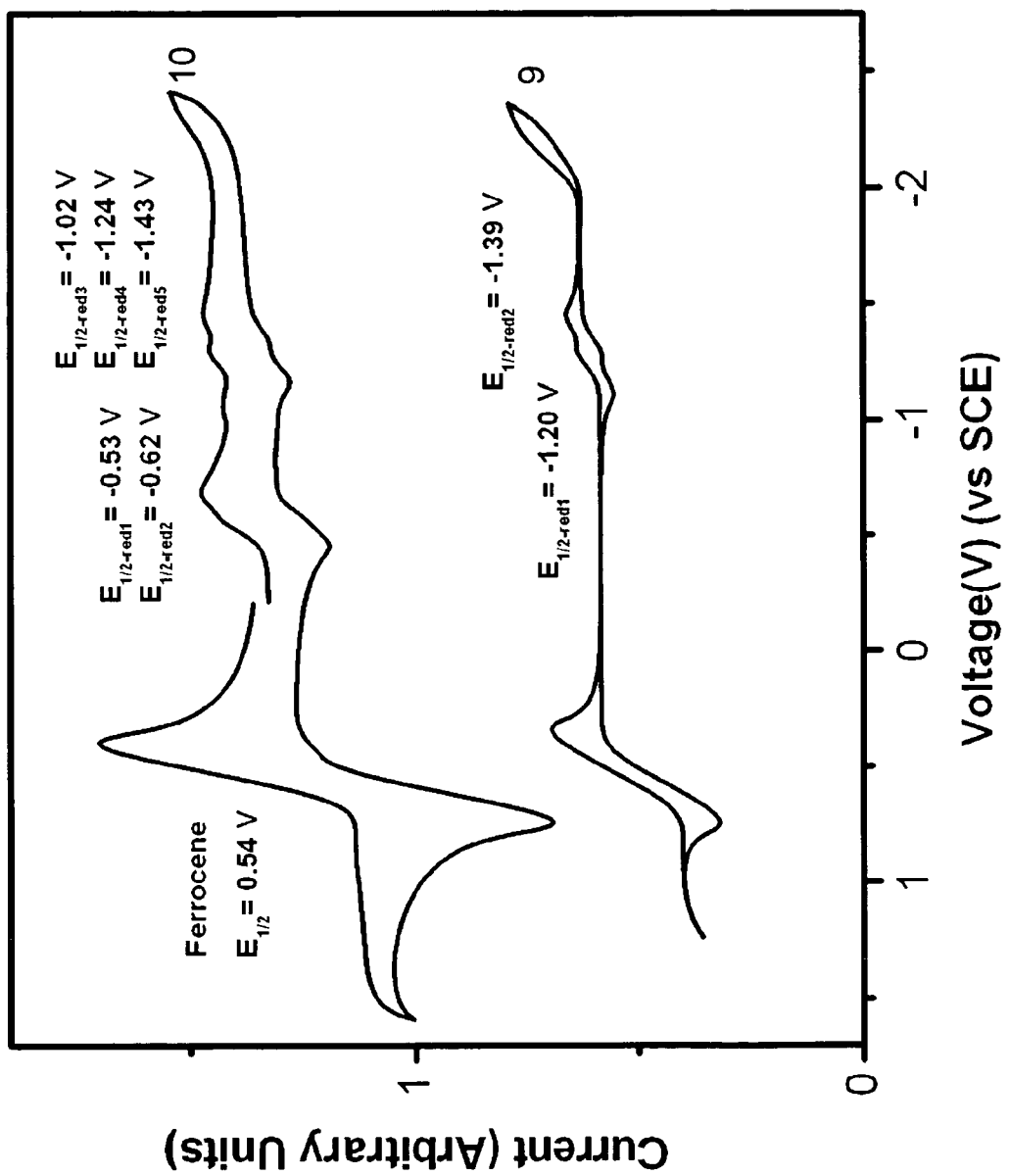
FIG. 1B shows cyclic voltammograms of exemplary compounds of the present teachings (9 and 10) in THF. (Ferrocene was used as an internal standard with its peak adjusted to 0.54 V).
Figure 8:
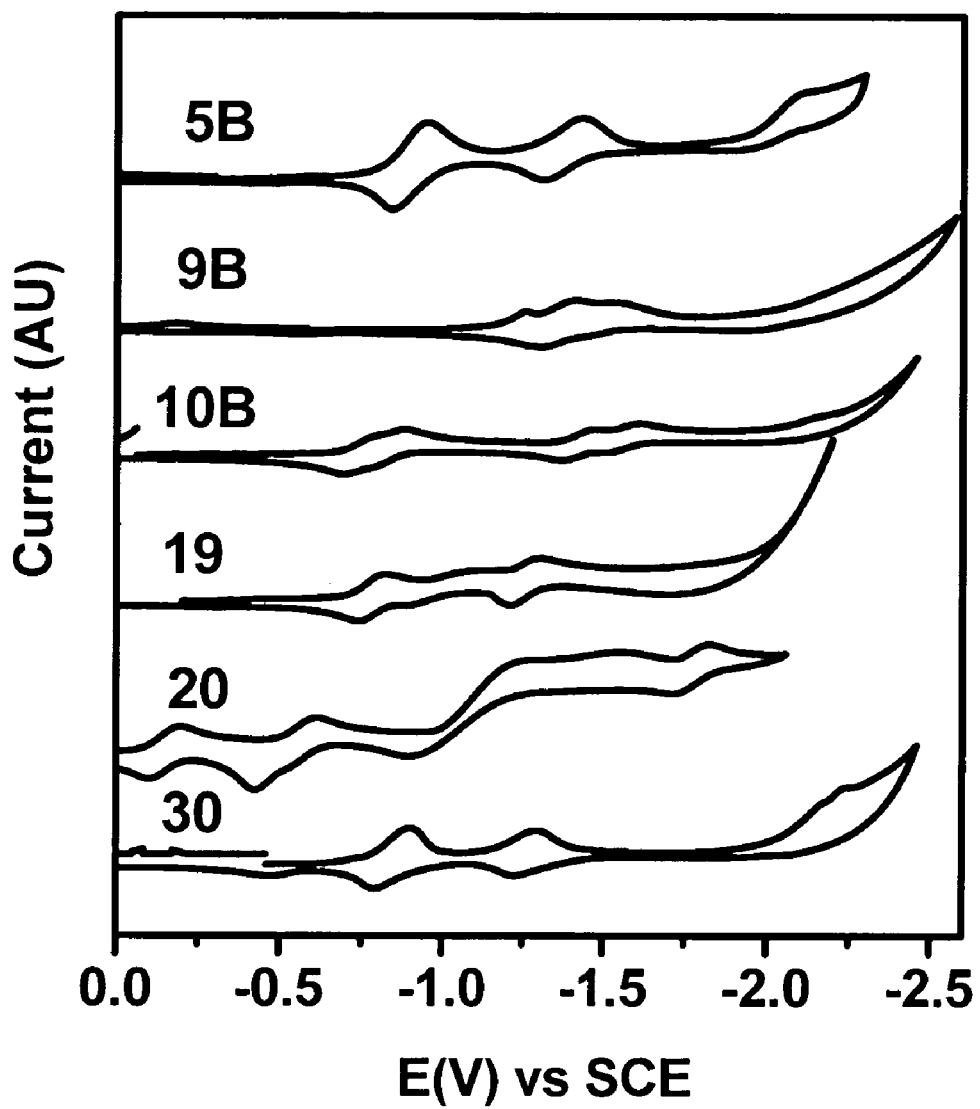
FIG. 8 shows cyclic voltammograms of exemplary compounds of the present teachings (5B, 9B, 10B, 19, 20, and 30) in THF. (Ferrocene was used as an internal standard with its peak adjusted to 0.54 V).

The cyclic voltammograms for compounds 4, 5, and 6, for compounds 9 and 10, and for compounds 5B, 9B, 10B, 19, 20, and 30 in THF are shown in FIG. 1A, FIG. 1B, and FIG. 8, respectively. The corresponding data are presented in Table 1. Reversible reductions were observed for all of the studied compounds.

TABLE 1

Electrochemical Properties of compound 4, 5, 6, 9, 10, 5B, 9B, 10B, 19, 20, 30 and 31 and the corresponding estimated frontier molecular orbital energies

| Com. | $E_1^{1/2}$ (V) | $E_2^{1/2}$ (V) | $E_3^{1/2}$ (V) | LUMO$^a$ (eV) |
|---|---|---|---|---|
| 4 | −0.85 | −1.37 | — | 3.59 |
| 5 | −0.77 | −1.31 | — | 3.67 |
| 6 | −0.14 | −0.44 | −0.55, −1.01, −1.47, −1.85 | 4.30 |
| 9 | −1.20 | −1.39 | — | 3.24 |
| 10 | −0.53 | −0.62 | −1.02, −1.24, −1.43 | 3.91 |
| 5B | −0.89 | −1.38 | −2.04 | 3.55 |
| 9B | −1.25 | −1.36 | −1.51 | 3.19 |
| 10B | −0.72 | −0.82 | −1.41, −1.58 | 3.72 |
| 19 | −0.74 | −0.98 | −1.24 | 3.70 |
| 20 | −0.12 | −0.51 | −0.60, −1.77 | 4.32 |
| 30 | −0.86 | −1.27 | — | 3.58 |

$^a$The LUMO energy level is calculated as $E_1^{1/2}$ + 4.44 eV.

Example 36

UV-Vis Spectroscopy and Fluorescence Spectroscopy for Conjugated Monomers

Figure 2A:
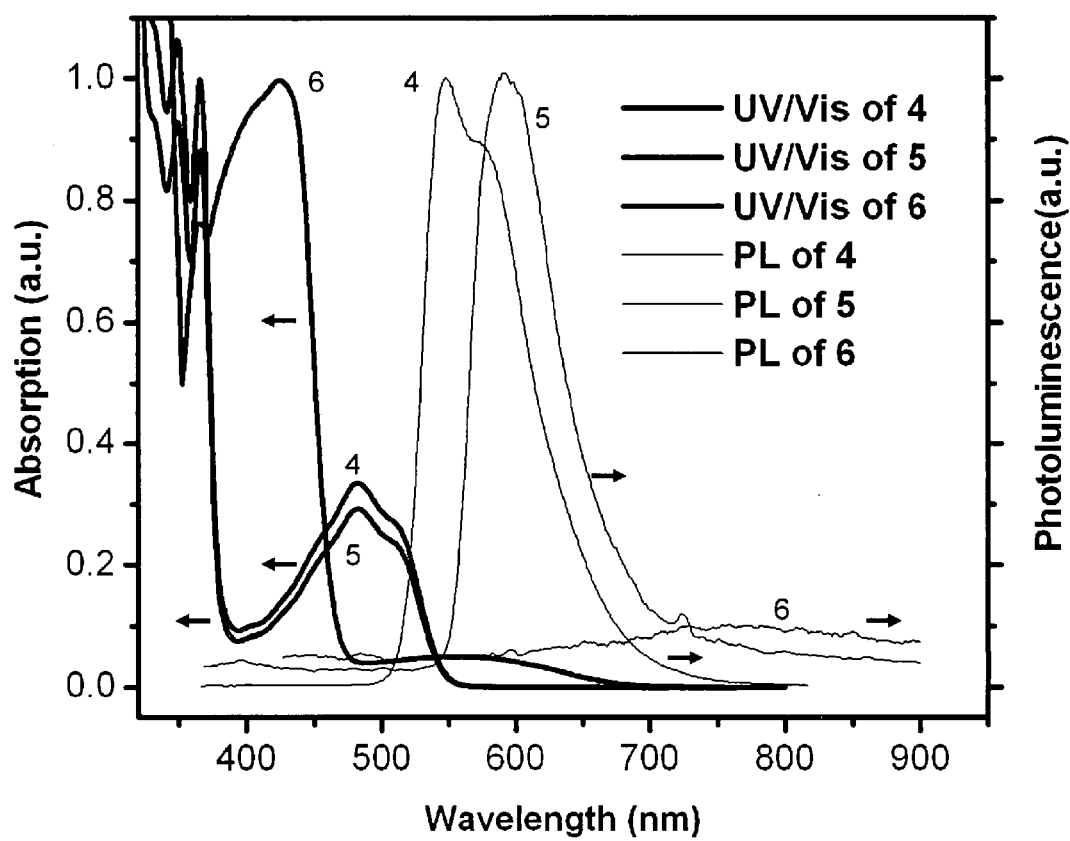
FIG. 2A shows ultraviolet-visible (UV-Vis) and photoluminescence (PL) spectra of exemplary compounds of the present teachings (4, 5, and 6) in THF.
Figure 2B:
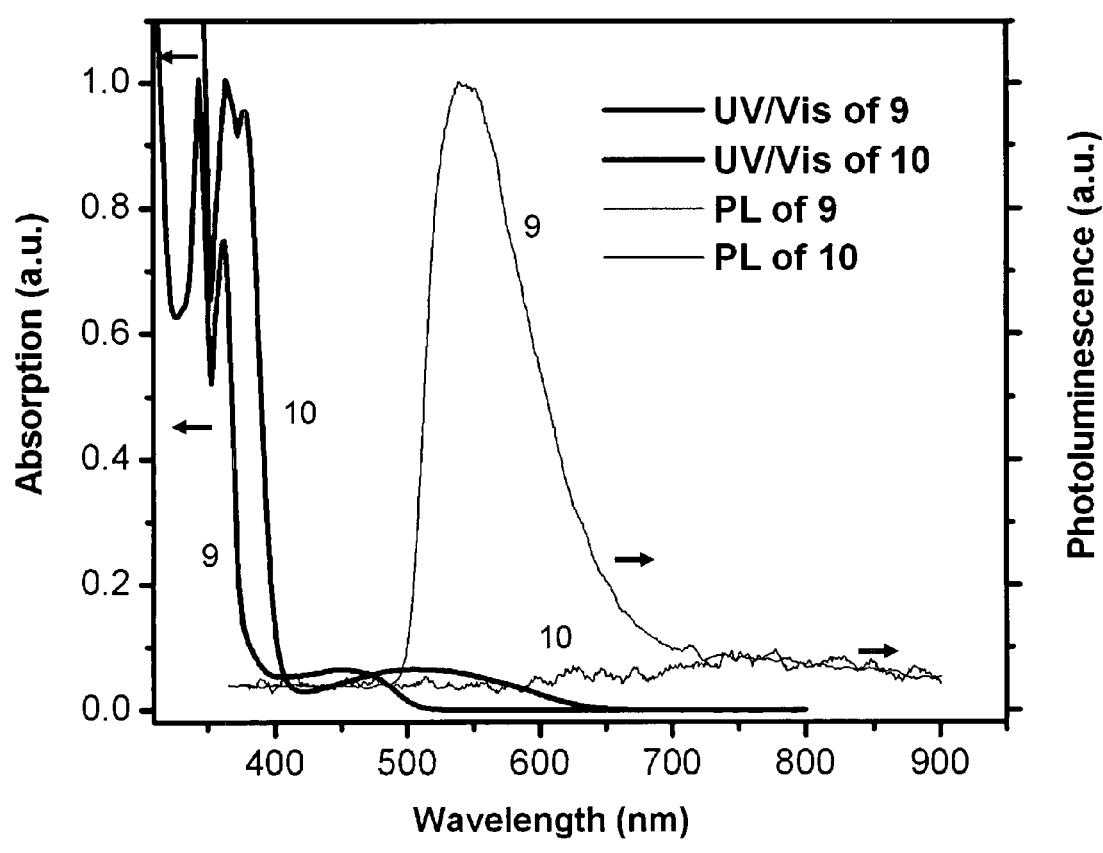
FIG. 2B shows UV-Vis and PL spectra of exemplary compounds of the present teachings (9 and 10) in THF.
Figure 9:
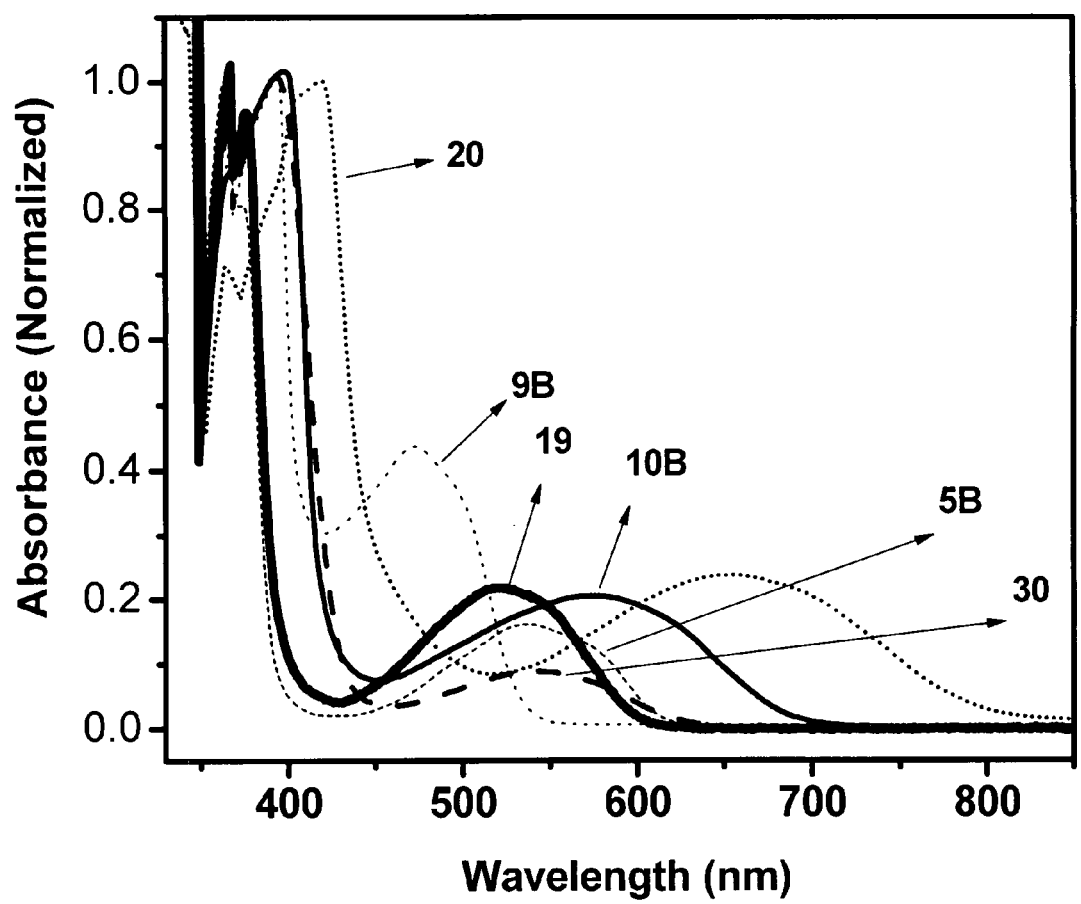
FIG. 9 shows ultraviolet-visible (UV-Vis) spectra of exemplary compounds of the present teachings (5B, 9B, 10B, 19, 20, and 30) in THF.
Figure 10:
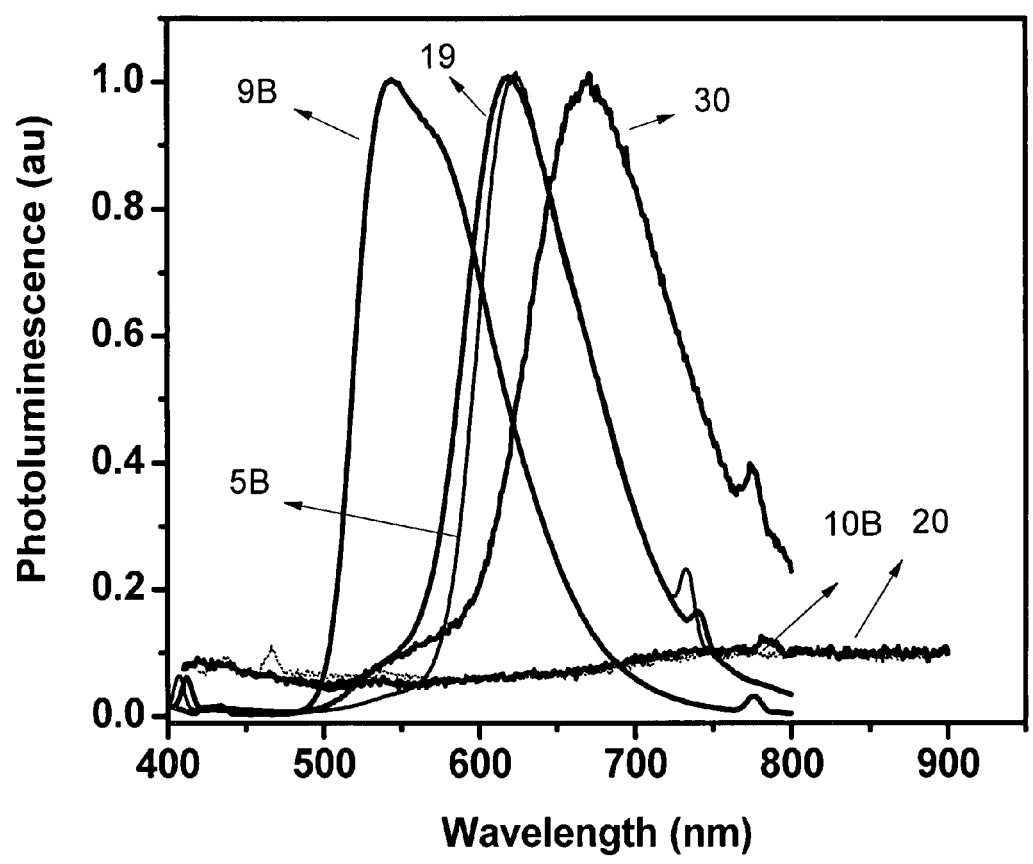
FIG. 10 shows photoluminescence (PL) spectra of exemplary compounds of the present teachings (5B, 9B, 10B, 19, 20, and 30) in THF.

The UV-Vis absorption and photoluminescence spectra of compounds 4, 5, and 6, and for compounds 9 and 10 in THF are shown in FIG. 2A and FIG. 2B, respectively, and the UV-Vis absorption and photoluminescence spectra for compounds 5B, 9B, 10B, 19, 20, and 30 in THF are shown in FIG. 9 and FIG. 10. The corresponding data are presented in Table 2.

TABLE 2

Optical absorption properties of compounds 4, 5, 6, 9, 10, 5B, 9B, 10B, 19, 20, 30 and 31 and the corresponding estimated frontier molecular orbital energies

| Com. | $\lambda_{max}$ (nm) | $\lambda_{em}$ (nm) | $E_g^b$ (eV) | HOMO$^d$ (eV) |
|---|---|---|---|---|
| 4 | 366, 483$^c$ | 549 | 2.28 | 5.87 |
| 5 | 368, 484$^c$ | 590 | 2.28 | 5.95 |
| 6 | 426, 579 | 762$^e$ | 1.83 | 6.16 |
| 9 | 365, 455$^c$ | 540 | 2.44 | 5.68 |
| 10 | 378, 513 | 768$^e$ | 1.95 | 5.86 |
| 5B | 374, 537$^c$ | 623 | 2.02 | 5.54 |
| 9B | 394, 472$^c$ | 545 | 2.31 | 5.50 |
| 10B | 400, 576 | 785 | 1.80 | 5.52 |
| 19 | 377, 525$^c$ | 619 | 2..05 | 5.75 |
| 20 | 418, 653 | 780 | 1.52 | 5.84 |
| 30 | 394, 540$^c$ | 670 | 1.94 | 5.53 |

$^b$Band gaps are estimated from the low energy band edge of the UV-Vis spectrum.
$^c$n-$\pi^*$ transition due to carbonyl groups.
$^d$HOMO energy level is calculated as LUMO + $E_g$.
$^e$broad and weak emission peak.

Example 37

UV-Vis Spectroscopy and Cyclic Voltammetry for TPDC, TPDCT2, TPDKT2, IFDKT2, and IFDMT4-12

Figure 3A:
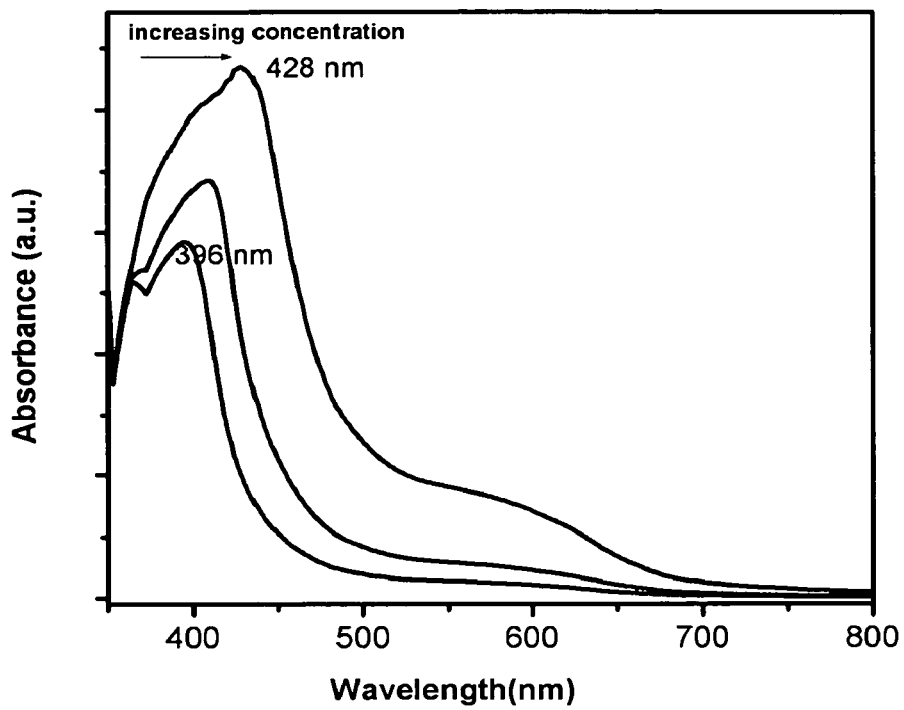
FIG. 3A shows a UV-Vis spectrum of an exemplary compound of the present teachings (homopolymer TPDC) in THF.
Figure 3B:
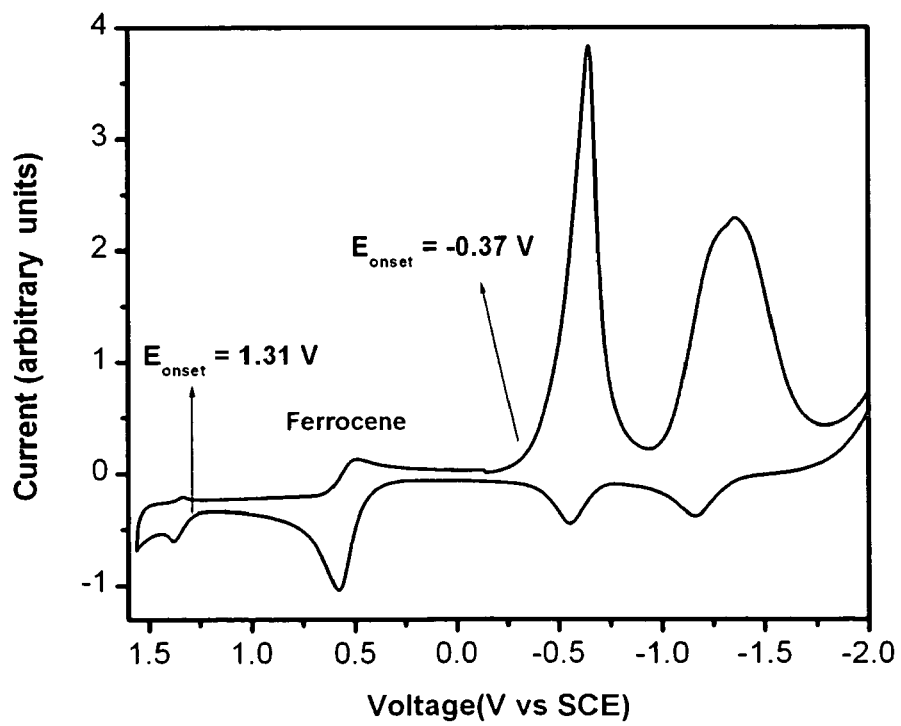
FIG. 3B shows a cyclic voltammogram of an exemplary compound of the present teachings (homopolymer TPDC) in thin film form.
Figure 4A:
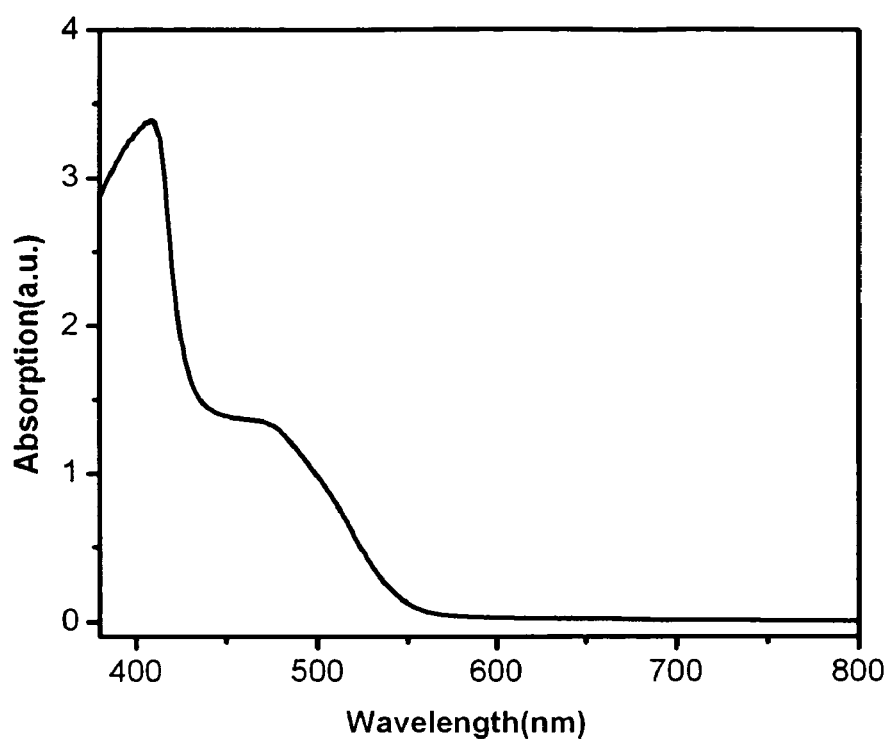
FIG. 4A shows a UV-Vis spectrum of an exemplary compound of the present teachings (copolymer TPDCT2) in THF.
Figure 4B:
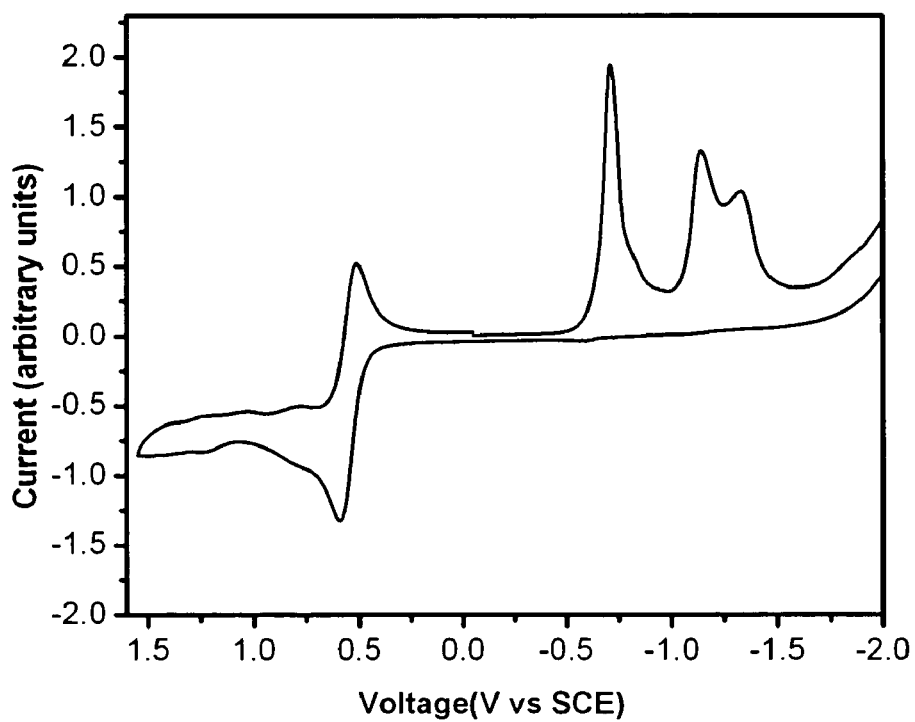
FIG. 4B shows a cyclic voltammogram of an exemplary compound of the present teachings (copolymer TPDCT2) in thin film form.

Electronic properties of the homopolymer TPDC and copolymers TPDCT2, TPDCT2, TPDKT2, IFDKT2, and IFDMT4-12 were investigated by UV-Vis spectroscopy in solution and by cyclic voltammetry in thin film forms (typical UV-Vis spectra and cyclic voltammograms shown as FIG. 3 and FIG. 4). The optical band gaps calculated from the low energy band edge of the UV-Vis spectrum are 1.80 eV, 1.75 eV, 1.90 eV, 1.85 eV, 1.36 eV for TPDC, TPDCT2, TPDKT2, IFDKT2, and IFDMT4-12, respectively. The absorption spectra of the homopolymer TPDC show a considerable redshift. In addition, a shoulder around 580 nm appears when the concentration of the polymer is increased.

The electrochemical characterization of the polymers was done on a Pt working electrode in acetonitrile and a polymeric thin film was used. Reversible reductions and oxidations were observed with onset reduction potentials of −0.37 V, −0.60 V, −0.90 V, −0.80 V, and −0.29 V along with onset oxidation potentials of 1.31 V, 1.12 V, 0.90 V, 0.98 V, and 1.07 V for TPDC, TPDCT2, TPDKT2, IFDKT2, and IFDMT4-12, respectively. The electrochemical band gaps were calculated as 1.80 eV, 1.78 eV, 1.36 eV, 1.68 eV and 1.72 eV for TPDKT2, IFDKT2, IFDMT4-12, TPDC, and TPDCT2, respectively, which is in good agreement with the optical band gaps. The LUMO energy levels were estimated to be about 4.07 eV, 3.84 eV, 3.54 eV, 3.64 eV, 4.15 eV for TPDC, TPDCT2, TPDKT2, IFDKT2, and IFDMT4-12, respectively, considering the vacuum energy level of standard calomel electrode as 4.44 eV.

Example 38

FET Device Fabrication and Measurement

Figure 5A:
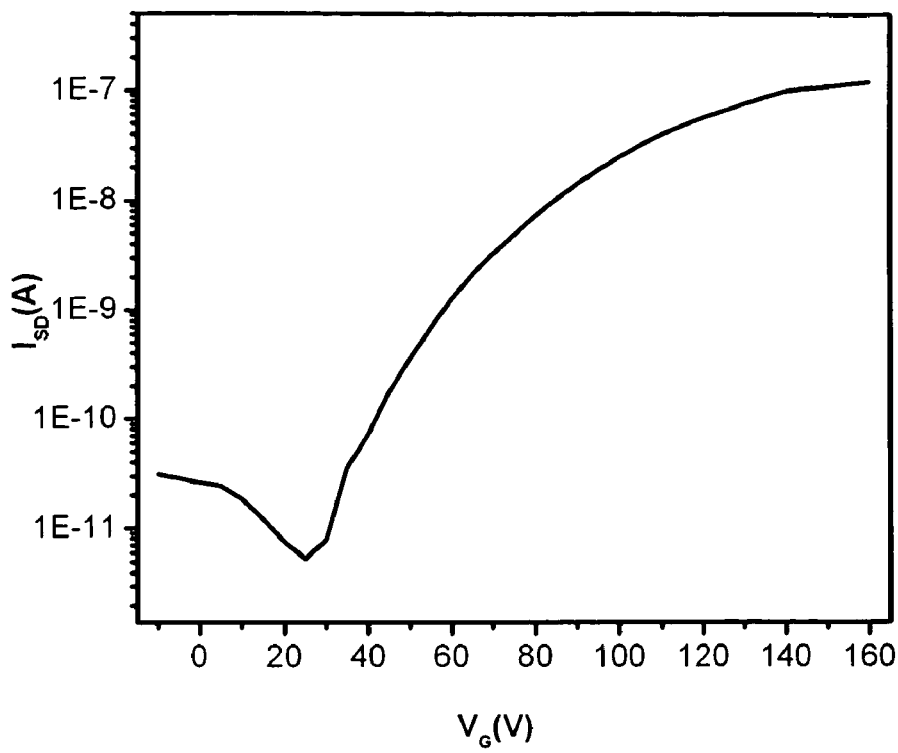
FIG. 5A is a representative transfer plot of an organic field effect transistor (OFET) device that includes an exemplary compound of the present teachings (10).
Figure 5B:
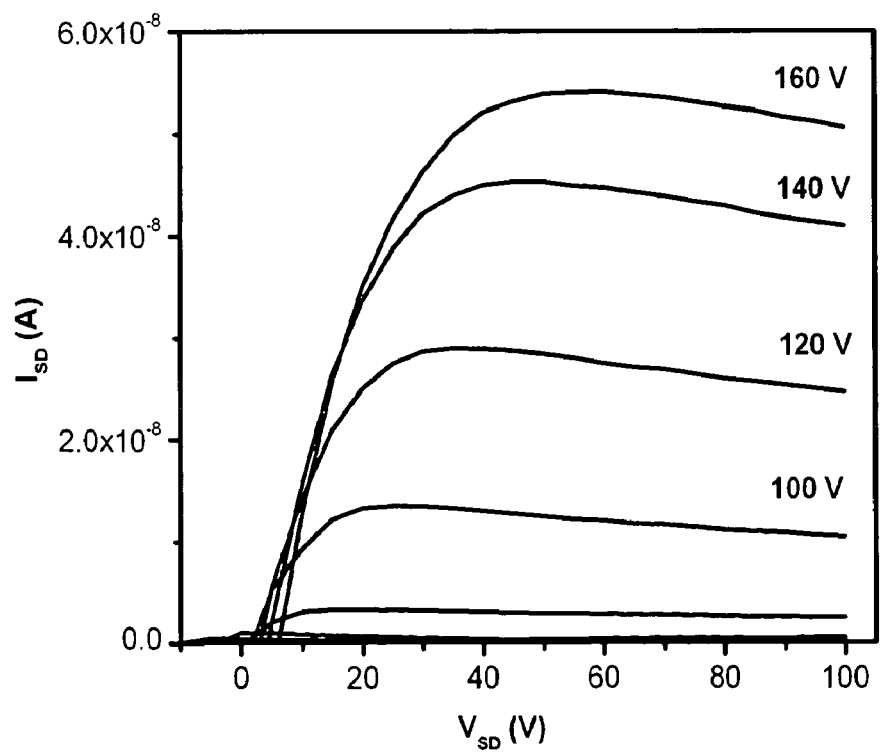
FIG. 5B is a representative output plot of an OFET device that includes an exemplary compound of the present teachings (10).
Figure 5C:
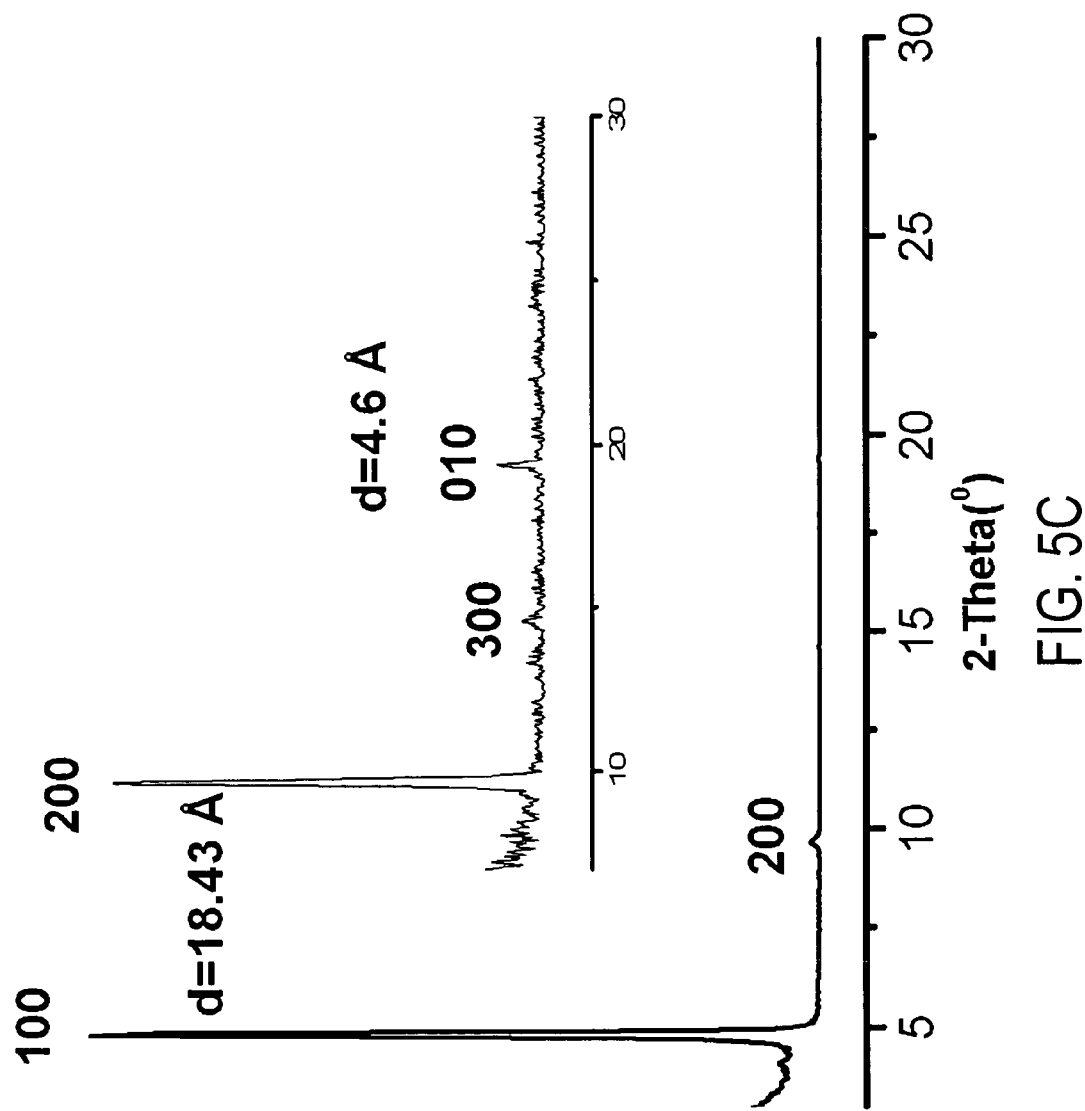
FIG. 5C shows a thin-film x-ray diffraction (XRD) of an OFET device that includes an exemplary compound of the present teachings (10).

OTFT devices were fabricated on low resistivity n-type silicon wafers, using thermally grown $SiO_2$ (300 nm), HMDS-treated and OTS-treated $SiO_2$ as the dielectric, in top-contact geometries. The active semiconducting layer that includes compound 10 was deposited by vacuum vapor deposition. X-Ray diffraction indicates that vapor-deposited films are highly crystalline. The progression of the Bragg reflections corresponds to the d-spacing of 18.4 Å and a π-π stacking distance of 4.6 Å. For top-contact devices, gold contacts were patterned on top of the films using shadow masks, giving channel lengths from about 25 μm to about 100 μm and widths from about 500 μm to about 2000 μm. OFET characterization was performed under vacuum. The output and transfer characteristics and thin-film XRD are shown in FIG. 5.

An electron mobility of 0.001-0.002 $cm^2/V$ s with an $I_{on}/I_{off}$ of $4\times10^5$ was observed for films that were deposited at a substrate temperature of 90° C. on OTS-treated substrates. Lower electron mobilities of $\sim10^{-5}$-$10^{-6}$ $cm^2/V$ s (with $I_{on}/I_{off}$ 10-100) were observed for films deposited at room temperature on HMDS-treated and non-treated substrates.

Figure 6A:
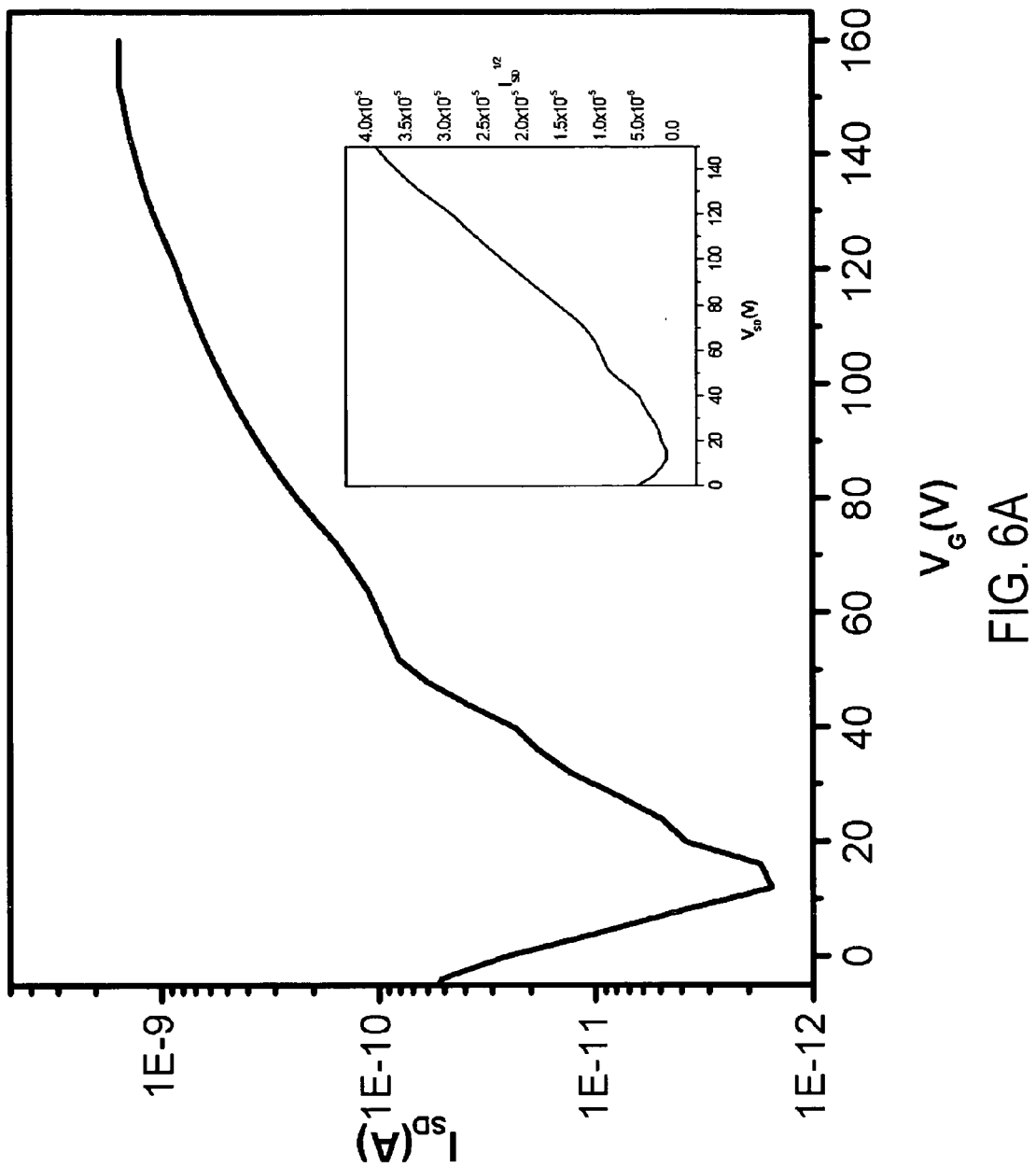
FIG. 6A is a representative transfer plot of an OFET device that includes an exemplary compound of the present teachings (polymer TPDC).
Figure 6B:
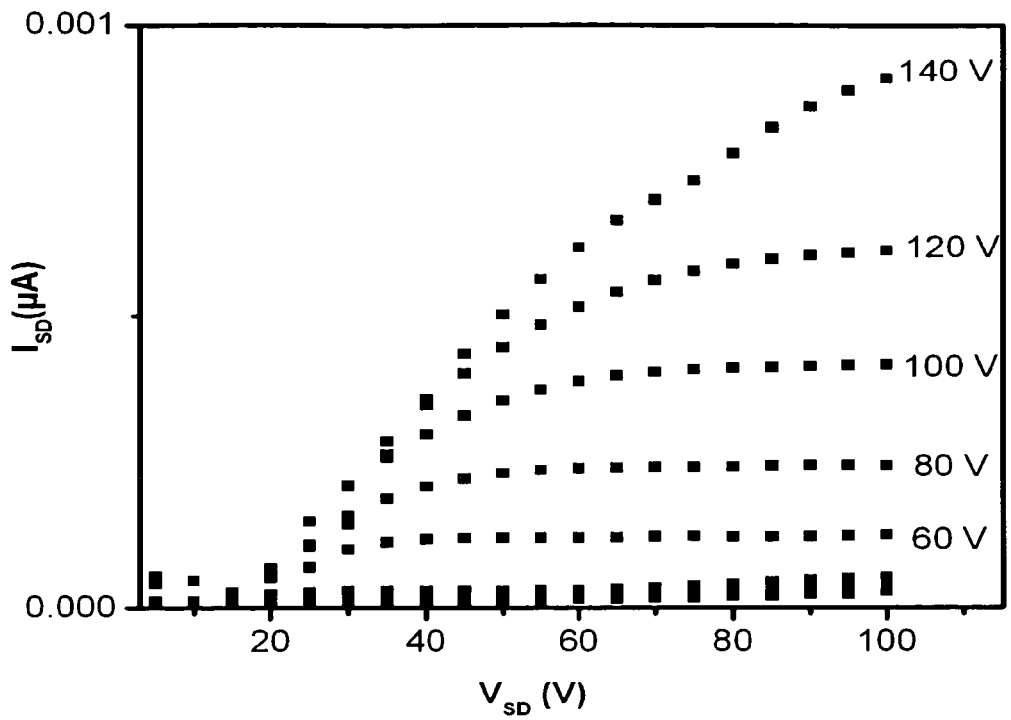
FIG. 6B is a representative output plot of an OFET device that includes an exemplary compound of the present teachings (polymer TPDC).

Polymer thin films were prepared by spin-coating and drop-casting from polymer solutions in chloroform and THF on n-doped $Si/SiO_2$ substrates. HMDS- or OTS-treated and non-treated substrates were used. An electron mobility of $0.8\times10^{-5}$ $cm^2/V$ s with an $I_{on}/I_{off}$ of $2\times10^3$ was observed under vacuum for FETs fabricated with films of homopolymer TPDC that were deposited from chloroform (2 mg/mL for drop-casting and 10 mg/mL for spin-coating) and annealed at 100° C. (FIG. 6).

Figure 7A:
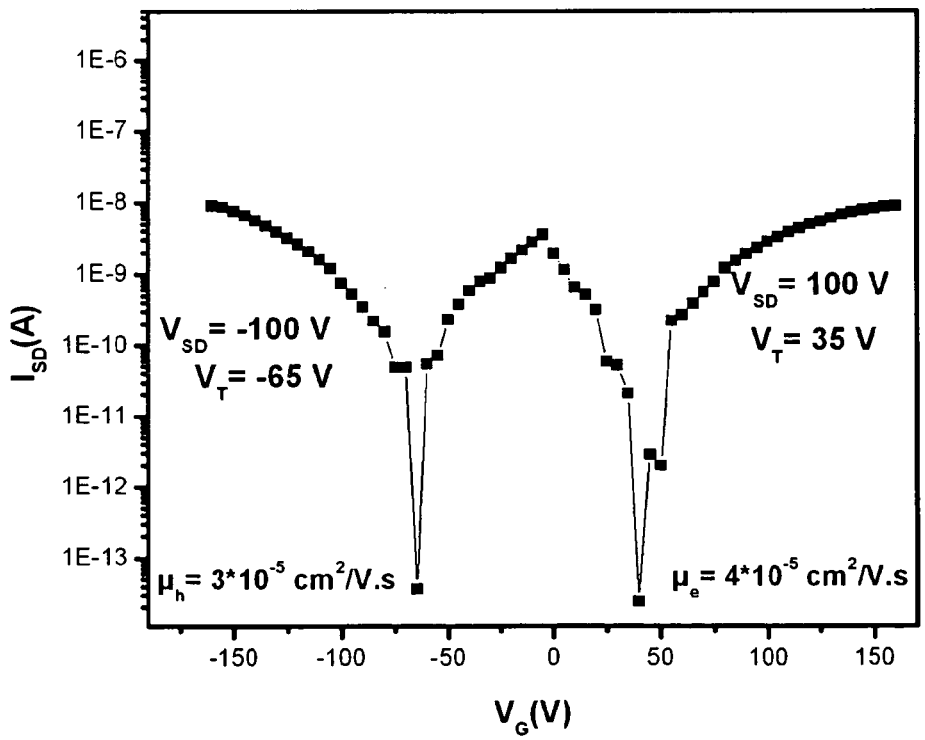
FIG. 7A is a representative ambipolar transfer plot of an OFET device that includes an exemplary compound of the present teachings (copolymer TPDCT2).
Figure 7B:
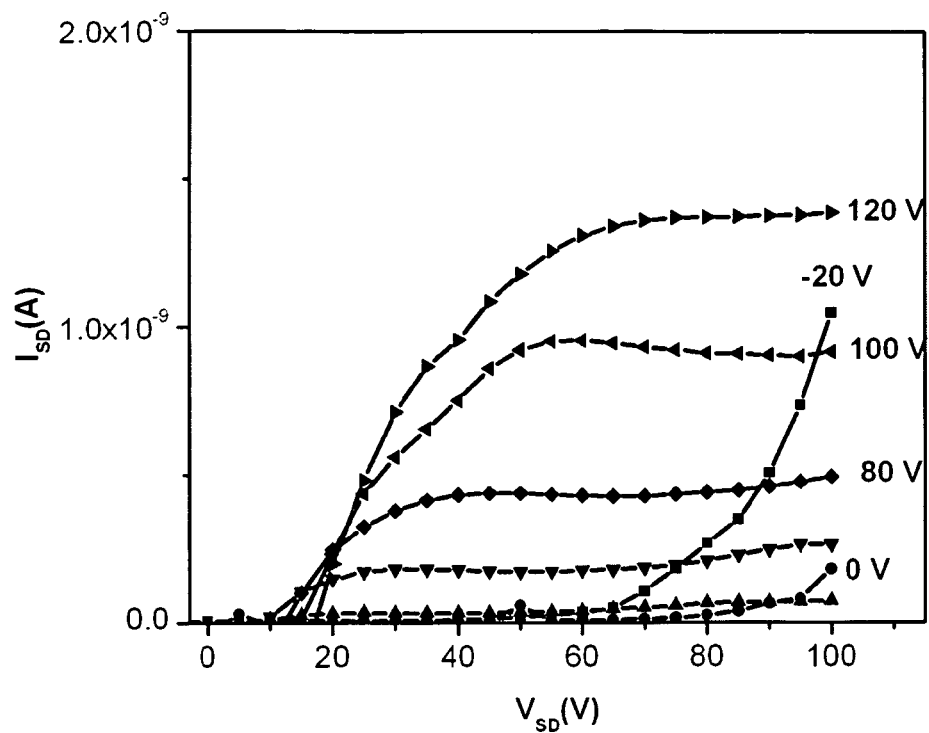
FIG. 7B is a representative n-type output plot of an OFET device that includes an exemplary compound of the present teachings (copolymer TPDCT2).
Figure 7C:
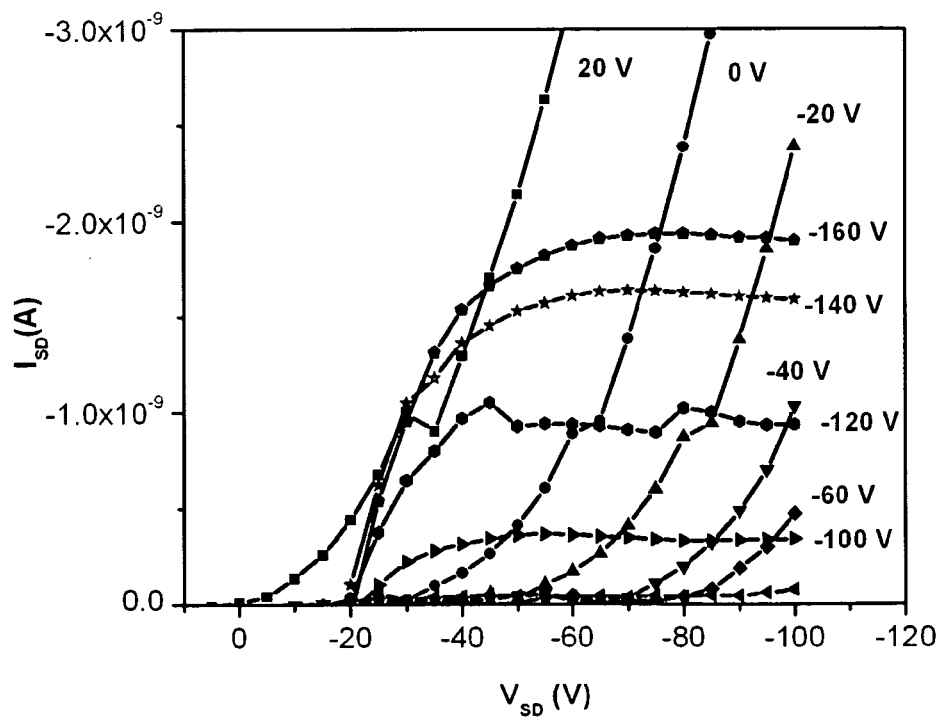
FIG. 7C is a representative p-type output plot of an OFET device that includes an exemplary compound of the present teachings (copolymer TPDCT2).

Copolymer TPDCT2 exhibited an electron mobility up to $4\times10^{-5}$ $cm^2/V$ s with an $I_{on}/I_{off}$ of $\sim10^4$ when it was deposited from a THF solution. Due to its very small band gap and higher HOMO energy level compared to TPDC, ambipolar behavior was also observed on OTS-treated substrates with an electron mobility of $4\times10^{-5}$ $cm^2/V$ s ($I_{on}/I_{off}$ of $\sim10^4$) and a hole mobility of $3\times10^{-5}$ $cm^2/V$ s ($I_{on}/I_{off}\sim10^4$) (FIG. 7). The threshold voltages were 35 V for n-type semiconducting behavior and −65 V for p-type semiconducting behavior. Without wishing to be bound by any particular theory, the high threshold voltage and non-ohmic behavior in the p-type output plot is believed to be possibly due to a high injection barrier of 0.5 eV for holes, which in turn can be due to the low-lying HOMO energy level (−5.6 eV) compared to gold Fermi level (−5.1 eV).

Figure 11A:
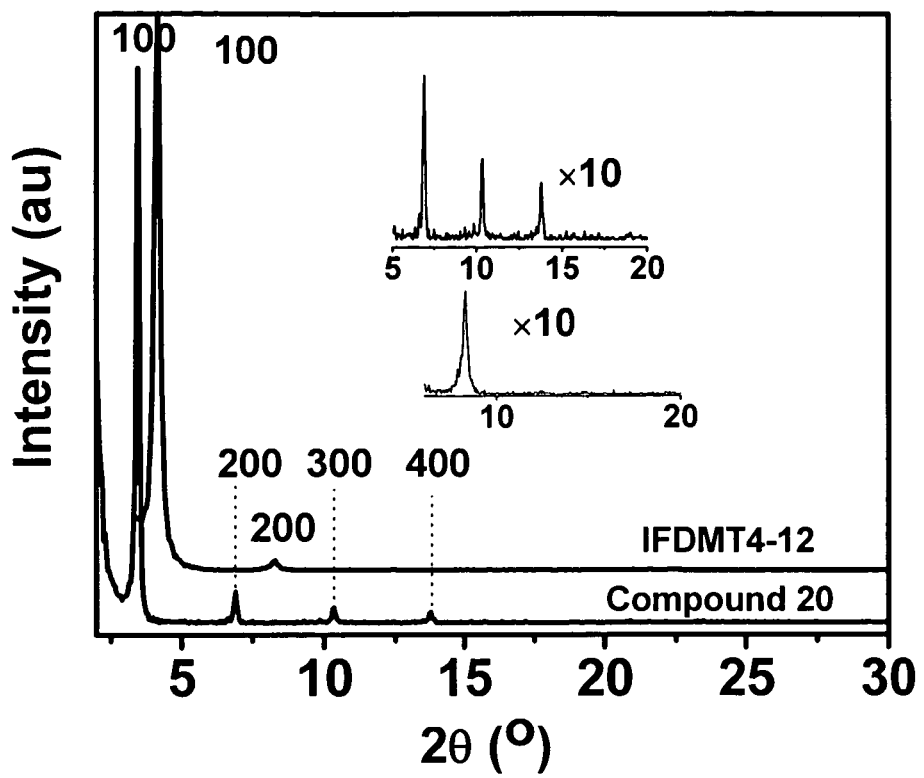
FIGS. 11A and 11B show thin-film x-ray diffractions (XRD) of two OFET devices each of which includes an exemplary compound of the present teachings (20 and IFDMT4-12).
Figure 11B:
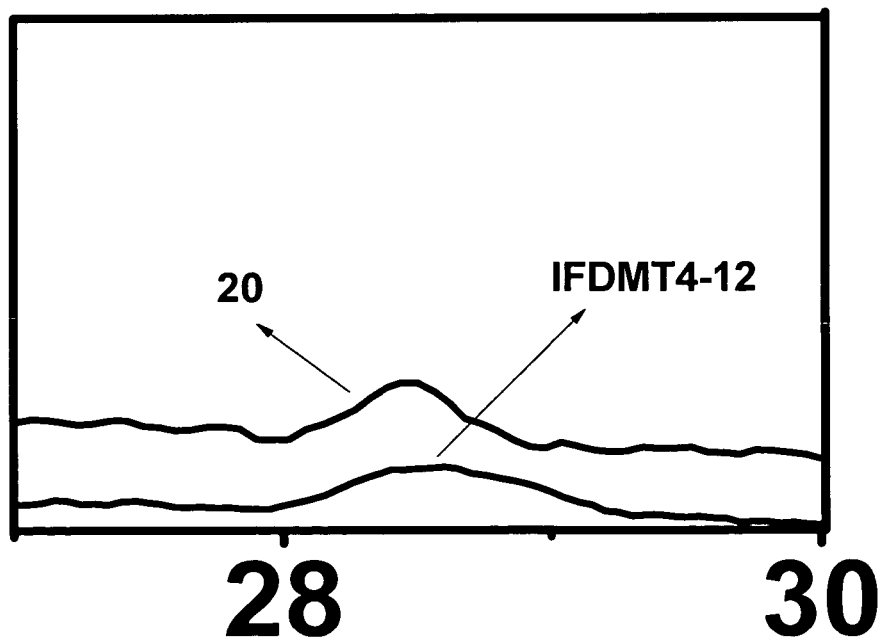
Figure 20:
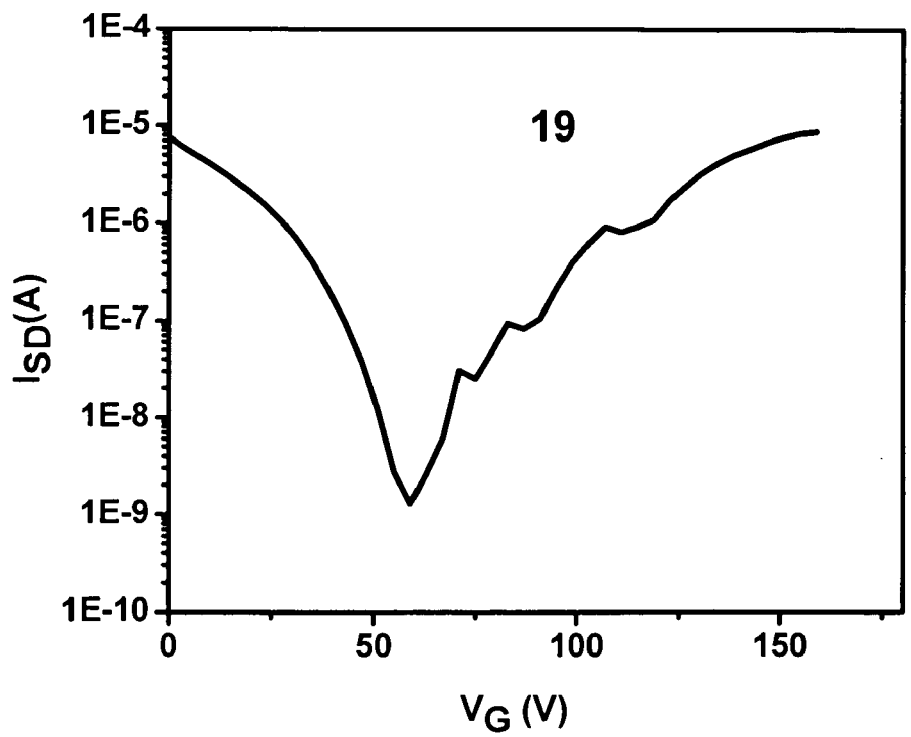
FIG. 20 is a representative n-type output plot of an OFET device that includes an exemplary compound of the present teachings (19).

Top-contact FETs were fabricated by spin-coating 20 or IFDMT4-12 solutions in $CHCl_3$ (5.0 mg/mL) on OTS (octadecyltrichlorosilane) treated $p^+$-$Si/SiO_2$(300 nm) substrates. The semiconductor films (60-65 nm) were annealed at 150° C. for 30 minutes under vacuum, followed by Au electrode (50 nm) deposition. Thin-film microstructural order was assayed by out-of plane θ-2θ XRD and grazing-incidence X-ray diffraction (GIXRD) scans. As shown in FIG. 11A, 20 and IFDMT4-12 thin films are highly crystalline, exhibiting Bragg reflections up to the fourth (400) and second (200) order, respectively. Primary reflections are observed at 2θ=3.46° (d-spacing=25.6 Å) for 20 and at 2θ=4.12° (d-spacing=21.4 Å) for polymer IFDMT4-12. These data are consistent with well-organized lamellar microstructures having the common preferential molecular/chain "edge-on" orientation relative to the substrate surface. The assigned π-π stacking repeat distance is 3.1 Å (2θ=28.5°, as shown in FIG. 11B), which is significantly smaller than typical observation for oligo-/poly-thiophenes (3.4 Å-3.8 Å).

Figures 12, 13:
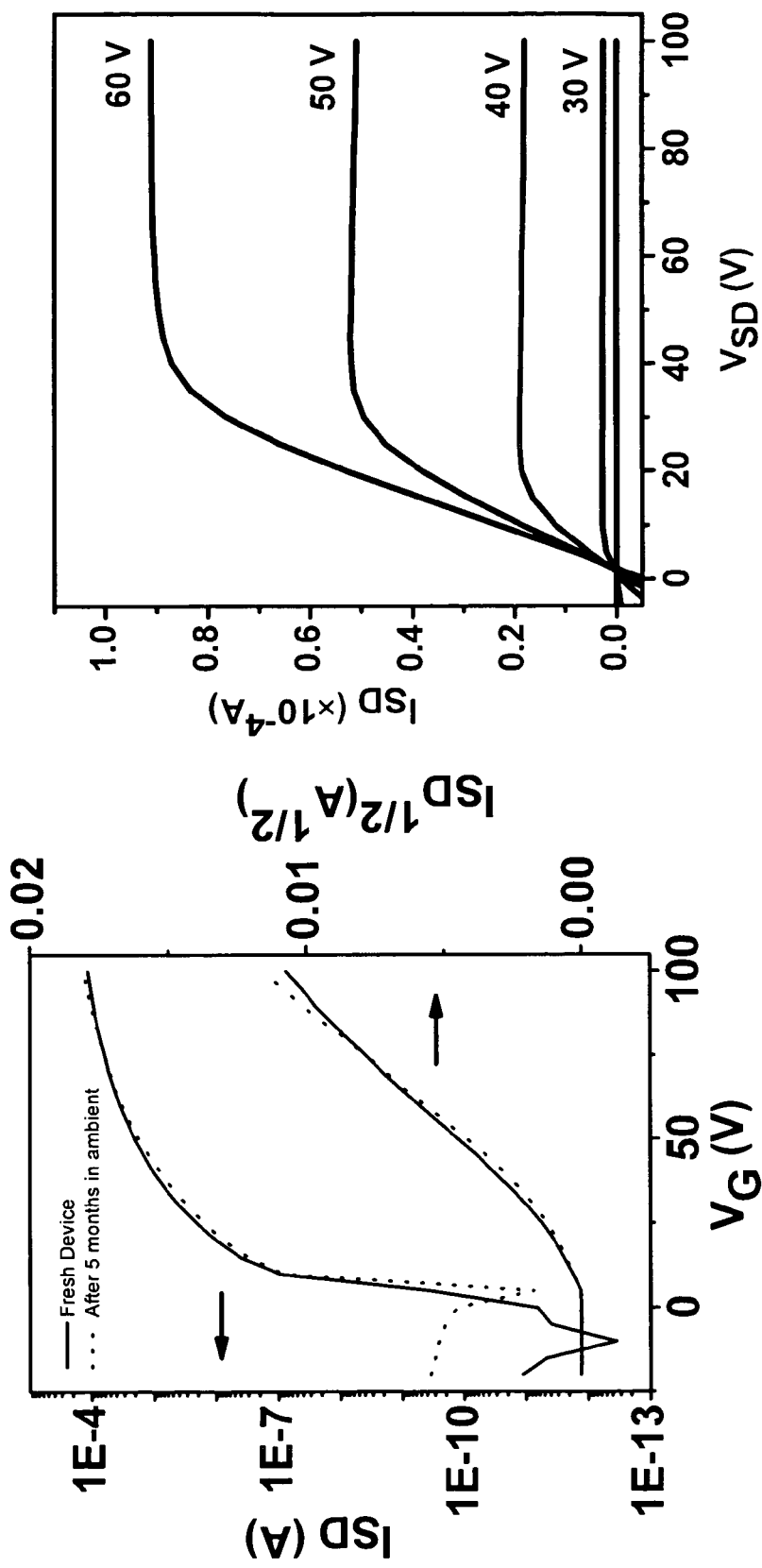
FIG. 12 is a representative transfer plot of an OFET device that includes an exemplary compound of the present teachings (20).
FIG. 13 is a representative output plot of an OFET device that includes an exemplary compound of the present teachings (20).
Figure 14:
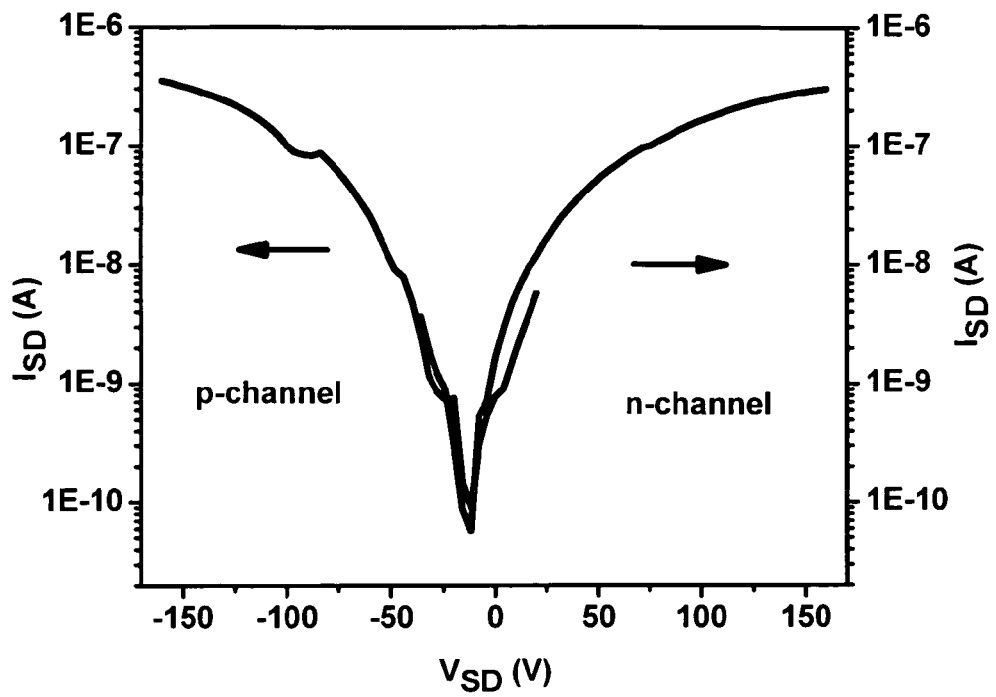
FIG. 14 is a representative ambipolar transfer plot of an OFET device that includes an exemplary compound of the present teachings (copolymer IFDMT4-12).

The device characteristics of these FETs were measured in ambient and typical transfer and output plots for 20 are shown in FIG. 12 and FIG. 13. These devices exhibit n-channel property with $\mu_e$=0.10-0.16 $cm^2V^{-1}s^{-1}$, $I_{on}/I_{off}$=$10^7$-$10^8$, and $V_T$=0~+5 V. In addition, these devices exhibit negligible variations in TFT characteristics after 5 months storage in air without exclusion of light or humidity. Furthermore, IFDMT4-12-based FETs are ambipolar in ambient and exhibit similar electron and hole mobilities ($\sim2\times10^{-4}$ $cm^2V^{-1}s^{-1}$) and $I_{on}/I_{off}$ ratios ($\sim10^4$) with $V_T$'s of ~+5 V (n-channel) and ~−10 V (p-channel) (FIG. 14). It should be noted that IFDMT4-12 is the first example of an air-stable, highly soluble ambipolar semiconducting polymer. It should also be noted that the unique electronic structure of the present polymers provides a very small band gap (1.36 eV), rendering the HOMO level (−5.51 eV) accessible for hole injection by Au contacts, thus enhancing p-channel operation. Without wishing to be bound by any particular theory, the observed high mobility for 20 probably reflects a combination of enhanced intermolecular π-orbital overlap, highly textured thin films, and large film grain sizes. Furthermore, without wishing to be bound by any particular theory, the preferential "edge-on" molecular orientation favors in-plane source-to-drain (S→D) transport. Without wishing to be bound by any particular theory, the excellent air-stability of 20 and IFDMT4-12 is likely related to the low LUMO energies (−4.15 and −4.32 eV).

Figure 15:
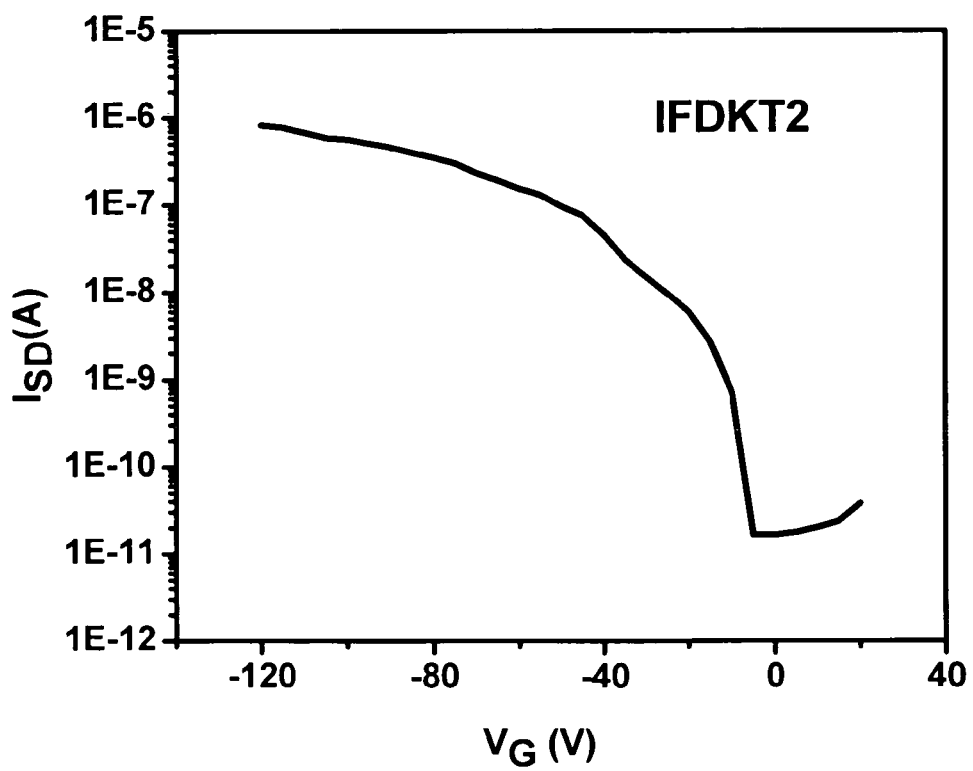
FIG. 15 is a representative transfer plot of an OFET device that includes an exemplary compound of the present teachings (copolymer IFDKT2).
Figure 16:
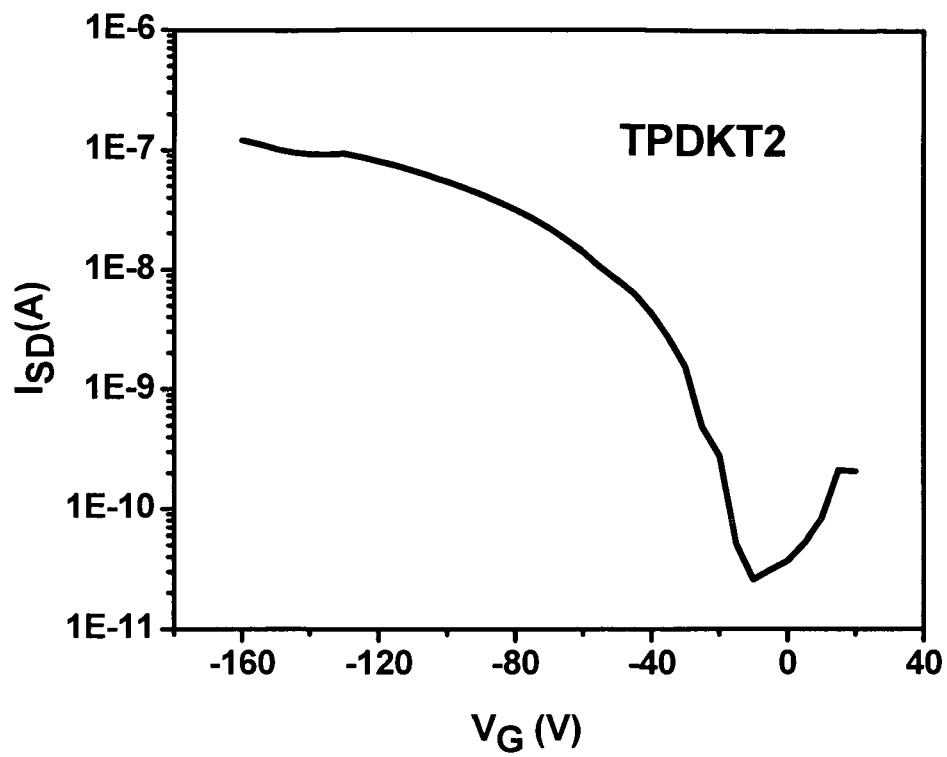
FIG. 16 is a representative transfer plot of an OFET device that includes an exemplary compound of the present teachings (copolymer TPDKT2).

Copolymers IFDKT2 and TPDKT2 exhibited hole mobilities of $2 \times 10^{-3}$ cm²/V s and $1 \times 10^{-4}$ cm²/V s, respectively, with $I_{on}/I_{off}$ ratios of ~$10^4$-$10^5$ (FIGS. 15 and 16). Without wishing to be bound by any particular theory, the negligible n-channel conduction in these polymers are believed to be possibly due to high LUMO energy levels resulting in high injection barriers >1.0 eV for electrons. Further, without wishing to be bound by any particular theory, likely due to low HOMO energy levels (~5.3-5.4 eV), p-type conduction is found to be air-stable.

Figure 17:
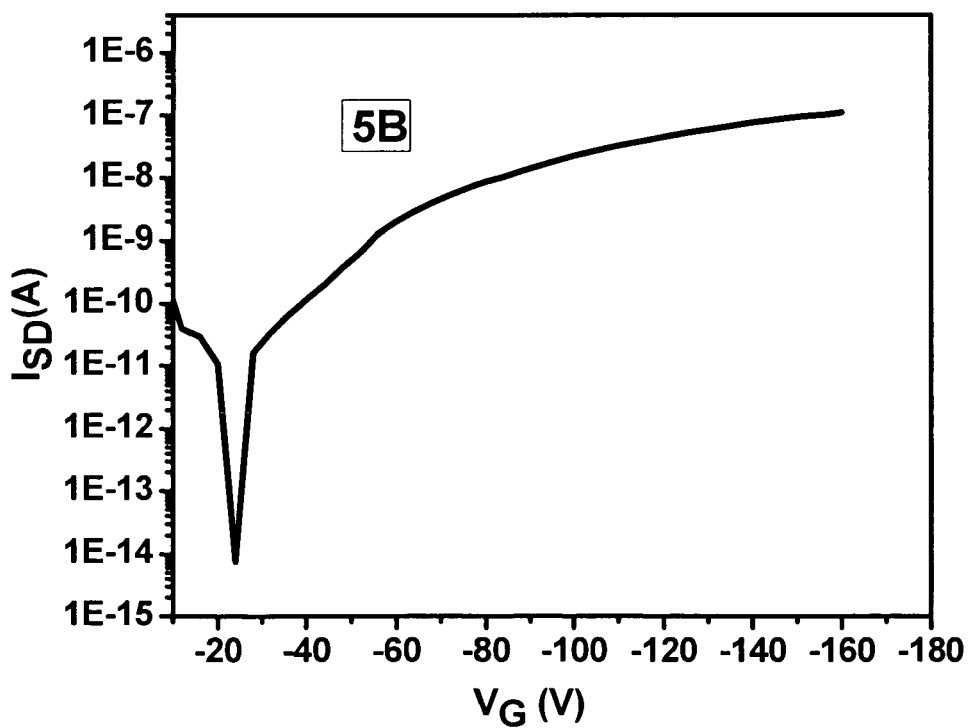
FIG. 17 is a representative p-type output plot of an OFET device that includes an exemplary compound of the present teachings (5B).
Figure 18:
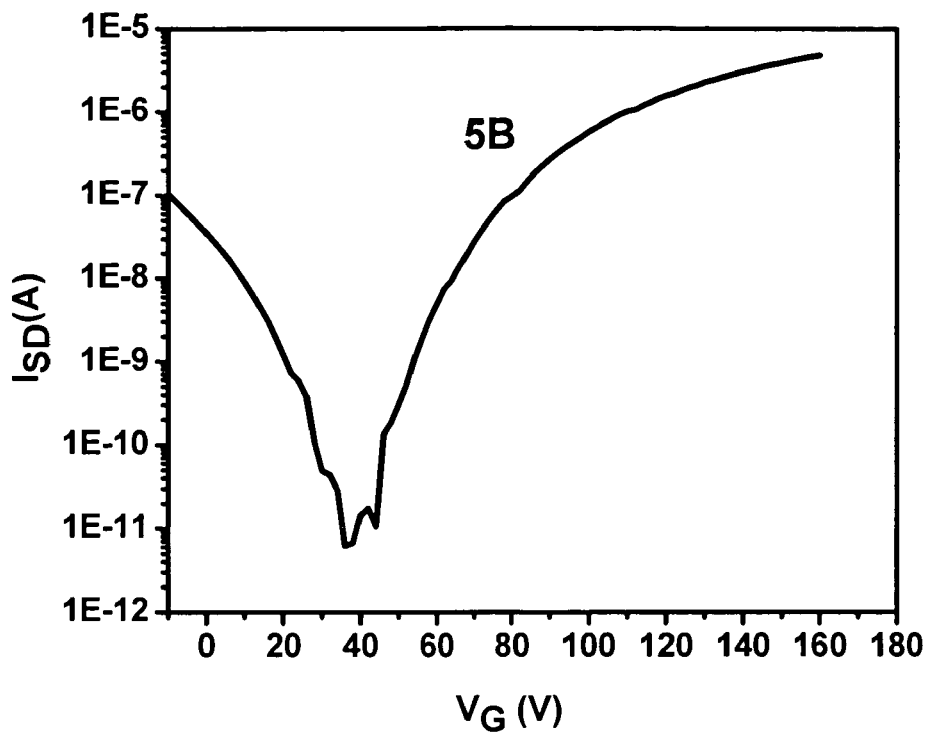
FIG. 18 is a representative n-type output plot of an OFET device that includes an exemplary compound of the present teachings (5B).
Figure 19:
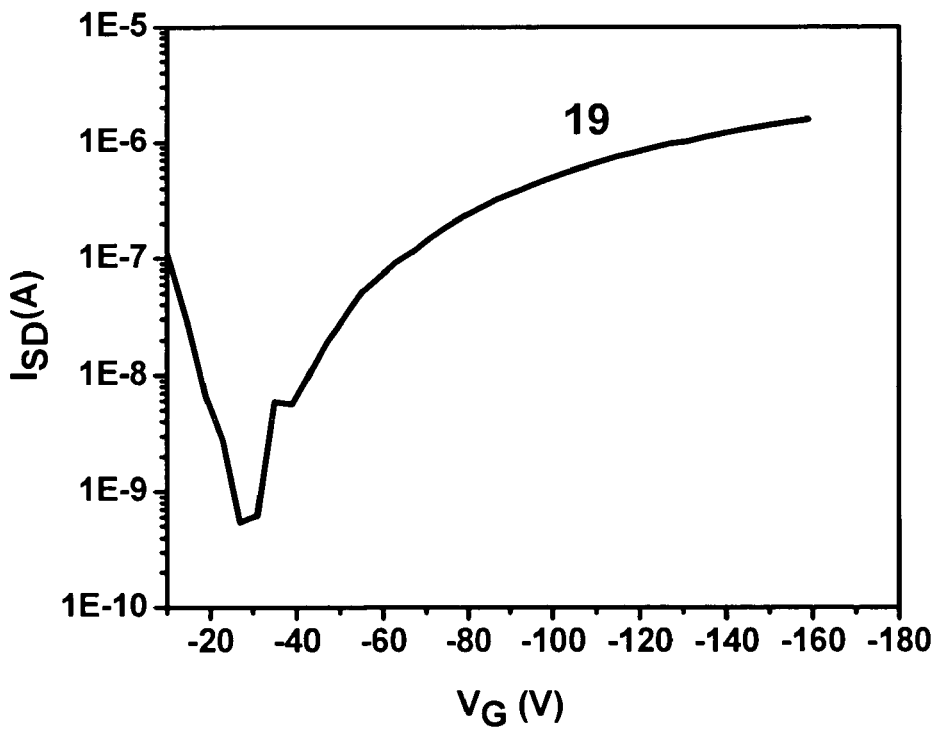
FIG. 19 is a representative p-type output plot of an OFET device that includes an exemplary compound of the present teachings (19).
Figure 21:
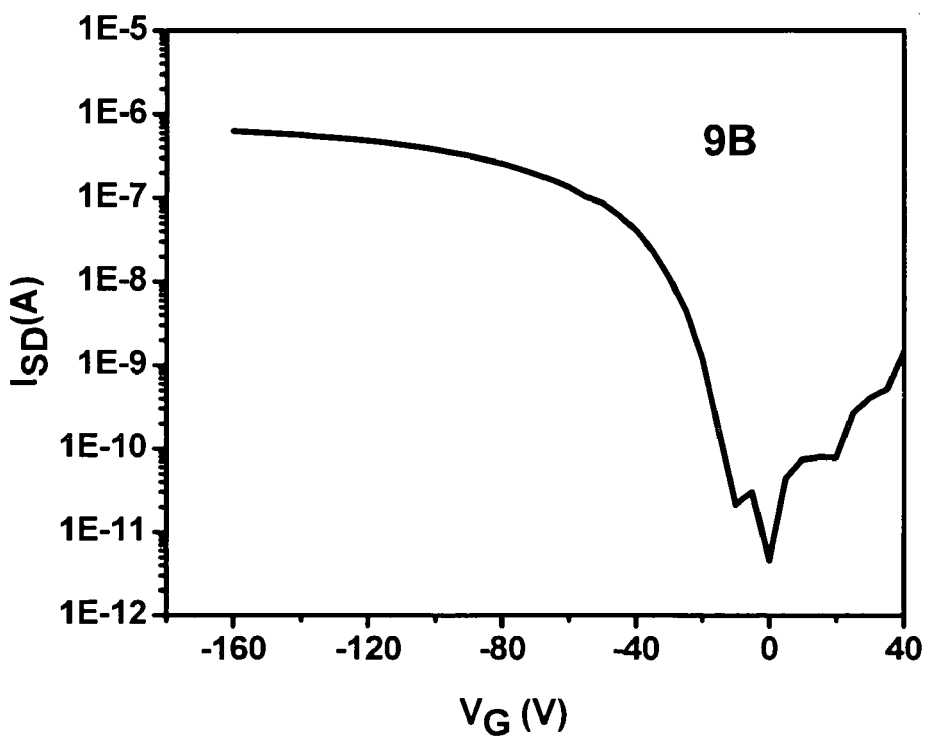
FIG. 21 is a representative p-type output plot of an OFET device that includes an exemplary compound of the present teachings (9B).

Monothiophene-ended structures 5B and 19 exhibit ambipolar behaviors. For compound 5B, electron and hole mobilities are calculated as 0.003 ($I_{on}/I_{off}$~$10^5$) cm²/V s and $4 \times 10^{-4}$ cm²/V s ($I_{on}/I_{off}$~$10^5$), respectively (FIGS. 17 and 18). Compound 19 exhibits higher electron and hole mobilities of 0.006 cm²/V s ($I_{on}/I_{off}$~$10^4$) and 0.002 cm²/V s $I_{on}/I_{off}$~$10^4$), respectively (FIGS. 19 and 20). Without wishing to be bound to any particular theory, the ambipolar behavior for these two semiconductors can be attributed to the donor-acceptor type backbone resulting in well-balanced HOMO and LUMO energy levels and low injection barriers (<0.5 eV), which in turn enhance both electron and hole injection. On the other hand, thiophene-ended compound 9B only exhibits p-type behavior with hole mobilities of $6 \times 10^{-4}$ cm² Vs and $I_{on}/I_{off}$~$10^5$ (FIG. 21). Without wishing to be bound to any particular theory, the high LUMO energy level for this compound (3.19 eV) may increase the injection barrier for the electrons resulting in an almost negligible n-channel operation.

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

What is claimed is:

1. A compound of formula I:

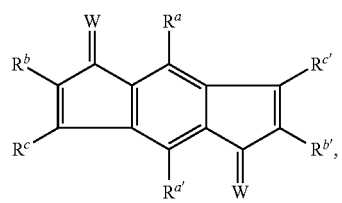

I wherein:
$R^a$ and $R^{a'}$ independently are a) H, b) a $C_{1-30}$ alkyl group, c) a $C_{2-30}$ alkenyl group, d) a $C_{2-30}$ alkynyl group, e) a $C_{1-30}$ haloalkyl group, f) a —Y—$C_{3-14}$ cycloalkyl group, g) a —Y—$C_{6-14}$ aryl group, h) a —Y-3-14 membered cycloheteroalkyl group, or i) a —Y-5-14 membered heteroaryl group, wherein each of the $C_{1-30}$ alkyl group, the $C_{2-30}$ alkenyl group, the $C_{2-30}$ alkynyl group, the $C_{1-30}$ haloalkyl group, the $C_{3-14}$ cycloalkyl group, the $C_{6-14}$ aryl group, the 3-14 membered cycloheteroalkyl group, and the 5-14 membered heteroaryl group optionally is substituted with 1-5 $R^i$ groups;

$R^b$, $R^{b'}$, $R^c$, and $R^{c'}$ independently are a) H, b) halogen, c) —CN, d) —NO₂, e) —OS(O)₂$R^e$, f) —Sn($R^e$)₃, g) —B(O$R^e$)₂, h) —Y—$R^f$, i) a $C_{1-30}$ alkyl group, j) a $C_{2-30}$ alkenyl group, k) a $C_{2-30}$ alkynyl group, or l) a $C_{1-30}$ haloalkyl group, wherein each of the $C_{1-30}$ alkyl group, the $C_{2-30}$ alkenyl group, the $C_{2-30}$ alkynyl group, and the $C_{1-30}$ haloalkyl group optionally is substituted with 1-5 $R^i$ groups, or alternatively, each of $R^b$ and $R^c$, and $R^{b'}$ and $R^{c'}$, together with each pair of carbon atoms to which each group is attached, independently forms a $C_{6-14}$ aryl group optionally substituted with 1-5 $R^d$ groups;

W, at each occurrence, independently is O, S, N$R^e$, or C(CN)₂;

$R^d$, at each occurrence, independently is a) halogen, b) —CN, c) —NO₂, d) —OS(O)₂$R^e$, e) —Sn($R^e$)₃, f) —B(O$R^e$)₂, g) —Y—$R^f$, h) =W, i) a $C_{1-30}$ alkyl group, j) a $C_{2-30}$ alkenyl group, k) a $C_{2-30}$ alkynyl group, or l) a $C_{1-30}$ haloalkyl group, wherein each of the $C_{1-30}$ alkyl group, the $C_{2-30}$ alkenyl group, the $C_{2-30}$ alkynyl group, and the $C_{1-30}$ haloalkyl group optionally is substituted with 1-5 $R^i$ groups;

$R^e$, at each occurrence, independently is H or a $C_{1-30}$ alkyl group optionally substituted with 1-5 $R^i$ groups;

$R^f$, at each occurrence, independently is -(L)$_r$-$R^g$;

L, at each occurrence, independently is a) a divalent $C_{3-14}$ cycloalkyl group, b) a divalent $C_{6-14}$ aryl group, c) a divalent 3-14 cycloheteroalkyl group, or d) a divalent 5-14 membered heteroaryl group, wherein each of a)-d) optionally is substituted with 1-5 $R^i$ groups;

$R^g$, at each occurrence, independently is a) a $C_{3-14}$ cycloalkyl group, b) a $C_{6-14}$ aryl group, c) a 3-14 cycloheteroalkyl group, or d) a 5-14 membered heteroaryl group, wherein each of a)-d) optionally is substituted with 1-5 $R^h$ groups;

$R^h$, at each occurrence, independently is a) halogen, b) —CN, c) —NO₂, d) —OS(O)₂$R^e$, e) —Sn($R^e$)₃, f) —B(O$R^e$)₂, g) a $C_{1-30}$ alkyl group, h) a $C_{2-30}$ alkenyl group, i) a $C_{2-30}$ alkynyl group, or j) a $C_{1-30}$ haloalkyl group, wherein each of the $C_{1-30}$ alkyl group, the $C_{2-30}$ alkenyl group, the $C_{2-30}$ alkynyl group, and the $C_{1-30}$ haloalkyl group optionally is substituted with 1-5 $R^i$ groups;

$R^i$, at each occurrence, independently is a) halogen, b) —CN, e) —NO₂, f) —OH, g) —NH₂, h) —O$C_{1-10}$ alkyl, i) —NH($C_{1-10}$ alkyl), j) —N($C_{1-10}$ alkyl)₂, k) —CHO, l) —C(O)OH, m) —C(O)($C_{1-10}$ alkyl), n) —C(O)O($C_{1-10}$ alkyl), o) —C(O)NH₂, p) —C(O)NH($C_{1-10}$ alkyl), q) —C(O)N($C_{1-10}$ alkyl)₂, r) a $C_{1-30}$ alkyl group, s) a $C_{2-30}$ alkenyl group, t) a $C_{2-30}$ alkynyl group, u) a $C_{1-30}$ haloalkyl group, v) a $C_{3-14}$ cycloalkyl group, w) a $C_{6-14}$ aryl group, x) a 3-14 membered cycloheteroalkyl group, or y) a 5-14 membered heteroaryl group;

Y, at each occurrence, independently is a) a divalent $C_{1-10}$ alkyl group, b) a divalent $C_{2-10}$ alkenyl group, c) a divalent $C_{2-10}$ alkynyl group, d) a divalent $C_{1-10}$ haloalkyl group, or e) a covalent bond; and r, at each occurrence, independently is 0, 1, 2, 3, 4, 5, or 6;

provided that when W is O and each of $R^b$ and $R^c$, and $R^{b'}$ and $R^{c'}$, together with each pair of carbon atoms to which each group is attached, forms a phenyl group, each of $R^a$ and $R^{a'}$ is not H or an unsubstituted phenyl group.

2. The compound of claim 1, wherein W is $C(CN)_2$.

3. The compound of claim 1, wherein the compound has formula I' or formula I":

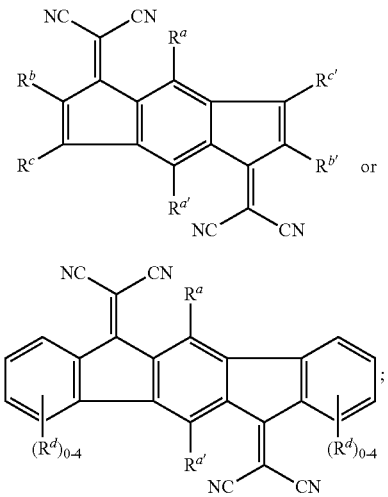

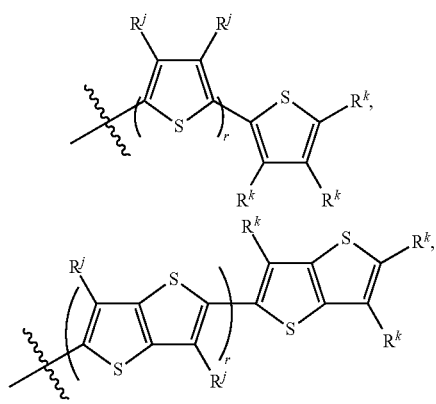

wherein $R^b$, $R^{b'}$, $R^c$, and $R^{c'}$ independently are a) H, b) halogen, c) —CN, d) —$NO_2$, e) —$OS(O)_2R^e$, f) —$Sn(R^e)_3$, g) —$B(OR^e)_2$, h) —Y—$R^f$, i) a $C_{1-30}$ alkyl group, j) a $C_{2-30}$ alkenyl group, k) a $C_{2-30}$ alkynyl group, or l) a $C_{1-30}$ haloalkyl group, wherein each of the $C_{1-30}$ alkyl group, the $C_{2-30}$ alkenyl group, the $C_{2-30}$ alkynyl group, and the $C_{1-30}$ haloalkyl group optionally is substituted with 1-5 $R^i$ groups; and $R^a$, $R^{a'}$, $R^d$, $R^e$, $R^f$, $R^i$, and Y are as defined in claim 1.

4. The compound of claim 1, wherein $R^a$ and $R^{a'}$ independently are H, a $C_{1-30}$ alkyl group, or a $C_{1-30}$ haloalkyl group.

5. The compound of claim 1, wherein $R^b$, $R^{b'}$, $R^c$, and $R^{c'}$ independently are H, halogen, —CN, —$NO_2$, —$OS(O)_2R^e$, —$Sn(R^e)_3$, —$B(OR^e)_2$, or —Y—$R^f$, and $R^e$, $R^f$, and Y are as defined in claim 1.

6. The compound of claim 5, wherein $R^b$, $R^{b'}$, $R^c$, and $R^{c'}$ independently are H or halogen.

7. The compound of claim 1, wherein $R^b$, $R^{b'}$, $R^c$, and $R^{c'}$ independently are H or -(L)$_r$-$R^g$, wherein -(L)$_r$-$R^g$, at each occurrence, independently is selected from:

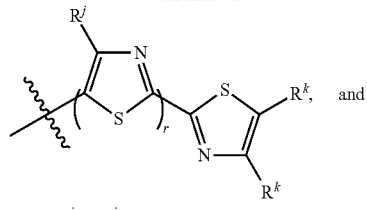

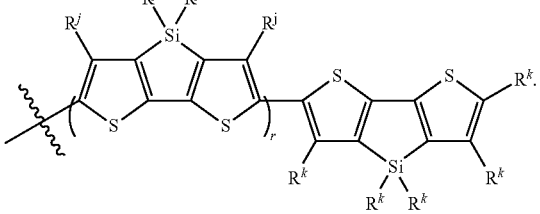

r is 0, 1, or 2; $R^j$, at each occurrence, independently is H or $R^i$; $R^k$, at each occurrence, independently is H or $R^h$; and $R^h$ and $R^i$ are as defined in claim 1.

8. The compound of claim 1, wherein $R^d$, at each occurrence, independently is selected from halogen, —CN, —$NO_2$, —$OS(O)_2R^e$, —$Sn(R^e)_3$, —$B(OR^e)_2$, and —Y—$R^f$, and $R^e$, $R^f$, and Y are as defined in claim 1.

9. The compound of claim 1, wherein $R^d$, at each occurrence, independently is selected from halogen and -(L)$_r$-$R^g$, wherein -(L)$_r$-$R^g$, at each occurrence, independently is selected from:

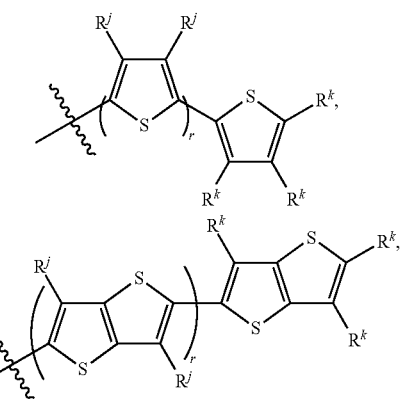

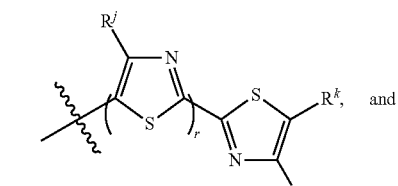

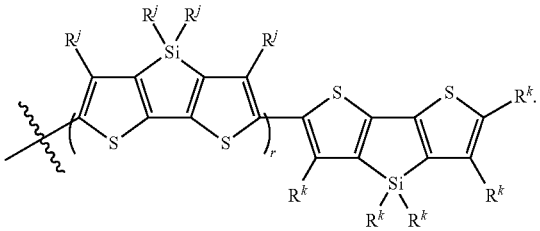

r is 0, 1, or 2; $R^j$, at each occurrence, independently is H or $R^i$; $R^k$, at each occurrence, independently is H or $R^h$; and $R^h$ and $R^i$ are as defined in claim 1.

10. The compound of claim 1 selected from:
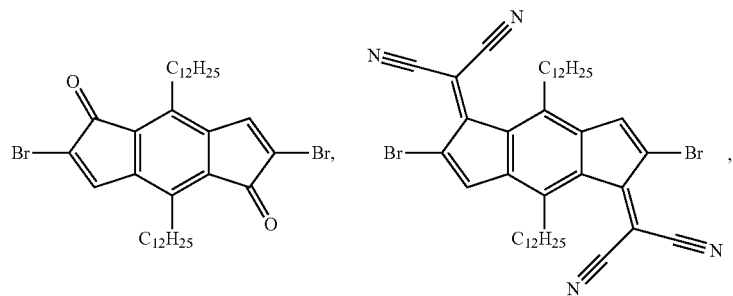
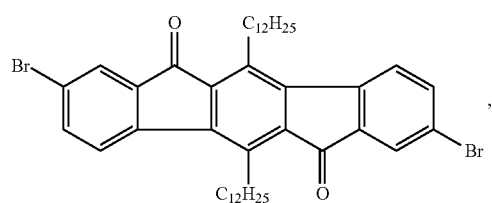
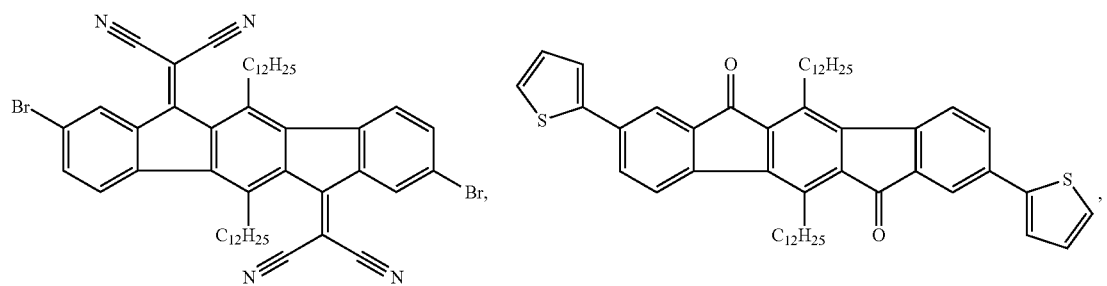
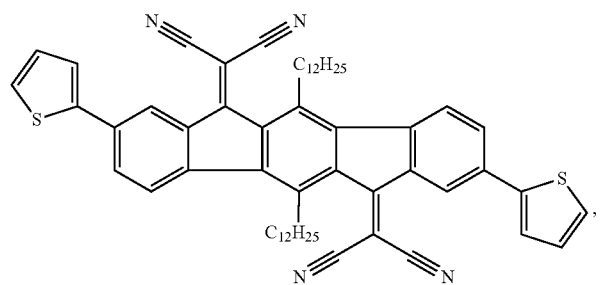
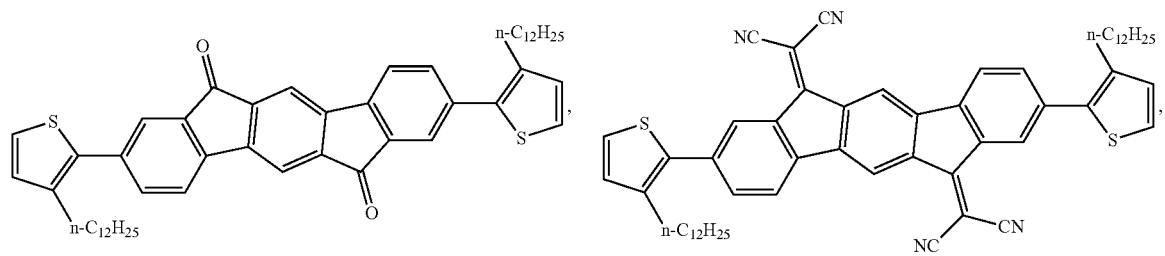

-continued
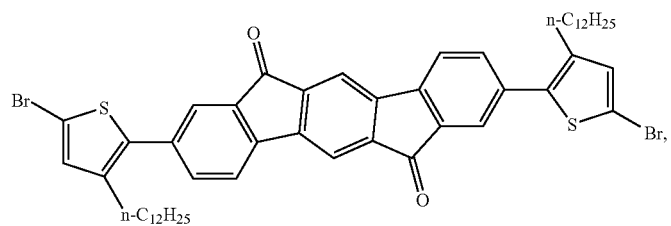
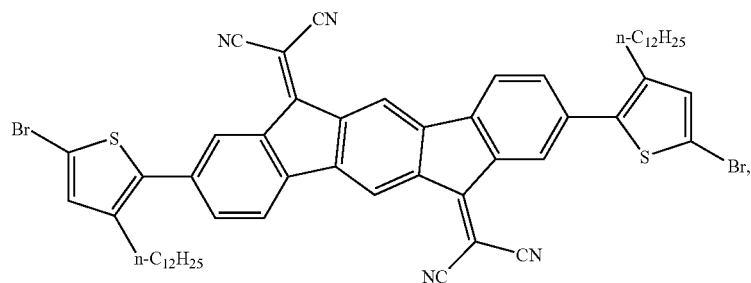
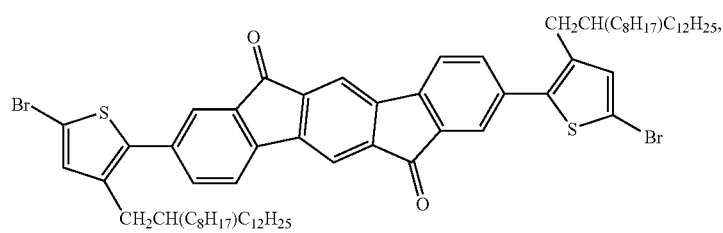
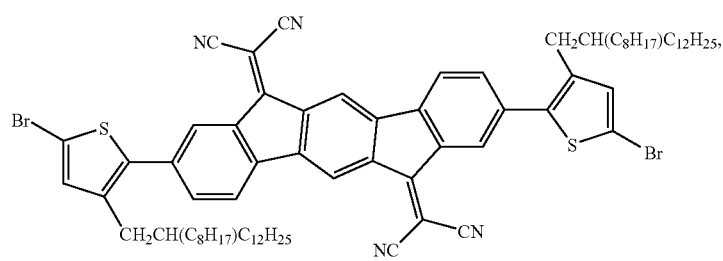
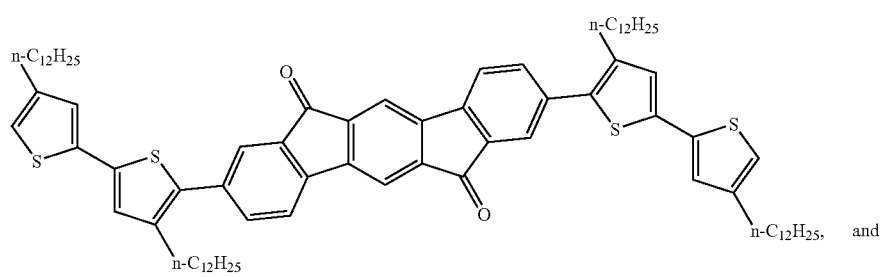
and
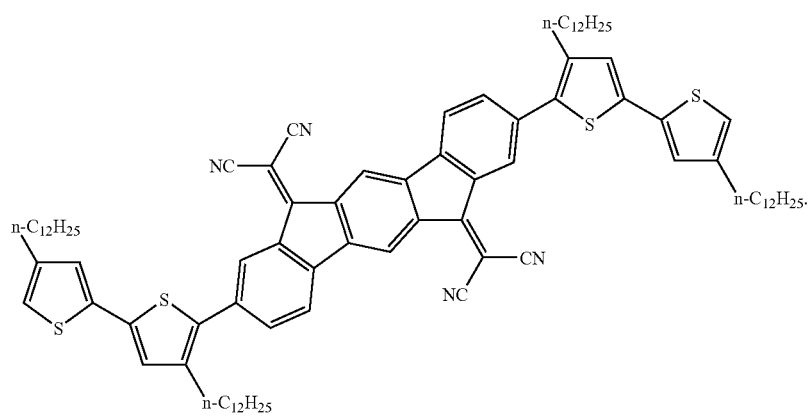

11. A compound of formula III, formula IV, or formula V:

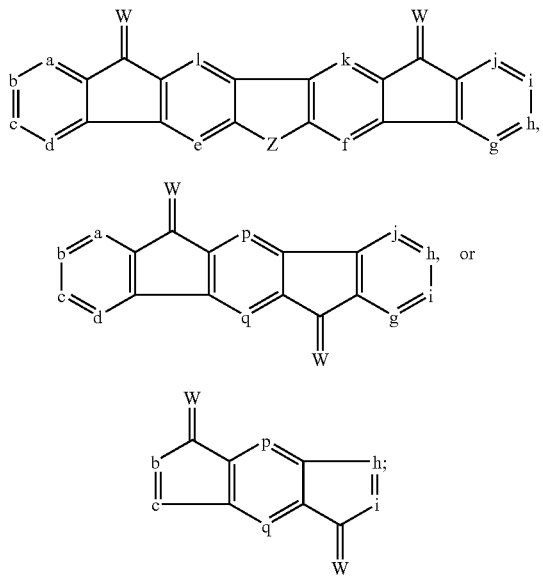

wherein:
a, d, e, f, g, j, k and l independently are $CR^1$, N, or P;
b, c, h and i independently are $CR^2$, N, or P;
p is $CR^3$;
q is $CR^4$;
W, at each occurrence, independently is O, S, $NR^1$, or $C(CN)_2$;
Y, at each occurrence, independently is a) a divalent $C_{1-10}$ alkyl group, b) a divalent $C_{2-10}$ alkenyl group, c) a divalent $C_{2-10}$ alkynyl group, d) a divalent $C_{1-10}$ haloalkyl group, or e) a covalent bond;
Z is $CR^3R^4$ or $SiR^3R^4$;
$R^1$, at each occurrence, independently is a) H, b) halogen, c) —CN, d) —$NO_2$, e) a $C_{1-30}$ alkyl group, f) a $C_{2-30}$ alkenyl group, g) a $C_{2-30}$ alkynyl group, h) a $C_{1-30}$ haloalkyl group, i) a —Y—$C_{3-14}$ cycloalkyl group, j) a —Y—$C_{6-14}$ aryl group, k) a —Y-3-14 membered cycloheteroalkyl group, or l) a —Y-5-14 membered heteroaryl group, wherein each of the $C_{1-30}$ alkyl group, the $C_{2-30}$ alkenyl group, the $C_{2-30}$ alkynyl group, the $C_{1-30}$ haloalkyl group, the $C_{3-14}$ cycloalkyl group, the $C_{6-14}$ aryl group, the 3-14 membered cycloheteroalkyl group, and the 5-14 membered heteroaryl group optionally is substituted with 1-5 $R^9$ groups;
$R^2$, at each occurrence, independently is a) H, b) halogen, c) —CN, d) —$NO_2$, e) —$OS(O)_2R^5$, f) —$Sn(R^5)_3$, g) —$B(OR^5)_2$, h) —Y—$R^6$, i) a $C_{1-30}$ alkyl group, j) a $C_{2-30}$ alkenyl group, k) a $C_{2-30}$ alkynyl group, or l) a $C_{1-30}$ haloalkyl group, wherein each of the $C_{1-30}$ alkyl group, the $C_{2-30}$ alkenyl group, the $C_{2-30}$ alkynyl group, and the $C_{1-30}$ haloalkyl group optionally is substituted with 1-5 $R^9$ groups;
$R^3$ and $R^4$ independently are a) a $C_{1-30}$ alkyl group, b) a $C_{2-30}$ alkenyl group, c) a $C_{2-30}$ alkynyl group, d) a $C_{1-30}$ haloalkyl group, e) a —Y—$C_{3-14}$ cycloalkyl group, f) a —Y—$C_{6-14}$ aryl group, g) a —Y-3-14 membered cycloheteroalkyl group, or h) a —Y-5-14 membered heteroaryl group, wherein each of the $C_{1-30}$ alkyl group, the $C_{2-30}$ alkenyl group, the $C_{2-30}$ alkynyl group, the $C_{1-30}$ haloalkyl group, the $C_{3-14}$ cycloalkyl group, the $C_{6-14}$ aryl group, the 3-14 membered cycloheteroalkyl group, and the 5-14 membered heteroaryl group optionally is substituted with 1-5 $R^9$ groups;
$R^5$, at each occurrence, independently is H or a $C_{1-30}$ alkyl group;
$R^6$, at each occurrence, independently is -$(L)_r$-$R^7$;
L, at each occurrence, independently is a) a divalent $C_{3-14}$ cycloalkyl group, b) a divalent $C_{6-14}$ aryl group, c) a divalent 3-14 cycloheteroalkyl group, or d) a divalent 5-14 membered heteroaryl group, wherein each of a)-d) optionally is substituted with 1-5 $R^9$ groups;
$R^7$, at each occurrence, is a) a $C_{3-14}$ cycloalkyl group, b) a $C_{6-14}$ aryl group, c) a 3-14 cycloheteroalkyl group, or d) a 5-14 membered heteroaryl group, wherein each of a)-d) optionally is substituted with 1-5 $R^8$ groups;
$R^8$, at each occurrence, independently is a) halogen, b) —CN, c) —$NO_2$, d) —$OS(O)_2R^5$, e) —$Sn(R^5)_3$, f) —$B(OR^5)_2$, g) a $C_{1-30}$ alkyl group, h) a $C_{2-30}$ alkenyl group, i) a $C_{2-30}$ alkynyl group, or j) a $C_{1-30}$ haloalkyl group, wherein each of the $C_{1-30}$ alkyl group, the $C_{2-30}$ alkenyl group, the $C_{2-30}$ alkynyl group, and the $C_{1-30}$ haloalkyl group optionally is substituted with 1-5 $R^9$ groups;
$R^9$, at each occurrence, independently is a) halogen, b) —CN, e) —$NO_2$, f) —OH, g) —$NH_2$, h) —$OC_{1-10}$ alkyl, i) —NH($C_{1-10}$ alkyl), j) —N($C_{1-10}$ alkyl)$_2$, k) —CHO, l) —C(O)OH, m) —C(O)($C_{1-10}$ alkyl), n) —C(O)O($C_{1-10}$ alkyl), o) —C(O)$NH_2$, p) —C(O)NH($C_{1-10}$ alkyl), q) —C(O)N($C_{1-10}$ alkyl)$_2$, r) a $C_{1-30}$ alkyl group, s) a $C_{2-30}$ alkenyl group, t) a $C_{2-30}$ alkynyl group, u) a $C_{1-30}$ haloalkyl group, v) a $C_{3-14}$ cycloalkyl group, w) a $C_{6-14}$ aryl group, x) a 3-14 membered cycloheteroalkyl group, or y) a 5-14 membered heteroaryl group; and
r, at each occurrence, independently is 0, 1, 2, 3, 4, 5, or 6.

12. The compound of claim 11, wherein b, c, h, and i independently are $CR^2$, and $R^2$, at each occurrence, independently is selected from H, halogen, —$OS(O)_2R^5$, —$SN(R^5)_3$, —$B(OR^5)_2$, and a —Y—$R^6$ group.

13. The compound of claim 11, wherein each of b and i is C(Br) or a -$(L)_r$-$R^7$ group and each of c and h is CH, wherein r is 0, 1, or 2; L, at each occurrence, is a divalent 5-membered heteroaryl group optionally substituted with 1-5 $R^9$ groups; and $R^7$ is a 5-membered heteroaryl group optionally substituted with 1-5 $R^8$ groups.

14. The compound of claim 11, wherein a, d, e, f, g, j, k, and l independently are $CR^1$.

15. The compound of claim 14, wherein each of a, d, e, f, g, j, k, and l is CH.

16. The compound of claim 11, wherein each of p and q independently is a $C(C_{6-20}$ alkyl) group or a $C(C_{6-20}$ haloalkyl) group.

17. The compound of claim 11, wherein W is O or $C(CN)_2$.

18. The compound of claim 11, wherein Z is $CR^3R^4$, and each of $R^3$ and $R^4$ independently is a $C_{6-20}$ alkyl group or a $C_{6-20}$ haloalkyl group.

19. The compound of claim 11 selected from:

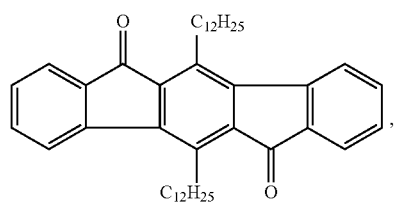

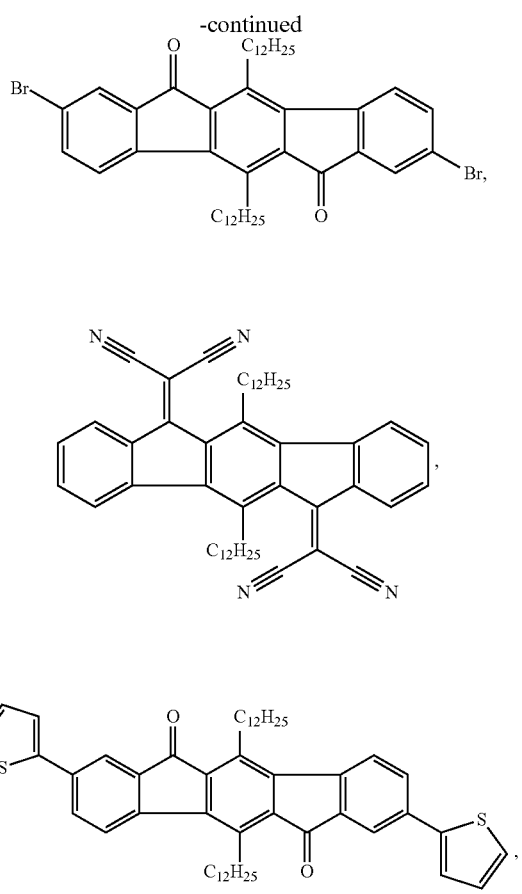
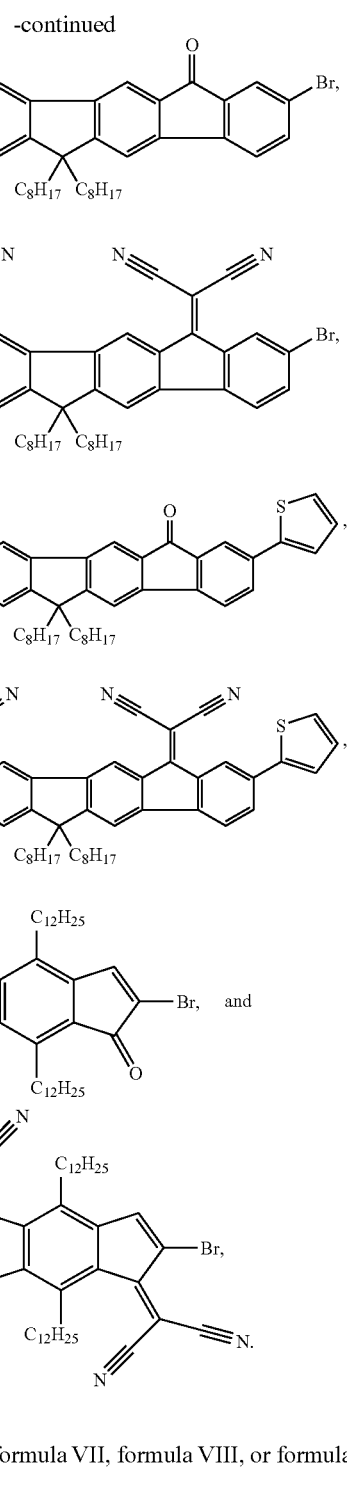
20. A compound of formula VII, formula VIII, or formula IX:
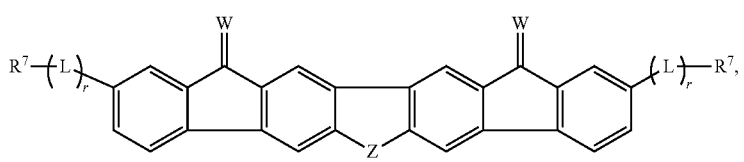

-continued

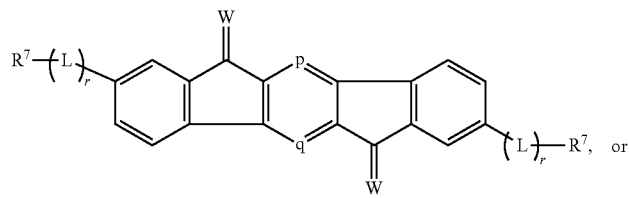

VIII

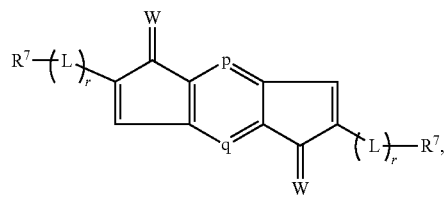

IX wherein:
p is CR³';
q is CR⁴';
W, at each occurrence, independently is O, S, NR¹, or C(CN)₂;
Y, at each occurrence, independently is a) a divalent $C_{1-10}$ alkyl group, b) a divalent $C_{2-10}$ alkenyl group, c) a divalent $C_{2-10}$ alkynyl group, d) a divalent $C_{1-10}$ haloalkyl group, or e) a covalent bond;
Z is a) CR³'R⁴', b) or SiR³'R⁴', c) C(O), d) C(S), e) C(NR⁵), or f) C(CR¹R¹);
R¹, at each occurrence, independently is a) H, b) halogen, c) —CN, d) —NO₂, e) a $C_{1-30}$ alkyl group, f) a $C_{2-30}$ alkenyl group, g) a $C_{2-30}$ alkynyl group, h) a $C_{1-30}$ haloalkyl group, i) a —Y—$C_{3-14}$ cycloalkyl group, j) a —Y—$C_{6-14}$ aryl group, k) a —Y-3-14 membered cycloheteroalkyl group, or l) a —Y-5-14 membered heteroaryl group, wherein each of the $C_{1-30}$ alkyl group, the $C_{2-30}$ alkenyl group, the $C_{2-30}$ alkynyl group, the $C_{1-30}$ haloalkyl group, the $C_{3-14}$ cycloalkyl group, the $C_{6-14}$ aryl group, the 3-14 membered cycloheteroalkyl group, and the 5-14 membered heteroaryl group optionally is substituted with 1-5 R⁹ groups;
R³' and R⁴' independently are a) H, b) a $C_{1-30}$ alkenyl group, c) a $C_{2-30}$ alkenyl group, d) a $C_{2-30}$ alkynyl group, e) a $C_{1-30}$ haloalkyl group, f) a —Y—$C_{3-14}$ cycloalkyl group, g) a —Y—$C_{6-14}$ aryl group, h) a —Y-3-14 membered cycloheteroaryl group, or i) a —Y-5-14 membered heteroaryl group, wherein each of the $C_{1-30}$ alkyl group, the $C_{2-30}$ alkenyl group, the $C_{2-30}$ alkynyl group, the $C_{1-30}$ haloalkyl group, the $C_{3-14}$ cycloalkyl group, the $C_{6-14}$ aryl group, the 3-14 membered cycloheteroalkyl group, and the 5-14 membered heteroaryl group optionally is substituted with 1-5 R⁹ groups;

R⁵, at each occurrence, independently is H or a $C_{1-30}$ alkyl group;
L, at each occurrence, independently is a) a divalent $C_{3-14}$ cycloalkyl group, b) a divalent $C_{6-14}$ aryl group, c) a divalent 3-14 cycloheteroalkyl group, or d) a divalent 5-14 membered heteroaryl group, wherein each of a)-d) optionally is substituted with 1-5 R⁹ groups;
R⁷, at each occurrence, is a) a $C_{3-14}$ cycloalkyl group, b) a $C_{6-14}$ aryl group, c) a 3-14 cycloheteroalkyl group, or d) a 5-14 membered heteroaryl group, wherein each of a)-d) optionally is substituted with 1-5 R⁸ groups;
R⁸, at each occurrence, independently is a) halogen, b) —CN, c) —NO₂, d) —OS(O)₂R⁵, e) —Sn(R⁵)₃, f) —B(OR⁵)₂, g) a $C_{1-30}$ alkyl group, h) a $C_{2-30}$ alkenyl group, i) a $C_{2-30}$ alkynyl group, or j) a $C_{1-30}$ haloalkyl group, wherein each of the $C_{1-30}$ alkyl group, the $C_{2-30}$ alkenyl group, the $C_{2-30}$ alkynyl group, and the $C_{1-30}$ haloalkyl group optionally is substituted with 1-5 R⁹ groups;
R⁹, at each occurrence, independently is a) halogen, b) —CN, e) —NO₂, f) —OH, g) —NH₂, h) —OC$_{1-10}$ alkyl, i) —NH(C$_{1-10}$ alkyl), j) —N(C$_{1-10}$ alkyl)₂, k) —CHO, l) —C(O)OH, m) —C(O)(C$_{1-10}$ alkyl), n) —C(O)O(C$_{1-10}$ alkyl), o) —C(O)NH₂, p) —C(O)NH(C$_{1-10}$ alkyl), q) —C(O)N(C$_{1-10}$ alkyl)₂, r) a C$_{1-30}$ alkyl group, s) a C$_{2-30}$ alkenyl group, t) a C$_{2-30}$ alkynyl group, u) a C$_{1-30}$ haloalkyl group, v) a C$_{3-14}$ cycloalkyl group, w) a C$_{6-14}$ aryl group, x) a 3-14 membered cycloheteroalkyl group, or y) a 5-14 membered heteroaryl group; and
r, at each occurrence, independently is 0, 1, 2, 3, 4, 5, or 6.
21. The compound of claim 20, wherein W, at each occurrence, independently is C(CN)₂.
22. The compound of claim 20 selected from:

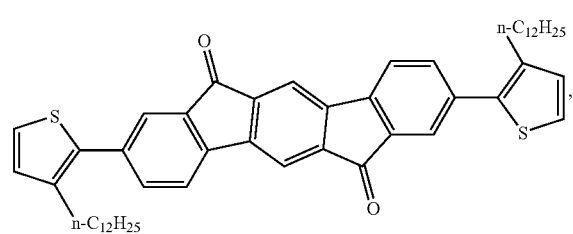

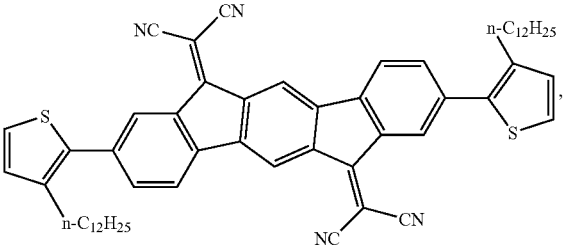

-continued
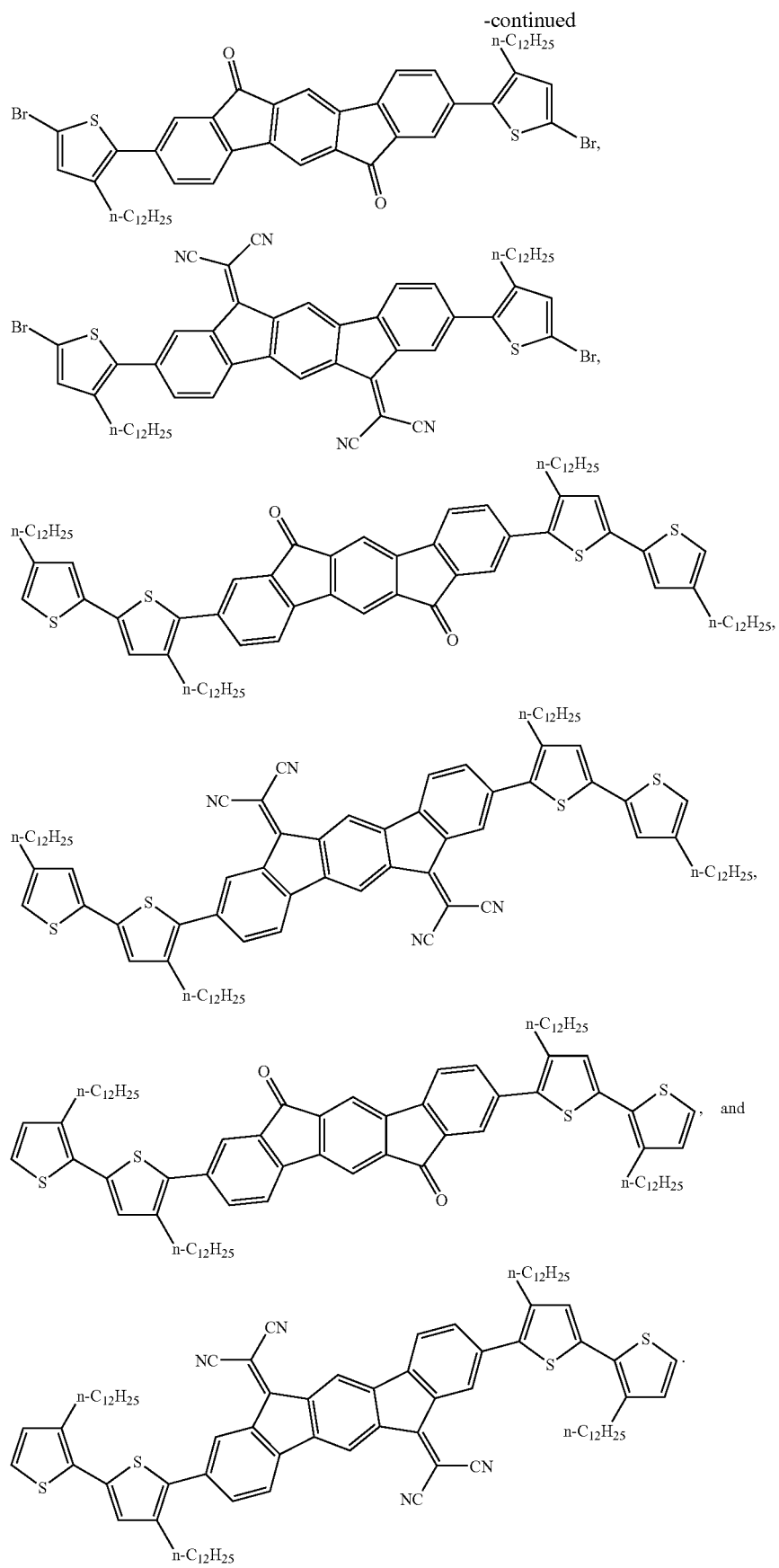

23. An article of manufacture comprising one or more compounds of claim 1.

24. The article of manufacture of claim 23, wherein the article of manufacture is an electronic device, an optical device, or an optoelectronic device.

25. A thin film semiconductor comprising one or more compounds of claim 1.

26. A composite comprising a substrate and the thin film semiconductor of claim 25 deposited on the substrate.

27. A field effect transistor device comprising the thin film semiconductor of claim 25.

28. A field effect transistor device comprising the composite of claim 26.

29. The field effect transistor device of claim 27 comprising a dielectric material, wherein the dielectric material comprises an organic dielectric material, an inorganic dielectric material, or a hybrid organic/inorganic dielectric material.

30. A photovoltaic device comprising the thin film semiconductor of claim 25.

31. A photovoltaic device comprising the composite of claim 26.

32. The photovoltaic device of claim 30 comprising a p-type semiconducting material adjacent to the one or more compounds of formula I.

33. An organic light emitting diode device comprising the thin film semiconductor of claim 25.

34. An organic light emitting diode device comprising the composite of claim 26.

35. A method of making an article of manufacture, the method comprising depositing a composition comprising one or more compounds of claim 1 dissolved in a liquid medium onto a substrate.

36. The method of claim 35, wherein depositing the composition comprises at least one of printing, spin coating, drop-casting, zone casting, dip coating, blade coating, and spraying.

37. The compound of claim 1, wherein each of $R^b$ and $R^c$, and $R^{b'}$ and $R^{c'}$, together with each pair of carbon atoms to which each group is attached, independently forms a $C_{6-14}$ aryl group substituted with 1-5 $R^d$ groups, wherein $R^d$, at each occurrence, independently is selected from halogen and

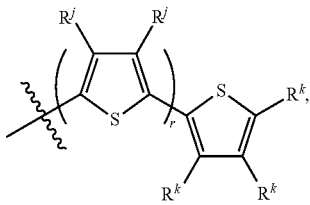

wherein r is 0, 1, or 2; $R^j$, at each occurrence, independently is H or $R^i$; $R^k$, at each occurrence, independently is H or $R^h$; and $R^h$ and $R^i$ are as defined in claim 1.

38. The field effect transistor device of claim 28 comprising a dielectric material, wherein the dielectric material comprises an organic dielectric material, an inorganic dielectric material, or a hybrid organic/inorganic dielectric material.

39. The photovoltaic device of claim 31 comprising a p-type semiconducting material adjacent to the one or more compounds of formula I.

40. An article of manufacture comprising one or more compounds of claim 10, wherein the article of manufacture is an electronic device, an optical device, or an optoelectronic device.

41. A thin film semiconductor comprising one or more compounds of claim 10.

42. A field effect transistor device comprising the thin film semiconductor of claim 41.

43. A thin film semiconductor comprising one or more compounds of claim 11.

44. A composite comprising a substrate and the thin film semiconductor of claim 43 deposited on the substrate.

45. An article of manufacture comprising the composite of claim 44, wherein the article of manufacture is an electronic device, an optical device, or an optoelectronic device.

46. An electronic, optical, or optoelectronic device comprising the thin film semiconductor of claim 43, wherein the device is a field effect transistor, a photovoltaic device, or an organic light emitting diode device.

47. An electronic, optical, or optoelectronic device comprising the composite of claim 44, wherein the device is a field effect transistor, a photovoltaic device, or an organic light emitting diode device.

48. A method of making an article of manufacture, the method comprising depositing a composition comprising one or more compounds of claim 11 dissolved in a liquid medium onto a substrate.

49. The method of claim 48, wherein depositing the composition comprises at least one of printing, spin coating, drop-casting, zone casting, dip coating, blade coating, and spraying.

50. An article of manufacture comprising one or more compounds of claim 19, wherein the article of manufacture is an electronic device, an optical device, or an optoelectronic device.

51. A thin film semiconductor comprising one or more compounds of claim 19.

52. A field effect transistor device comprising the thin film semiconductor of claim 51.

53. A thin film semiconductor comprising one or more compounds of claim 20.

54. A composite comprising a substrate and the thin film semiconductor of claim 53 deposited on the substrate.

55. An article of manufacture comprising one or more compounds of claim 20, wherein the article of manufacture is an electronic device, an optical device, or an optoelectronic device.

56. An electronic, optical, or optoelectronic device comprising the thin film semiconductor of claim 53, wherein the device is a field effect transistor, a photovoltaic device, or an organic light emitting diode device.

57. An electronic, optical, or optoelectronic device comprising the composite of claim 54, wherein the device is a field effect transistor, a photovoltaic device, or an organic light emitting diode device.

58. A method of making an article of manufacture, the method comprising depositing a composition comprising one or more compounds of claim 20 dissolved in a liquid medium onto a substrate.

59. The method of claim 58, wherein depositing the composition comprises at least one of printing, spin coating, drop-casting, zone casting, dip coating, blade coating, and spraying.

60. A thin film semiconductor comprising one or more compounds of claim 22.

61. A composite comprising a substrate and the thin film semiconductor of claim 60 deposited on the substrate.

62. An article of manufacture comprising the thin film semiconductor of claim 60, wherein the article of manufacture is an electronic device, an optical device, or an optoelectronic device.

63. An article of manufacture comprising the composite of claim 61, wherein the article of manufacture is an electronic device, an optical device, or an optoelectronic device.

64. A field effect transistor device comprising the thin film semiconductor of claim 60.

65. A field effect transistor device comprising the composite of claim 61.

66. A photovoltaic device comprising the thin film semiconductor of claim 60.

67. A photovoltaic device comprising the composite of claim 61.

68. An organic light emitting diode device comprising the thin film semiconductor of claim 60.

69. An organic light emitting diode device comprising the composite of claim 61.

70. A method of making an article of manufacture, the method comprising depositing a composition comprising one or more compounds of claim 22 dissolved in a liquid medium onto a substrate.

71. The method of claim 70, wherein depositing the composition comprises at least one of printing, spin coating, drop-casting, zone casting, dip coating, blade coating, and spraying.

* * * * *

UNITED STATES PATENT AND TRADEMARK OFFICE
CERTIFICATE OF CORRECTION

PATENT NO. : 7,928,249 B2
APPLICATION NO. : 12/221123
DATED : April 19, 2011
INVENTOR(S) : Marks et al.

It is certified that error appears in the above-identified patent and that said Letters Patent is hereby corrected as shown below:

At column 1, lines 16-20, please delete the paragraph under the heading "STATEMENT REGARDING FEDERALLY SPONSORED RESEARCH OR DEVELOPMENT," and replace it with the following paragraph:

--This invention was made with government support under grant number N00014-02-1-0909 and grant number N00014-05-1-0541 awarded by the Office of Naval Research. The government has certain rights in the invention.--

Signed and Sealed this
Fifth Day of July, 2011

David J. Kappos
*Director of the United States Patent and Trademark Office*

UNITED STATES PATENT AND TRADEMARK OFFICE
CERTIFICATE OF CORRECTION

PATENT NO. : 7,928,249 B2
APPLICATION NO. : 12/221123
DATED : April 19, 2011
INVENTOR(S) : Marks et al.

It is certified that error appears in the above-identified patent and that said Letters Patent is hereby corrected as shown below:

In claim 1, at col. 90, line 17, delete "optionally".

In claim 3, at col. 91, line 25, formula I", delete:

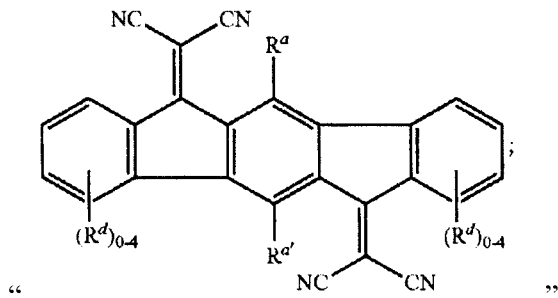

" ";

and insert,

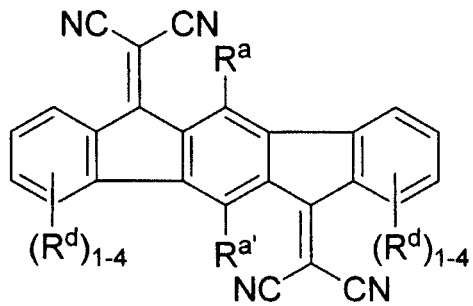

-- --.

In claim 9, at col. 92, line 28, delete "-(L)$_r$-R$^9$" and insert -- -(L)$_r$-R$^g$ --.

In claim 12, at col. 98, line 36, delete "—SN(R$^5$)$_3$" and insert -- —Sn(R$^5$)$_3$ --.

Signed and Sealed this
Eighth Day of November, 2011

David J. Kappos
*Director of the United States Patent and Trademark Office*

In claim 19, at col. 99, line 25, insert:
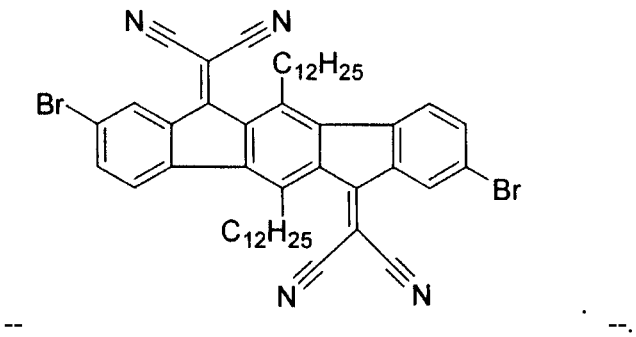
--.
In claim 20, at col. 101, line 44, delete "b) a $C_{1-30}$ alkenyl group" and insert --b) a $C_{1-30}$ alkyl group--.
In claim 20, at col. 101, lines 47-48, delete "h) a —Y-3-14 membered cycloheteroaryl group" and insert --h) a —Y-3-14 membered cycloheteroalkyl group--.